(12) United States Patent
Jewett et al.

(10) Patent No.: US 10,118,950 B2
(45) Date of Patent: Nov. 6, 2018

(54) **PLATFORMS FOR CELL-FREE PROTEIN SYNTHESIS COMPRISING EXTRACTS FROM GENOMICALLY RECODED *E. COLI* STRAINS HAVING GENETIC KNOCK-OUT MUTATIONS IN RELEASE FACTOR 1 (RF-1) AND ENDA**

(71) Applicant: Northwestern University, Evanston, IL (US)

(72) Inventors: Michael Christoper Jewett, Evanston, IL (US); Rey William Martin, Evanston, IL (US); Seok Hoon Hong, Chicago, IL (US); Yong Chan Kwon, Evanston, IL (US); Benjamin James Des Soye, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/840,249

(22) Filed: Aug. 31, 2015

(65) Prior Publication Data
US 2016/0060301 A1    Mar. 3, 2016

Related U.S. Application Data

(60) Provisional application No. 62/044,221, filed on Aug. 30, 2014.

(51) Int. Cl.
| | | |
|---|---|---|
| *C07K 14/00* | (2006.01) | |
| *C12P 21/00* | (2006.01) | |
| *C12N 9/12* | (2006.01) | |
| *C12P 21/02* | (2006.01) | |

(52) U.S. Cl.
CPC .......... *C07K 14/001* (2013.01); *C12N 9/1247* (2013.01); *C12P 21/00* (2013.01); *C12P 21/02* (2013.01); *C12Y 207/07006* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 5,494,810 A | 2/1996 | Barany et al. |
| 7,338,789 B2 | 3/2008 | Swartz et al. |
| 8,357,529 B2 | 1/2013 | Swartz et al. |
| 2004/0209321 A1 | 10/2004 | Swartz et al. |
| 2007/0154983 A1 | 7/2007 | Calhoun et al. |
| 2008/0138857 A1 | 6/2008 | Swartz et al. |
| 2011/0195483 A1* | 8/2011 | Tian ................. C12N 1/36 435/252.8 |
| 2012/0171720 A1 | 7/2012 | Church et al. |
| 2014/0295492 A1 | 10/2014 | Jewett et al. |
| 2015/0259757 A1 | 9/2015 | Jewett et al. |
| 2016/0257945 A1* | 9/2016 | Zimmerman ......... C12P 21/02 |
| 2016/0257946 A1* | 9/2016 | Zimmerman ......... C07K 1/02 |

FOREIGN PATENT DOCUMENTS

WO    2015184283 A1    12/2015

OTHER PUBLICATIONS

Bundy, B.C. & Swartz, J.R. Bioconjugate Chemistry 21, 255-263 (2010).
Calhoun, K.A. & Swartz, J.R. Journal of Biotechnology 123, 193-203 (2006).
Chatterjee, A. et al. Angew. Chem. Int. Ed. 52, 5106-5109 (2013).
Chen, Y.J. et al. Nat Methods 10, 659-706 (2013).
Chin, J.W. Annual Review of Biochemistry 83, 379-411 (2014).
Dudley, Q.M. et al. Biotechnology Journal 10, 69-82 (2015).
Goerke, A.R. & Swartz, J.R. Biotechnology and Bioengineering 102, 400-416 (2009).
Hong, S.H. et al. Chembiochem: a European Journal of Chemical Biology 16, 844-853 (2015).
Jewett, M.C. & Swartz, J.R. Biotechnology and Bioengineering 86, 19-25 (2004).
Jewett, M.C. et al. Journal of Bacteriology 191, 1083-1091 (2009).
Jiang, X. et al. Journal of Bioscience and Bioengineering 93, 151-156 (2002).
Kim, D.-M. & Choi, C.-Y. Biotechnol. Prog. 12, 645-649 (1996).
Kim, D.-M. et al. European Journal of Biochemistry. 239, 881-886 (1996).
Kim, D.-M. & Swartz, J.R. Biotechnol. Bioeng. 74, 309-316 (2001).
Kim, T.W. et al. Biotechnol Bioproc E 13, 464-469 (2008).
Liu, C.C. & Schultz, P.G. Annual Review of Biochemistry 79, 413-444 (2010).
Liu, Y. et al. ACS Synth. Biol. 4, 454-462 (2015).
Lu, Y. et al. Biotechnology and Bioengineering 110, 2073-2085 (2013).
Michel-Reydellet, N., et al. Journal of Molecular Microbiology and Biotechnology 9, 26-34 (2005).
Michel-Reydellet, N., et al. Metabolic Engineering 6, 197-203 (2004).
Plass, T. et al. Angew. Chem. Int. Ed. 51, 4166-4170 (2012).
Raines, R.T. Chemical Reviews 98, 1045-1065 (1998).
Schoborg, J.A. et al. Biotechnology Journal 9, 630-640 (2014).
Swartz, J.R. et al. Methods in Molecular Biology 267, 169-182 (2004).

(Continued)

*Primary Examiner* — Nancy A Treptow
(74) *Attorney, Agent, or Firm* — Andrus Intellectual Property Law, LLP

(57) ABSTRACT

The invention relates to genomically recoded organisms, platforms for preparing sequence defined biopolymers in vitro comprising a cellular extract from a genomically recorded organism, and methods for preparing sequence defined biopolymers in vitro are described. In particular, the invention relates to genomically recoded organisms comprising a strain deficient in release factor 1 (RF-1) or a genetic homolog thereof and at least one of at least one additional genetic knock-out mutation, at least one additional upregulated gene product, or both at least one additional knock-out mutation and at least one additional upregulated gene product.

23 Claims, 16 Drawing Sheets

Specification includes a Sequence Listing.

(56) References Cited

OTHER PUBLICATIONS

Ugwumba, I.N. et al. Journal of the American Chemical Society 133, 326-333 (2011).
Voloshin, A.M. & Swartz, J.R. Biotechnol. Bioeng. 91, 516-521 (2005).
Yang, J. et al. Biotechnology Progress 20, 1689-1696 (2004).
Yang, W.C. et al. Biotechnology and Bioengineering 104, 1047-1058 (2009).
Young, T.S. et al. Journal of Molecular Biology 395, 361-374 (2010).
Zawada, J. & Swartz, J. Biotechnol. Bioeng. 89, 407-415 (2005).
Chu et al., Enzyme and Microbial Technology 46 (2010) 87-91.
Airen, I.O. in Stanford University, vol. PhD (Stanford University (USA), 2011).
Albayrak, C. & Swartz, J.R. Nucleic acids research 41, 5949 (2013).
Borja, G. et al., Microb. Cell Fact. 11, 132 (2012).
Carlson, E.D. et al. Biotechnology advances 30, 1185 (2012).
Caschera, F. & Noireaux, V. Biochimie 99, 162 (2014).
Chappell, J. et al. Nucleic acids research 41, 3471 (2013).
Chatterjee, A. et al. Biochemistry 52, 1828 (2013).
Chen, J. et al. J. Mol. Microbiol. Biotechnol. 4, 255 (2002).
Chizzolini, F. et al. ACS Synth. Biol. 3, 363 (2014).
Chu, H.S. et al. Protein expression and purification 74, 298 (2010).
Des Soye, B.J. et al. Current opinion in chemical biology 28, 83 (2015).
Fritz, B.R. & Jewett, M.G. Nucleic acids research 42, 6774 (2014).
Gallagher, R.R. et al. Nucleic acids research 43, 1945 (2015).
Gibson, D.G. et al. Nat. Methods 6, 343 (2009).
Hong, S.H. et al. ACS synthetic biology 3, 398 (2014).
Hong, S.H. et al. Frontiers in chemistry 2, 34 (2014).
Jewett, M.C. et al. Molecular systems biology 4, 220 (2008).
Jewett, M.C. et al. Journal of bacteriology 191, 1083 (2009).
Johnson, D.B. et al. Nature chemical biology 7, 779 (2011).
Kwon, Y.C. & Jewett, M.C. Scientific reports 5, 8663 (2015).
Lajoie, M.J. et al. Science 342, 357 (2013).
Lehman, I.R. et al. J. Biol. Chem. 237, 829 (1962).
Loscha, K.V. et al. Angewandte Chemie (International ed. in English) 51, 2243 (2012).
Sun, S.B. et al. Chembiochem : a European journal of chemical biology 15, 1721 (2014).
Takahashi, M.K. et al. Methods (2015).
Wang, H.H. Nature 460, 894 (2009).
Wang, H.H. & Church, G.M. Methods in enzymology 498, 409 (2011).
Young, T.S. et al. Journal of molecular biology 395, 361 (2010).
Zawada, J.F. et al. Biotechnology and bioengineering 108, 1570 (2011).
Website print-out order sheet for *E. coli* strain C321.ΔA (Bacterial strain #48998), from addgene, Feb. 9, 2017.
Website print-out order sheet for *E. coli* strain rec13.ΔprfA (Bacterial strain #69495), from addgene, Apr. 9, 2017.

\* cited by examiner

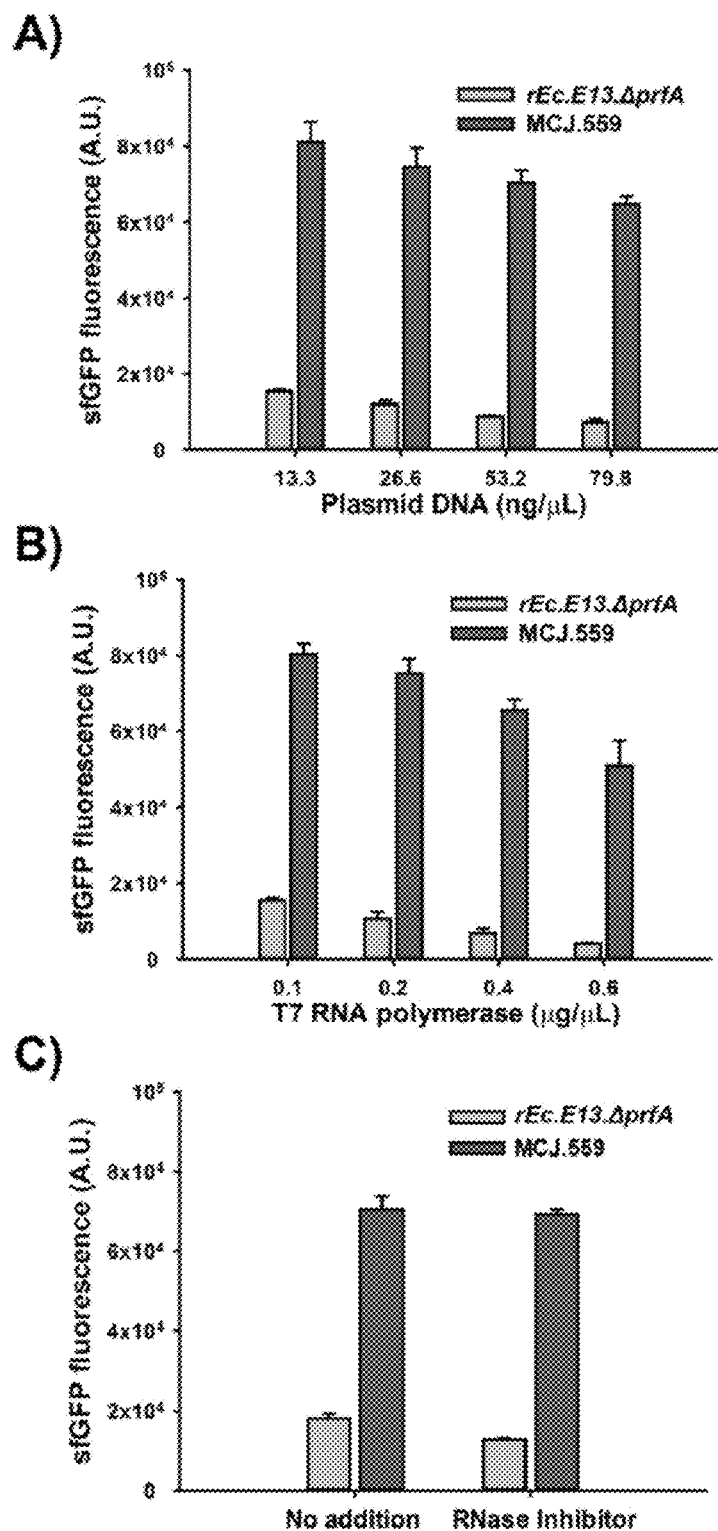
FIGURE 3A-C

FIGURE 6A-C

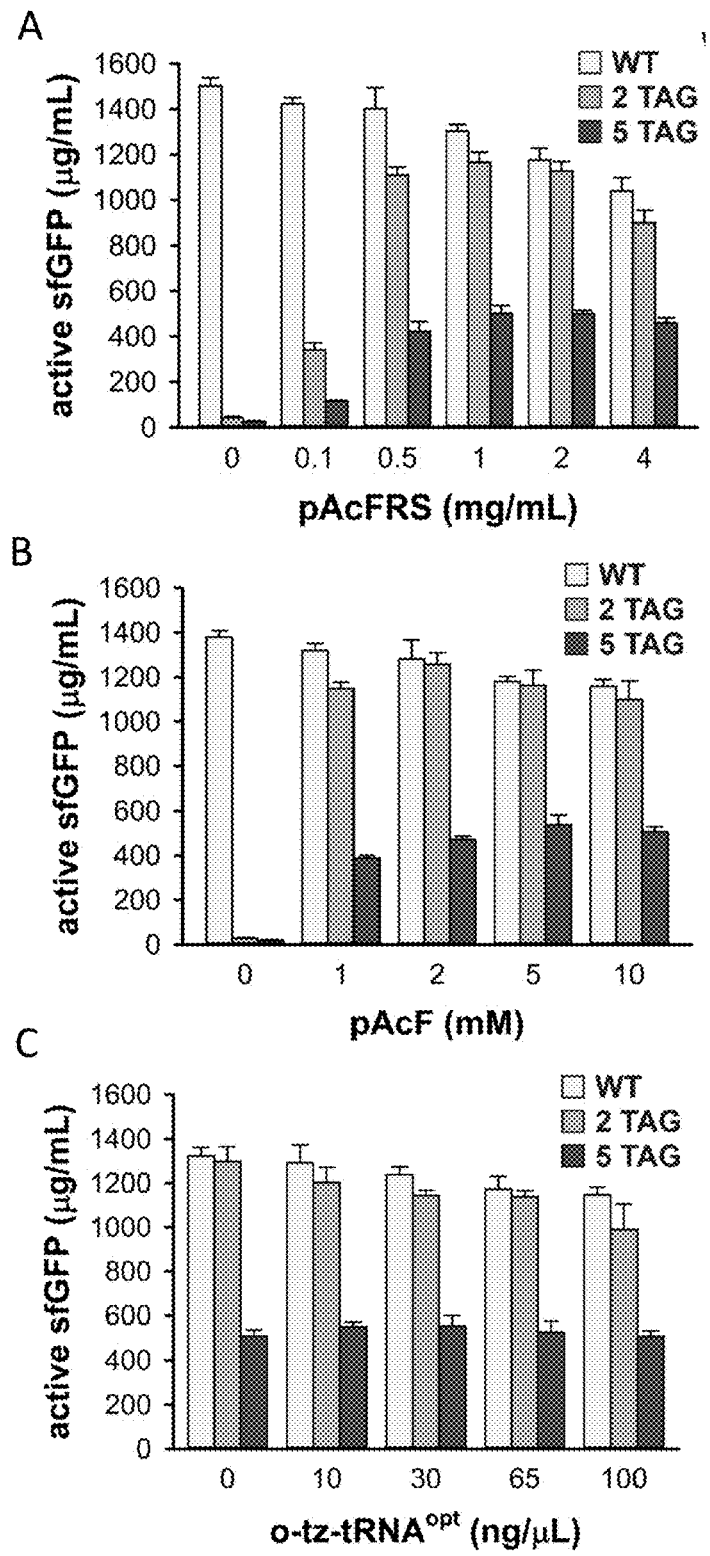
FIGURE 12A-C

US 10,118,950 B2

PLATFORMS FOR CELL-FREE PROTEIN SYNTHESIS COMPRISING EXTRACTS FROM GENOMICALLY RECODED *E. COLI* STRAINS HAVING GENETIC KNOCK-OUT MUTATIONS IN RELEASE FACTOR 1 (RF-1) AND ENDA

CROSS-REFERENCE TO RELATED APPLICATIONS

This application claims benefit of U.S. Provisional Application No. 62/044,221, filed 30 Aug. 2014, the disclosure of which is incorporated by reference in its entirety.

STATEMENT OF GOVERNMENTAL INTEREST

This invention was made with government support under W911NF-11-1-0445 awarded by the Army Research Office; N00014-11-1-0363 awarded by the Office of Naval Research; N66001-12-C-4211 (Yale subcontract to Northwestern University, C13K11518 (K00183)) and N66001-13-C-4024 (Leidos subcontract P010152319 to Northwestern University) awarded by Space and Naval Warfare Systems Center (DARPA). The government has certain rights in the invention.

INCORPORATION BY REFERENCE OF MATERIAL SUBMITTED ELECTRONICALLY

This application contains, as a separate part of disclosure, a Sequence Listing in computer-readable form (filename: 0101_0106_02_ST25.txt, 35,024 bytes, ASCII text file) which is incorporated by reference in its entirety.

BACKGROUND

*Escherichia coli* cell-free protein synthesis (CFPS) has undergone a transformational shift from an exploratory platform used in the discovery of the genetic code to a present-day, high-yielding protein production platform[1]. This shift is fueled by the open nature of this system, allowing for rapid combination, supplementation, and optimization of the physiochemical environment for increasing protein yields and batch reaction duration[2, 3]. Now, cell-free systems are seen as a complement to in vivo protein expression and can be used as both a prototyping platform due to its simplicity, easiness, and modular design for protein expression[4-6] as well as a large-scale production platform for difficult to express proteins in vivo[7]. The transition from exploratory platform to high-yielding protein production platform has come about, at least in part, by complex strain engineering to stabilize biological substrates in the cell-free reaction mixtures[8, 9]. These genetic modifications targeted the deletion of proteins known to affect the stability of DNA[10], mRNA[8, 11], protein[12], energy[13], and amino acids[14, 15] in the cell-free reaction. In addition to strain engineering efforts, activation of multiple biological pathways[16], decreases in cost[17], and improved understanding of reaction contents makes CFPS an attractive platform for the production of new kinds of high-value proteins.

One area of great interest for the application of cell-free systems is the production of modified proteins containing non-standard amino acids. Incorporating non-standard amino acids or unnatural amino acids (NSAAs) allows for the production of proteins with novel structures and functions that are difficult or impossible to create using the 20 canonical amino acids[18, 19]. Recently, cell-free protein synthesis (CFPS) systems have been employed to increase yields of proteins bearing NSAAs[20, 21], achieve direct protein-protein conjugation[22], explore drug discovery[23], and enhance enzyme activity[24, 25].

Typically, NSAA incorporation systems use amber suppression technology to insert NSAAs into proteins, a method by which an in-frame amber (TAG) stop codon is utilized as a sense codon for assigning NSAAs[26, 27]. Amber suppression technology, however, has limited efficiency for NSAA incorporation because of the presence of release factor 1 (RF1). RF1 naturally binds the amber stop codon (TAG)[28] and prematurely terminates protein translation. Methods to counteract this competitive termination of the TAG stop codon include increasing the addition of competing tRNA[21], tagging and purifying out RF1[29], release factor engineering[30], and genomically recoding strains to remove RF1 and reassigning all occurrences to the synonymous TAA codon[31].

High-yield protein production with multiple-site incorporation of NSAAs still remains a critical challenge. As a result, optimized strains, protein production platforms, and methods for producing modified proteins containing NSAAs in high yields are needed.

SUMMARY OF THE INVENTION

The invention relates to genomically recoded organisms, platforms for preparing sequence defined biopolymers in vitro comprising a cellular extract from a genomically recoded organisms, and methods for preparing sequence defined biopolymers in vitro are described. In particular, the invention relates to genomically recoded organisms comprising a strain deficient in release factor 1 (RF-1) or a genetic homolog thereof and at least one of at least one additional genetic knock-out mutation, at least one additional upregulated gene product, or both at least one additional knock-out mutation and at least one additional upregulated gene product.

One aspect of the invention provides genomically recoded organism comprising a strain deficient in release factor 1 (RF-1) or a genetic homolog thereof and at least one of at least one additional genetic knock-out mutation, wherein the at least one additional genetic knock-out mutation improves DNA stability, RNA stability, protein stability, amino acid stability, energy supply, or any combination thereof; at least one additional upregulated gene product, wherein the at least one additional upregulated gene product improves energy supply, chaperone levels, translation function, ribosome recycling, or any combination thereof; or both the at least one additional genetic knock-out mutation and the at least one additional upregulated gene product. In some embodiments the genomically recoded organism may comprises an *E. coli* strain. In certain embodiments the genomically recoded organism the strain comprises *E. coli* strain C321.ΔprfA, *E. coli* strain rec13.ΔprfA, or a derivative of either *E. coli* strain C321.ΔprfA or *E. coli* strain rec13.ΔprfA. In certain embodiments, a cellular extract from the strain of the genomically recoded organism is capable of preparing a sequence defined biopolymer or a protein in greater yield and/or purity than a strain that is not deficient in release factor 1 (RF-1), does not have the at least one additional knock-out mutation, does not have the at least one additional upregulated gene product, or any combination thereof.

In some embodiments, the at least on additional genetic knock-out mutation comprises a gene selected from a group consisting of endA, mazF, rna, rnb, rne, gor, lon, ompT, gdhA, gshA, sdaA, sdaB, speA, WaaL, tnaA, glpK, and any combination thereof. In certain embodiments, the at least one additional genetic knock-out mutation comprises endA and a gene selected from the group consisting of mazF, rna, rnb, rne, gor, lon, ompT, gdhA, gshA, sdaA, sdaB, speA, WaaL, tnaA, glpK, and any combination thereof.

In some embodiments, the at least on additional upregulated gene product comprises a member selected from the group consisting of ackA, ndk, pykF, cdd, dsbC, dnaK, dnaJ, crpE, tig, groS, groL, infA, infB, fusA, efp, lepA, tufB, hslR, ffr, and any combination thereof. In certain embodiments, the at least on additional upregulated gene product improves chaperone levels or translation function.

In some embodiments, the genomically recoded organism further comprises T7 RNA polymerase expressed from a plasmid present in the genetically recoded organism or an integration site in the genome of the genetically recoded organism.

A second aspect of the invention provides a platform for preparing a sequence defined biopolymer or a protein in vitro, the platform comprising a cellular extract from a genomically recoded organism. In certain embodiments, a cellular extract from the strain of the genomically recoded organism is capable of preparing a sequence defined biopolymer or a protein in greater yield and/or purity than a strain that is not deficient in release factor 1 (RF-1), does not have the at least one additional knock-out mutation, does not have the at least one additional upregulated gene product, or any combination thereof. In certain embodiments, the cellular extract is an S12 extract, an S30 extract, or an S60 extract.

In some embodiments, the sequence defined biopolymer or protein comprises a product prepared from the platform that includes at least one unnatural amino acid. In certain embodiments, the sequence defined biopolymer or protein comprises a product prepared from the platform that includes a plurality of unnatural amino acids. In certain embodiments, the sequence defined biopolymer or protein comprises a product prepared from the platform that includes a at least 5 unnatural amino acids.

In some embodiments, the platform further comprises an orthogonal translation system component configured to incorporate unnatural amino acids. In certain embodiments, the orthogonal translation system component is expressed from a plasmid present in the genomically recoded organism, expressed from an integration site in the genome of the genetically recoded organism, co-expressed from both a plasmid present in the genomically recoded organism and an integration site in the genome of the genetically recoded organism, express in an in vitro transcription and translation reaction, or added exogenously.

In some embodiments, the platform further comprises T7 RNA polymerase. In certain embodiments, the T7 RNA polymerase is expressed from a plasmid present in the genetically recoded organism or an integration site in the genome of the genetically recoded organism.

In some embodiments, the cellular extract from the genomically recoded organism is a component in a reaction mixture.

An additional aspect of the invention is a method for cell-free protein synthesis of a sequence defined biopolymer or protein in vitro, the method comprising contacting a RNA template encoding the sequence defined biopolymer with a reaction mixture comprising a cellular extract from the genomically recoded organism. In some embodiments, a cellular extract from the strain of the genomically recoded organism is capable of preparing the sequence defined biopolymer or the protein is greater yield and/or purity than a strain that is not deficient in release factor 1 (RF-1), does not have the at least one additional knock-out mutation, does not have the at least one additional upregulated gene product, or any combination thereof. In certain embodiments, the cellular extract is an S12 extract, an S30 extract, or an S60 extract.

In some embodiments, the sequence defined biopolymer or protein comprises a product prepared from the method that includes at least one unnatural amino acid. In certain embodiments, the sequence defined biopolymer or protein comprises a product prepared from the method that includes a plurality of unnatural amino acids. In certain embodiments, the sequence defined biopolymer or protein comprises a product prepared from the platform that includes a at least 5 unnatural amino acids. In some embodiments, the sequence defined biopolymer encoded by the RNA template comprises at least 5 unnatural amino acids and a product prepared from the method includes at least 80% of the encoded unnatural amino acids. In some embodiments, the sequence defined biopolymer encoded by the RNA template comprises at least 5 unnatural amino acids and at least 80% of a plurality of products prepared from the method include 100% of the encoded unnatural amino acids. In certain embodiments at least 80% of a plurality of products prepared from the method are full length.

In some embodiments, the sequence defined biopolymer or protein encodes a therapeutic product, a diagnostic product, a biomaterial product, an adhesive product, a biocomposite product, or an agricultural product.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 3A shows optimization of plasmid DNA in CFPS reactions.

FIG. 3B shows optimization of T7 RNA polymerase in CFPS reactions.

FIG. 3C shows the effect of RNase inhibitor in CFPS reactions.

FIG. 12A shows optimization of pAcF incorporation into sfGFP with 5 TAG using lysates derived from C321.ΔA.759 harboring pEVOL-pAcF by optimizing levels of purified orthogonal synthetase (pAcFRS).

FIG. 12B shows optimization of pAcF incorporation into sfGFP with 5 TAG using lysates derived from C321.ΔA.759 harboring pEVOL-pAcF by optimizing levels of non-standard amino acid (pAcF).

FIG. 12C shows optimization of pAcF incorporation into sfGFP with 5 TAG using lysates derived from C321.ΔA.759 harboring pEVOL-pAcF by optimizing levels of orthogonal tRNA (o-tz-tRNA).

DETAILED DESCRIPTION

Figure 1:
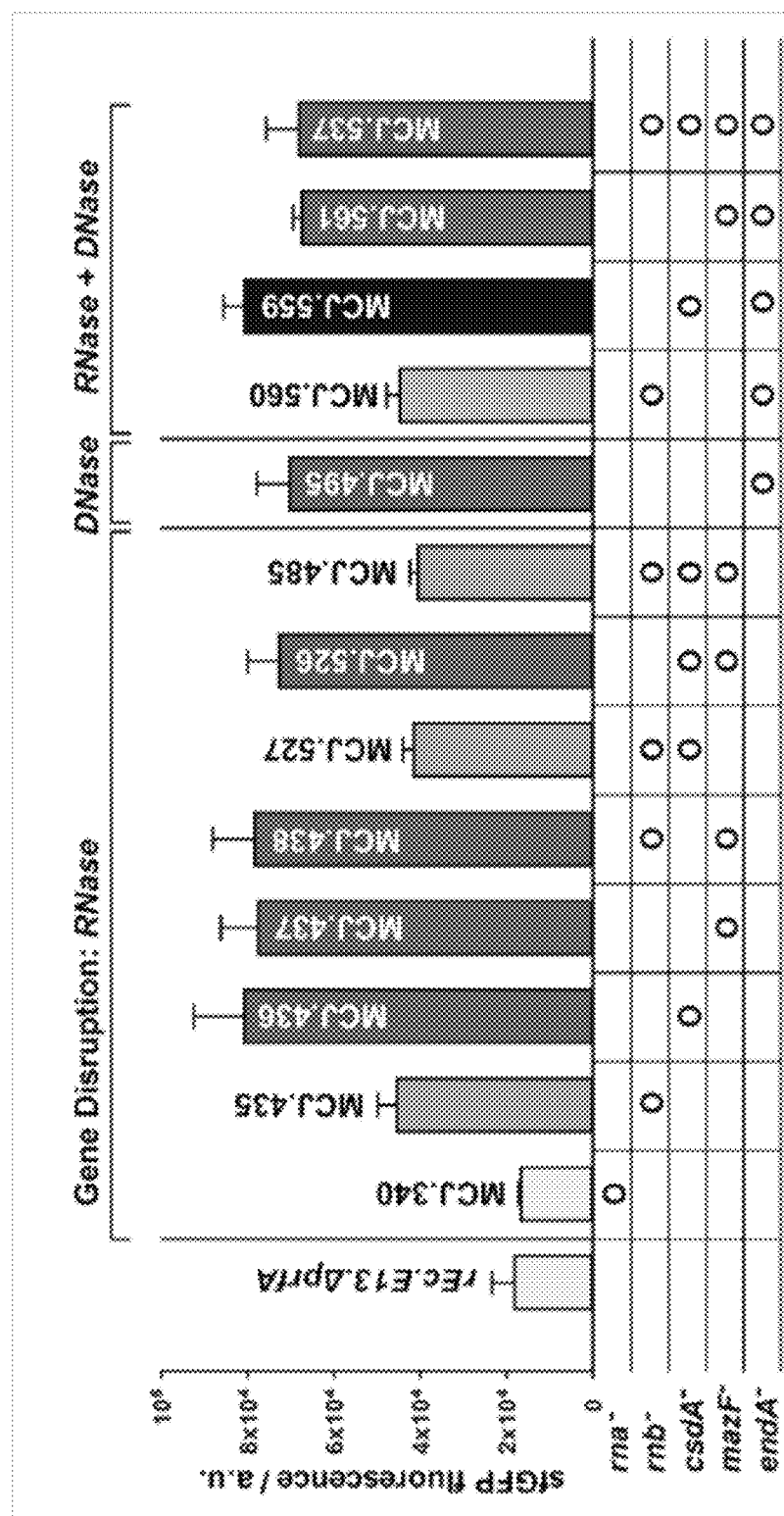
FIG. 1 shows a comparison of CFPS efficiency of different cell extracts. Active wild-type sfGFP was synthesized by using cell extracts derived from genomically recoded *E. coli* with single and multiple inactivation of nucleases.

Described herein are genomically recoded organisms (GROs), platforms for preparing sequence defined biopolymers in vitro comprising a cellular extract from a genomically recorded organisms, and methods for preparing sequence defined biopolymers in vitro. The GROs and platform described herein allow for multi-site NSAA incorporation into sequence defined biopolymers prepared in vitro at high yield and purity. The GRO has been optimized by genome engineering to improve extract performance by the incorporation of at least one additional genetic knock-out mutation, at least one additional upregulated gene product, or both at least one additional genetic knock-out mutation and at least one additional upregulated gene product. The use of a cellular extract from the GRO resulted in a surprisingly high yield for protein production. Moreover, the use of the cellular extract resulted in surprisingly high quantities of modified protein incorporating one or more NSAAs product at high purity. As will be described below, the production of sequence defined biopolymers or protein polymers with up to 40 NSAA incorporation at 95% purity may be achieved. Such an advance has never been shown before to our knowledge and surprisingly exceeds the state of the art by greater than 10 fold. Extracts produced from these genomically modified organisms show surprising promise for production of new-kinds of sequence defined biopolymers or proteins.

Terminology

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary range include from about 0.01 mM to about 5.0 mM; from about 0.1 mM to about 2.5 mM; and from about 2.0 mM to about 6.0 mM, among others.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target, "target sequence", "target region", and "target nucleic acid," as used herein, are synonymous and refer to a region or sequence of a nucleic acid which is to be amplified, sequenced, or detected.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation can also occur using exogenously-supplied expression template and polymerase from an orthogonal host organism different from the organism used to prepare the extract. In the case of an extract prepared from a yeast organism, an example of an exogenously-supplied expression template includes a translational open reading frame operably coupled a bacteriophage polymerase-specific promoter and an example of the polymerase from an orthogonal host organism includes the corresponding bacteriophage polymerase.

As used herein, Energy Charge (E.C.) refers to the overall status of energy availability in the system.

Energy Charge can be calculated by initially determining the concentrations of ATP, ADP and AMP in the extract as a function of time during Tx/Tl CFPS reaction. The Energy Charge of a control extract not used in a CFPS reaction can be used a reference state for the initial Energy Charge of a CFPS reaction. Alternatively, Energy Charge for a CFPS reaction can be assessed for a given extract prior to performing CFPS reaction with the extract (e.g., before adding a required reaction component, such as an expression template or a required polymerase).

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a DNA polymerase (most typically a thermostable DNA polymerase), dNTPs, and a divalent metal cation in a suitable buffer. A "CFPS reaction mixture" typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Genomically Recoded Organisms

An aspect of the present invention is a genomically recoded organism (GRO) comprising a strain deficient in release factor 1 (RF1) or a genetic homolog thereof and at least one additional genetic knock-out mutation, at least one additional upregulated gene product, or both at least one additional genetic knock-out mutation and at least one additional upregulated gene product. Surprisingly, a GRO comprising a strain deficient in RF1 or a genetic homolog thereof and at least on additional genetic knock-out mutation or at least one additional upregulated gene product can be used to produced cellular extracts for CFPS that lead to high-yield protein production as well as allow for the incorporation of a plurality of NSAAs in a sequence defined biopolymer in high quantities and in high purities.

GRO comprising a strain deficient in RF1 or a genetic homolog thereof may be prepared by any method of strain engineering. In certain embodiments the strain deficient in RF1 is prepared in which all instances of the UAG codon have been removed, permitting the deletion of release factor 1 (RF1; terminates translation at UAG and UAA) and, hence, eliminating translational termination at UAG codons. This GRO allows for the reintroduction of UAG codons, along with orthogonal translation machinery to permit efficient and site-specific incorporation of NSAAs into proteins. That is, UAG may be transformed from a nonsense codon (terminates translation) to a sense codon (incorporates amino acid of choice), provided the appropriate translation machinery is present.

The strain may comprise a prokaryote strain. In some embodiments, the strain is an E. coli strain. In certain specific embodiments, the strain is E. coli strain C321.ΔprfA, E. coli strain rec13.ΔprfA, or a derivative of either E. coli strain C321.ΔprfA or E. coli strain rec13.ΔprfA.

The GROs described herein have many surprisingly advantageous properties. The GROs described herein advantageously allow for the production of sequence defined biopolymers and/or proteins in high yield and/or purity. The GROs described herein allow for the incorporation of a plurality of unnatural amino acids in high yield and/or purity. The GROs described herein allow for the preparation of sequence defined biopolymers or proteins from RNA templates that are full length, i.e. truncated products are minimized. As a result, cellular extracts from the GROs described herein are capable of preparing the sequence defined biopolymer or the protein is greater yield and/or purity than a strain that (i) is not deficient in release factor 1 (RF-1), (ii) does not have the at least one additional knock-out mutation, (iii) does not have the at least one additional upregulated gene product, or (iv) any combination thereof.

Knock-out Mutations

In an aspect of the invention, the GRO comprising a strain deficient in RF1 or a genetic homolog thereof further comprises at least one additional genetic knock-out mutation. The at least one additional genetic knock-out mutation is preferably a knock-out mutation that downregulates or eliminates a negative protein effector for CFPS. In certain embodiments, the at least one additional genetic knock-out mutation improves DNA stability, RNA stability, protein stability, amino acid stability, energy supply, or any combination thereof. In certain embodiments, the at least one additional genetic knock-out mutation comprises 1, 2, 3, 4, or more than 4 genetic knock-out mutations. In embodiments where the strain comprises 2 or more genetic knock-out mutations, at least 2 of the genetic knock-out mutations may both improve the same attribute, improved DNA stability, improved RNA stability, improved protein stability, improved amino acid stability, improved energy supply, or may both improve different attributes.

To improve DNA or RNA stability, the at least one additional genetic knock-out mutation may target the functional inactivation of nucleases. In vivo, nucleases play important roles in regulating DNA and mRNA turnover. However, their presence in crude cell extracts is expected to be deleterious, leading to template instability and reaction termination. A nonexhaustive list of potential negative effectors follow. RNase A (encoded by ma) degrades RNA by catalyzing the cleavage of phosodiester bonds, and identification of strains (e.g., MRE600, A19) lacking ma was important for early studies in in vitro translation. RNase II (encoded by rnb) is responsible for mRNA decay by 3' to 5' exonuclease activity, and cell extracts lacking RNase II exhibit a 70% increase in CFPS efficiency. RNase E (encoded by me) is part of a cold shock degradosome that induces mRNA decay in cold shock, which the cells experience during harvest prior to extract generation. MazF (encoded by mazF) is a toxin that degrades mRNA by sequence-specific (ACA) endoribonuclease activity, which could affect transcript stability. CsdA (encoded by csdA) is part of a cold shock degradosome along with RNase E and induces mRNA decay in cold shock, which the cells experience during harvest prior to extract generation. DNA-specific endonuclease I (encoded by endA) breaks double-stranded DNA, and its deletion has previously shown to be important for extending the duration of CFPS reactions. These and other nucleases may be functionally inactivated by the at least on additional genetic knock-out mutation.

To improve protein stability, the at least one additional genetic knock-out mutation may target the functional inactivation of proteases. In vivo, these proteases play important roles in regulating protein turnover. However, their presence in CFPS reactions is expected to be deleterious, leading to protein instability issues. A nonexhaustive list of potential negative effectors follow. Glutathione reductase (encoded by gor) reduces oxidized glutathione to maintain a reducing environment in the cytoplasm of a cell, making synthesis of disulfide-bonded proteins problematic. Lon (encoded by lon) is an ATP-dependent protease that demonstrated improved protein production in cell-free systems in BL21 strains upon transcriptional down regulation. Outer membrane protease VII (encoded by ompT) demonstrates specificity for paired basic residues and has been shown to stabilize proteins during CFPS upon removal. These and other proteases may be functionally inactivated by the at least on additional genetic knock-out mutation.

The at least one additional genetic knock-out mutation may target proteins known to negatively affect amino acid or energy supply. In vivo, these proteins play important roles in metabolism and substrate turnover. However, their presence in crude cell extracts is expected to be deleterious, leading to decreased amino acid and energy supply to support translation. A nonexhaustive list of potential negative effectors follow. Glutamate dehydrogenase (encoded by gdhA) catalyzes the deamination of glutamate, which may affect glutamate's stability. Glutamate-cysteine-ligase (encoded by gshA) catalyzes the first step of glutathione synthesis and may decrease the stability of cysteine. Serine deaminase I (encoded by sdaA) and serine deaminase II (encoded by sdaB) are two of the three enzymes involved in serine degradation. Arginine decarboxylase (encoded by speA) consumes arginine in the biosynthetic production of putrescine. Tryptophanase (encoded by tnaA) consumes tryptophan in the production of indole. Lastly, glycerol kinase (encoded by glpK) consumes ATP to phosphorylate glycerol, which could help deplete the energy supply required for cell-free reactions. These and other proteins may be functionally inactivated by the at least on additional genetic knock-out mutation.

Strains having at least one additional genetic knock-out mutation, may be prepared by any method of engineering a strain to functionally inactivate the negative effector to lessen or eliminate the negative effector from a lysate prepared from the strain. In certain embodiments, the genetic knock-out mutations may be prepared by inserting either a nonsense mutation and/or a frameshift mutation into the genome of the strain as well as deleting a vital portion of a gene coding sequence. In certain embodiments, the genetic knock-out mutations may be prepared by removing regulatory sequences (i.e. promoter, ribosome binding site) or otherwise changing these sequences in the genome as to render them non-functional. In certain embodiments, negative effectors can be functionally knocked out in lysates by introducing a unique affinity tag and subsequently using the tag to selectively remove the effector protein from the lysates. In certain embodiments a strain having at least one additional genetic knock-out mutation may be prepared by multiplex automated genome engineering (MAGE),λ-Red recombinase-mediated recombination (Datsenko-Wanner), zinc-finger nucleases (ZFNs), transcription activator-like effector nucleases (TALENs), clustered regularly interspaced short palindromic repeats (CRISPR)-associated protein-9 nuclease (Cas9), and any other commonly used recombineering and genome engineering tools.

Upregulated Gene Products

In an aspect of the invention, the GRO comprising a strain deficient in RF1 or a genetic homolog thereof further comprises at least one additional upregulated gene product. In certain embodiments the GRO comprising a strain deficient in RF1 or a genetic homolog thereof further comprises at least one additional upregulated gene product and at least one additional genetic knock-out mutation. The at least one additional upregulated gene product is preferably an upregulated gene product that is a positive effector for CFPS. In certain embodiments, the at least one additional upregulated gene product improves energy supply, chaperone levels, translations function, ribosome recycling, or any combination thereof. In certain embodiments, the at least on additional upregulated gene product comprises 1, 2, 3, 4, or more than 4 upregulated gene products. In embodiments where the strain comprises 2 or more upregulated gene products, at least 2 of the upregulated gene products may both improve the same attribute, improved energy supply, improved chaperone levels, improved translation function, or improved ribosome recycling, or may both improve different attributes.

To improve energy supply, the at least one additional upregulated gene product may target the upregulation of kinases. In vivo, these proteins play important roles in metabolism and the transfer of phosphate groups. The upregulated presence in crude cell extracts is expected to improve energy supply to support translation. A nonexhaustive list of potential positive effectors follow. Acetate kinase (encoded by ackA) increases the overall metabolic flux of metabolites toward substrate-level ATP generation. Nucleoside-diphosphate kinase (encoded by ndk) facilitate the synthesis of NTPs from their corresponding NDPs. Pyruvate kinase monomer (encoded by pykF) helps drive ATP generation. These and other kinases may be the at least one additional upregulated gene product.

To improve energy supply, the at least one additional upregulated gene product may target the upregulate of deaminases. In vivo, these proteins may play important roles in metabolism and preparing metabolites. A nonexhaustive list of potential positive effectors follow. Cytidine deaminase (encoded by cdd) initiates the deamination of cytidine which may lead to the synthesis of UTP. These and other deaminases may be the at least one additional upregulated gene product To improve chaperone levels, the at least one upregulated gene product may target the upregulation of isomerases, foldases and/or holdases. In vivo, these proteins may play important roles in the assisting proteins to adopt functionally active conformations. The upregulated presence in crude cell extracts is expected to improve chaperone levels to support protein production into soluble and/or active confirmations. A nonexhaustive list of potential positive effectors follow. Disulfide bond isomerase (encoded by dsbC) shuffles disulfide bonds into correct positions. Chaperone protein DnaK (encoded by dnaK) aids the folding of nascent polypeptide chains and the rescue of misfolded proteins. Chaperone protein DnaJ (encoded by danJ) stimulates the ATPase activity of DnaK. Protein GrpE (encoded by grpE) stimulates the ATPas activity of DnaK. Trigger Factor (encoded by tig) aids the folding of nascent polypeptides. The 10 kDa chaperonin subunit (encoded by groS) forms part of the GroEL-GroES chaperonin complex that aids in protein folding. The 60 kDa chaperonin subunit (encoded by groL) forms part of the GroEL-GroES chaperonin complex that aids in protein folding. These and other isomerases, foldases, and/or holdases may be the at least one additional upregulated gene product To improve translation function, the at least one upregulated gene product may target the upregulation of initiation factors and/or elongation factors. In vivo, these proteins play important roles in the translation function. The upregulated presence in crude cell extracts is expected to improve translation function. A nonexhaustive list of potential positive effectors follow. Translation initiation factor IF-1 (encoded by infA) interacts with the 30S ribosomal subunit to initiate translations. Translation initiation faction IF-2 (encoded by infB) has a role in the proper placement of the charged initiator fMet-tRNA via a GTP-dependent mechanism. Elongations factor G (encoded by fusA) facilitates translocation of the ribosome by one codon along a mRNA. Elongation factor P (encoded by efp) stimulates the synthesis of peptide bonds. Elongation factor 4 (encoded by lepA) can alter the rate of translation, leading to increases in the rate of translation under certain stress conditions. Elongation factor TU 2 (encoded by tufB) helps shuttle charge tRNAs to ribosomes. These and other initiation factors and/or elongation factors may be the at least one additional upregulated gene product To improve translation function, the at least one upregulated gene product may target the upregulation of recycling factors. In vivo, these proteins play important roles in the ribosome recycling. The upregulated presence in crude cell extracts is expected to improve ribosome recycling. A nonexhaustive list of potential positive effectors follow. Heat shock protein 15 (encoded by hslR) is involved with the recycling of free 50S ribosomal subunits. Ribosome-recycling factor (encoded by frr) promotes rapid recycling of ribosomal subunits after the release of the polypeptide chain. These and other recycling factors may be the at least one additional upregulated gene product Strains having at least one additional genetic knock-out mutation, may be prepared by any method of engineering a strain to functionally increase a positive effector to increase the presence of the positive effector in the lysate prepared from the strain. In certain embodiments, the upregulated gene product is expressed from a plasmid present in the GRO and/or expressed from an integration site in GRO genome. Additionally, gene upregulation may be enhanced by engineering the promoter and/or ribosome binding site in front of your gene of interest located either on a plasmid or on the genome. A stronger promoter/ribosome binding site would lead to an increase in transcriptional activity. Techniques commonly employed to integrate a plasmid overexpressing a positive effector into a strain includes transformation. Techniques commonly employed to integrate a gene cassette containing a positive effector into the genome for overexpression includes λ-Red recombinase-mediated recombination (Datsenko-Wanner).

Platforms for Preparing Sequence Defined Biopolymers

An aspect of the invention is a platform for preparing a sequence defined biopolymer of protein in vitro. The platform for preparing a sequence defined polymer or protein in vitro comprises a cellular extract from the GRO organism as described above. Because CFPS exploits an ensemble of catalytic proteins prepared from the crude lysate of cells, the cell extract (whose composition is sensitive to growth media, lysis method, and processing conditions) is the most critical component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 20140295492 on Oct. 2, 2014, which is incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in Application No. PCT/US2015/033221 to Michael C. Jewett et al., entitled TETHERED RIBOSOMES AND METHODS OF MAKING AND USING THEREOF, filed 29 May 2015, which is incorporated by reference. In certain embodiments, one or more orthogonal components may be prepare in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture).

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., form about 15° C. to about 30° C., form about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Methods for Preparing Proteins and Sequence Defined Biopolymers

An aspect of the invention is a method for cell-free protein synthesis of a sequence defined biopolymer or protein in vitro. The method comprises contacting a RNA template encoding a sequence defined biopolymer with a reaction mixture comprising a cellular extract from a GRO as described above. Methods for cell-free protein synthesis of a sequence defined biopolymers have been described[1, 18, 26].

In certain embodiments, a sequence-defined biopolymer or protein comprises a product prepared by the method or the platform that includes an amino acids. In certain embodiments the amino acid may be a natural amino acid. As used herein a natural amino acid is a proteinogenic amino acid encoded directly by a codon of the universal genetic code. In certain embodiments the amino acid may be an unnatural amino acid. As used here an unnatural amino acid is a nonproteinogenic amino acid. An unnatural amino acids may also be referred to as a non-standard amino acids (NSAA). In certain embodiments, a sequence defined biopolymer or protein may comprise a plurality of unnatural amino acids. In certain specific embodiments, a sequence defined biopolymer or protein may comprise a plurality of the same unnatural amino acid. The sequence defined biopolymer or protein may comprise at least 5, at least 10, at least 15, at least 20, at least 25, at least 30, at least 35, or at least 40 or the same or different unnatural amino acids.

Examples of unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl) alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 24ufa24hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an $\alpha,\alpha$ disubstituted amino acid; a β-amino acid; a γ-amino acid, a cyclic amino acid other than proline or histidine, and an aromatic amino acid other than phenylalanine, tyrosine or tryptophan.

The methods described herein allow for preparation of sequence defined biopolymers or proteins with high fidelity to a RNA template. In other words, the methods described herein allow for the correct incorporation of unnatural amino acids as encoded by an RNA template. In certain embodiments, the sequence defined biopolymer encoded by a RNA template comprises at least 5, at least 10, at least 15, at least 20, at least 25, at least 30, at least 35, or at least 40 unnatural amino acids and a product prepared from the method includes at least 80%, at least 85%, at least 90%, at least 95%, or 100% of the encoded unnatural amino acids.

The methods described herein also allow for the preparation of a plurality of products prepared by the method. In certain embodiments, at least 80%, at least 85%, at least 90%, at least 95%, or at least 98% of a plurality of products prepared by the method are full length. In certain embodiments, the sequence defined biopolymer encoded by a RNA template comprises at least 5, at least 10, at least 15, at least 20, at least 25, at least 30, at least 35, or at least 40 unnatural amino acids and at least 80%, at least 85%, at least 90%, at least 95%, or at least 98% of a plurality of products prepared by the method include 100% of the encoded unnatural amino acids.

In certain embodiments, the sequence defined biopolymer or the protein encodes a therapeutic product, a diagnostic product, a biomaterial product, an adhesive product, a biocomposite product, or an agricultural product.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1

Methods of Making and Using RF1 Deficient rEc.E13.ΔprfA Strains for the Preparation of Proteins and Sequence-defined Biopolymers We engineered the rEc.E13.ΔprfA strain by disrupting the Rnase genes, both individually and in combinations, using MAGE. Specifically, we used MAGE oligos to introduce an internal stop signal (TAA codon) and frame shift mutation ~1-4 into the open reading frame of the target gene (TABLE 2). We generated single disruptions of ma, rnb, csdA, and mazF, as well as multiple disruptions of rnb, csdA, and mazF, in different combinations to create a series of Rnase mutants (TABLE 3). Gene disruptions were screened by multiplex allele-specific PCR that amplified PCR bands specific to each mutation and confirmed by DNA sequencing. We then measured growth rates for each of the MAGE-modified strains in 2×YTPG media (the medium used in preparation of cell lysates) to determine how the gene disruptions might affect cellular fitness. Growth rates of the strains with single or multiple disruptions of ma, rnb, csdA, and mazF were approximately ±25% relative to the strain rEc.E13.ΔprfA, with the exception of the rnb and mazF double disruption (MCJ.438), which displayed a significant growth defect.

Lysates from each engineered strain were tested in CFPS to assess their overall protein synthesis capability. For rapid screening, we prepared lysates from shake flask cultures and a syringe-based homogenization method. CFPS of sfGFP was carried out in 15 μL combined transcription-translation (TX-TL) reactions for 20 h at 30° C. The ma mutation was selected first because of its presence in the commonly used CFPS A19 and MRE600 source strains.[15] However, functional inactivation of ma (MCJ.340) in rEc.E13.ΔprfA did not impact wild-type sfGFP synthesis, as measured by fluorescence, when compared to the parent strain (FIG. 1). In contrast, single disruption of rnb, csdA, or mazF increased CFPS yields by two- to fourfold (FIG. 1). Next, we investigated the effect of disabling multiple Rnase genes together (rnb, csdA, and mazF) in CFPS. CFPS yields were not improved among those combinations of gene disruption and, in fact, decreased in some cases (MCJ.527 and MCJ.485; FIG. 1). Taken together, our results show that inactivation of Rnase II, CsdA, and MazF are beneficial for CFPS.

Figure 2A:
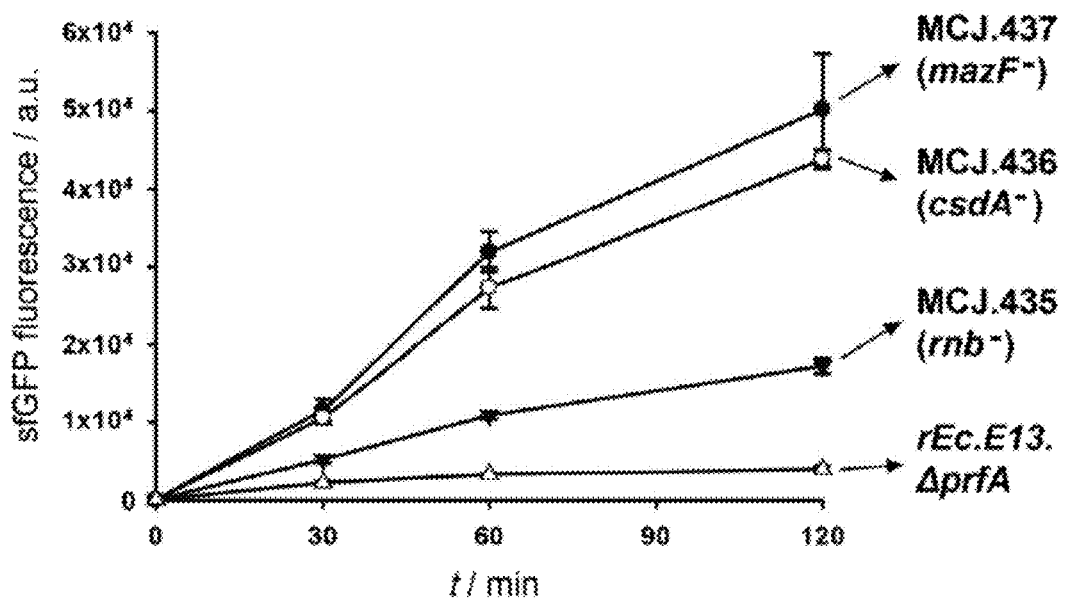
FIG. 2A shows cell-free translation (TL)-only reactions of wild-type sfGFP from purified mRNA in different single RNase-deficient cell extracts.

We carried out cell-free TL-only reactions for 120 min at 30° C., priming the reaction with purified mRNA template from the sfGFP gene (600 ng per 15 μL reaction), as opposed to DNA template. Without the ability to replenish mRNA from T7 RNA polymerase, as was possible in combined TX-TL experiments used above (FIG. 1), we could now observe the impact of the genomic changes on RNA stability. For this analysis, we specifically focused on extracts from the single gene disruption strains: MCJ.435(rnb-), MCJ.436(csdA-), and MCJ.437(mazF-). As compared to the extract from the parent strain (rEc.E13.ΔprfA), disruption of mazF, csdA, and rnb increased cell-free translation 13-, 11-, and four-fold, respectively (FIG. 2A). In addition to quantifying sfGFP synthesis by cell-free TL-only reactions in lysates from different genomically modified strains, we also examined the mRNA degradation profiles by incubating 1800 ng of purified sfGFP mRNA in the cell-free reaction. As expected, mRNA levels were maintained at higher levels in extracts from Rnase-deficient strains. Specifically, more than ~60% of sfGFP mRNA remained after 120 min incubation with the extracts from single disruption of mazF or csdA, whereas 16% remained with rnb disruption, and mRNA levels in the parent extract derived from rEc.E13.ΔprfA were entirely degraded. These results were consistent with the TX-TL reactions (FIG. 1) and indicate that inactivating Rnases from the lysate source strain reduces mRNA degradation and, in turn, improves CFPS.

We next investigated the effects of disrupting the DNA-specific endonuclease I (MCJ.495). It has previously been observed that an endA deletion strain exhibits increased plasmid DNA production in vivo, [44] but its role was not clear in vitro, as the endA deletion was previously assessed only in combination with recCBD deletion.[10] In CFPS reactions performed with extracts from source strains lacking endonuclease I (MCJ.495), we observed a greater than fourfold increase in sfGFP synthesis compared to that of rEc.E13.ΔprfA (FIG. 1).

Figure 2B:
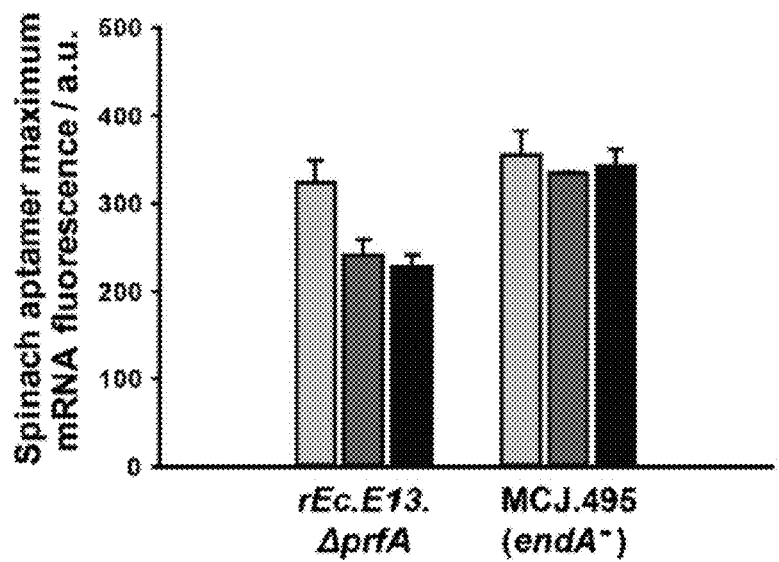
FIG. 2B shows cell-free Spinach aptamer synthesis by using endonuclease I-deficient (MCJ.495) and -present (rEc.E13.ΔprfA) extracts. After pre-incubation (0 min light grey, 60 min medium grey, 180 min black) of Spinach aptamer plasmid DNA with cell extract, CFPS reagents were added and incubated.

We hypothesized that the improved CFPS yields were a result of plasmid DNA stability. To test this hypothesis, we directly incubated plasmid DNA in the extract alone and monitored plasmid DNA stability by gel electrophoresis. We did not detect differences in plasmid DNA concentrations when comparing extracts with or without endonuclease I; however, our results could be confounded by the fact that Dnase activity can be inhibited in cell extracts.[45] Thus, we tried an alternative approach that better mimicked our CFPS conditions. The key idea was to pre-incubate plasmid DNA with extracts from strains with or without endonuclease I, followed by CFPS (FIG. 2B). If the DNA template was degraded during pre-incubation, or the transcription reaction was inhibited by endonuclease I in some way, less mRNA would be synthesized, which in turn could be responsible for higher CFPS yields when endA was disabled. Plasmid DNA containing the mRFP1-Spinach aptamer gene (TABLE 3) was pre-incubated with cell extract and a fluorophore molecule, 3,5-difluoro-4-hydroxybenzylidene imidazolinone (DFHBI), for 0, 60, and 180 min. Then, mRNA was synthesized upon addition of CFPS reagents and quantified by measuring the fluorescence of DFHBI-bound Spinach aptamer mRNA.[46] Similar levels of Spinach aptamer mRNA were synthesized in MCJ.495 (endA-) extracts before and after the pre-incubation. In contrast, the extract with endonuclease I (rEc.E13.ΔprfA) decreased the maximum mRNA synthesis level by 25% after pre-incubation (FIG. 2B). These results support the hypothesis that endA disruption improves CFPS by helping stabilize the DNA template. As inactivating endonuclease I was beneficial for CFPS, we subsequently applied MAGE to create a variety of endA- and Rnase-disrupted strains (TABLE 3).

We then carried out a series of optimization experiments to see if the genomically modified source strains provided unique benefits for CFPS or if yield improvements could have simply been achieved by optimization of reaction conditions using the original host (rEc.E13.ΔprfA). For this analysis, we selected the MCJ.559 (csdA-endA-) strain, which had the highest CFPS yields (FIG. 1). We specifically explored the impact of altering the DNA plasmid concentration, changing the T7 RNA polymerase concentration, and adding Rnase inhibitor in CFPS reactions with lysates derived from strain MCJ.559 and the parent. Increasing the concentrations of plasmid DNA (FIG. 3A) or T7 RNA polymerase (FIG. 3B) with the parent rEc.E13.ΔprfA extract did not improve sfGFP synthesis. In fact, CFPS yields decreased. Furthermore, the current concentrations of plasmid DNA (13.3 ngµL$^{-1}$) and T7 RNA polymerase (0.1 µgµL$^{-1}$) used in this study were already optimal, as similar trends were obtained in the extract from MCJ.559 (FIGS. 3A-B). Addition of Rnase inhibitor to CFPS reactions also did not improve protein synthesis (FIG. 3C). Together, our data indicates that the improvement of CFPS comes from the nuclease disruptions and is not achievable by simply adjusting the initial cell-free components.

We also confirmed that the mutations generated by MAGE were not reverted. After 250 generations of the MCJ.559 strain in a rich medium, the cell growth rate was similar (within 4%) compared to the strain before 250 generations, the extract performance was the same, and mutations of prfA, csdA, and endA were preserved, as confirmed by PCR for all three and DNA sequencing for csdA and endA disruption. These results highlight that the MAGE gene disruption approach is robust and stable on time horizons that would be associated with a seed train in the laboratory.

With CFPS improvements from engineered strains in hand, we assessed NSAA incorporation in extracts from our best strain. To do so, we first prepared crude extract from the MCJ.559 strain grown in a 10 L fermenter, which provides exquisite control over growth conditions.[47] In this case, o-tRNA was constitutively expressed during the cell growth as previously reported.[22] As a positive control, we then tested wild-type sfGFP synthesis in a cell-free reaction by using the fermenter-prepared extract. We obtained 660±40 µgµL$^{-1}$ of wild-type sfGFP, which was similar to the yields obtained with extract prepared from a shake flask. For NSAA incorporation, we quantitatively tested the incorporation of p-acetyl-1-phenylalanine (pAcF) into sfGFP with an in-frame amber codon at single and multiple positions (TABLE 3). The necessary components of the orthogonal translation system (OTS) were also added. Specifically, we added 10 µgµL$^{-1}$ linear DNA of optimized o-tRNA (o-tRNA$^{opt}$) in the cell-free reaction for in situ synthesis of additional o-tRNA (i.e., beyond that overexpressed in the source strain).[35, 21] The orthogonal pAcF-tRNA synthetase (pAcFRS) was overproduced, purified as previously described,[35] and added at a level of 0.5 µgµL$^{-1}$ in the cell-free reaction. The NSAA, pAcF, was supplied at a level of 2 mM in each CFPS reaction.

Figure 4A:
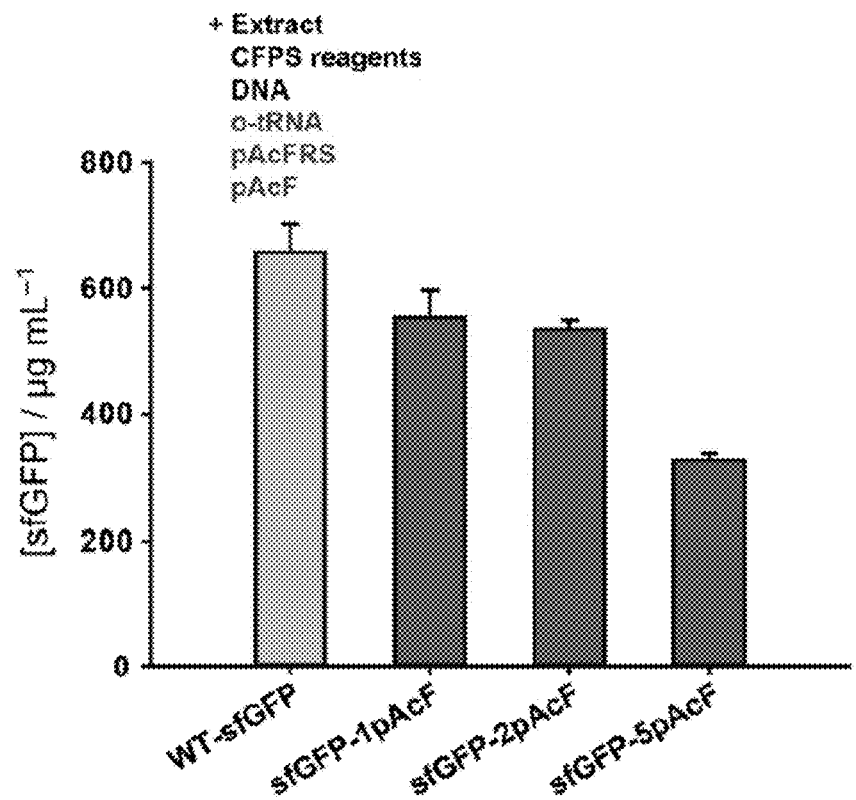
FIG. 4A shows yields of active wild-type sfGFP (WT-sfGFP) and modified sfGFP proteins containing one, two, and five pAcFs.
Figure 4B:
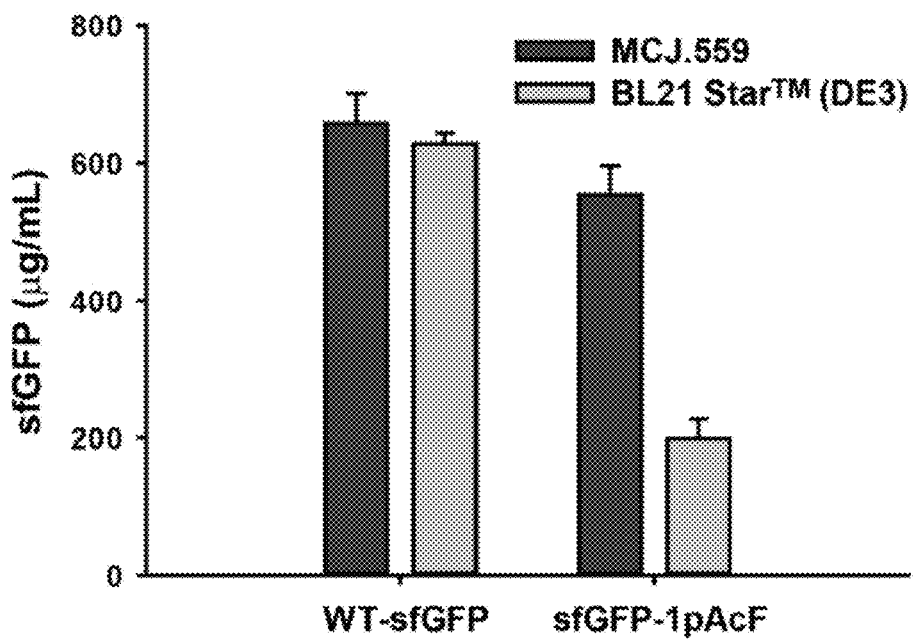
FIG. 4B shows cell extract performance comparison between MCJ.559 and BL21 Star™ (DE3) extract.

We synthesized 550±40 µgµL$^{-1}$ of modified sfGFP containing a single pAcF, which represents a ~84% yield as compared to wild-type sfGFP production (FIG. 4A). In addition, we obtained a 540±20 µgµL$^{-1}$ yield for modified protein synthesis for two pAcF incorporations (81% yield) and 330±10 µgµL$^{-1}$ for five pAcF incorporations (50% yield; FIG. 4A). These results represent a threefold improvement in modified sfGFP synthesis as compared to our previous work on rEc.E13.ΔprfA extract,[35] as well as more than a tenfold higher protein expression titer (in gL$^{-1}$) compared to recent in vivo NSAA incorporation into GFP. [30, 48] Furthermore, the modified protein synthesis titer was ~2.8 times higher in MCJ.559 extracts than those from aBL21 Star (DE3) extract which contains RF1, whereas the wild-type sfGFP synthesis was similar with both extracts (FIG. 4B). Thus, the MAGE-improved MCJ.559 extract significantly increased the synthesis of proteins containing NSAAs.

Figure 5:
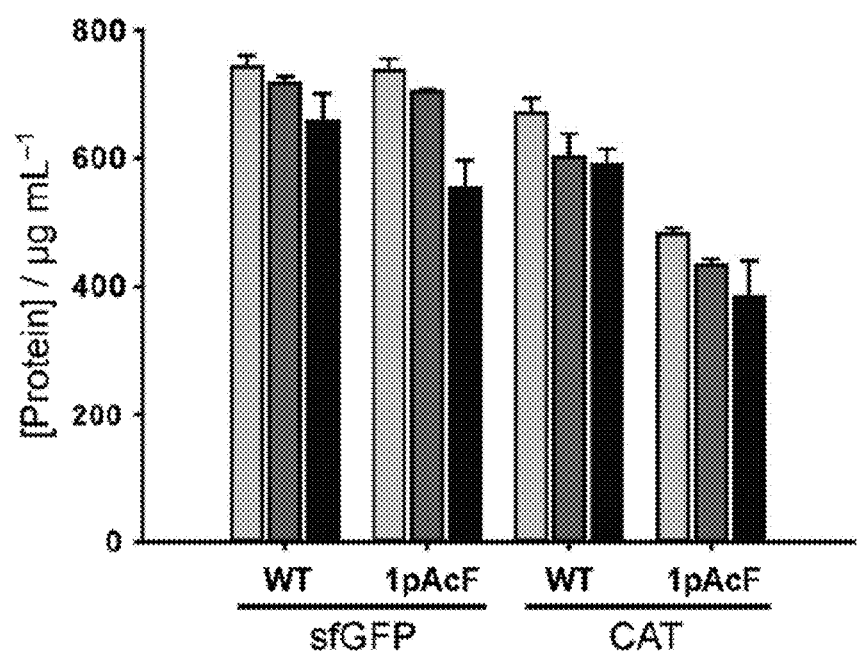
FIG. 5 shows comparison of total (light grey), soluble (medium grey), and active (black) protein yields of sfGFP and CAT with and without single pAcF.

We then carried out top-down mass spectrometry (i.e., MS analysis of whole intact proteins) to detect and provide semi-quantitative information for the incorporation of pAcF into sfGFP. The spectrum of the 32+ charge state of sfGFP and illustrates mass shifts corresponding to the incorporation of one, two, and five pAcF residues. Site-specific incorporation of pAcF, as detected by MS, was greater than 95% in all samples, with less than 3 ppm difference between experimental and theoretical protein masses (TABLE 1). In other words, we achieved efficient, high yielding, and pure site-specific pAcF incorporation into sfGFP. To demonstrate that our observations were not limited to sfGFP, we also examined pAcF incorporation into chloramphenicol acetyl transferase (CAT). Active CAT containing pAcF was synthesized at titers of 380±60 µgµL$^{-1}$, with a ~65% yield of wild-type protein production (FIG. 5). Hence, the MAGE-enhanced extract provides the synthesis of soluble and active proteins containing pAcF, like wild-type proteins, and may be applied for different types of protein production.

TABLE 1

Monoisotopic masses calculated from mass spectrometric date.

| sfGFP species | Mass (Da, exp.) | Mass (Da, th.) | Error (ppm) | Shift from WT-sfGRP (Da, exp.) | Shift from WT-sfGRP (Da, th.) |
|---|---|---|---|---|---|
| WT-sfGFP | 26847.50 | 26847.45 | 2.6 | — | — |
| sfGFP-1pAcF (T216) | 26935.54 | 26935.48 | 2.2 | 88.04 | 88.03 |
| sfGFP-2pAcF (N212, T216) | 27010.56 | 27010.52 | 1.5 | 163.06 | 163.07 |
| sfGFP-5pAcF (D36, K101, E132, D190, E213) | 27176.66 | 27176.76 | 1.8 | 329.16 | 329.16 |

"Exp." Indicates experimentally obtained masses and "Th." Indicates theoretically calculated masses.

Figure 6:
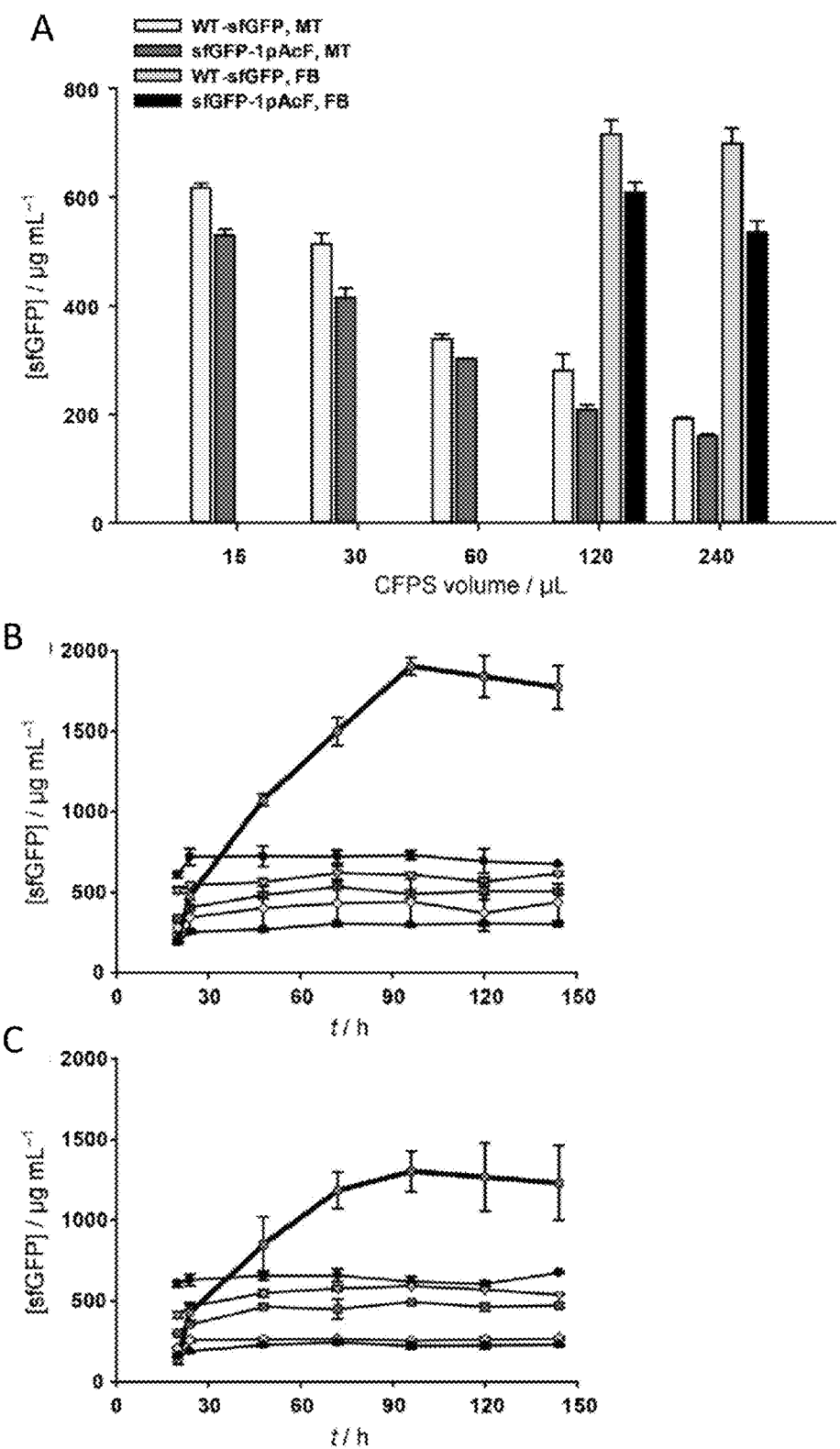
FIG. 6A shows production of wild-type sfGFP (WT-sfGFP) and modified sfGFP with pAcF (sfGFP-1pAcF) in different reaction volumes by using a microcentrifuge tube (MT) and a flat-bottom24-wellplate (FB).
FIG. 6B shows time course semicontinuous and batch CFPS for WT-sfGFP and. Batches were of 15 (circle), 30 (downward triangle), 60 (square), 120 (diamond), and 240 µL (upward triangle).
FIG. 6C shows time course semicontinuous and batch CFPS for sfGFP-1pAcF. Batches were of 15 (circle), 30 (downward triangle), 60 (square), 120 (diamond), and 240 µL (upward triangle).

We then set out to demonstrate the potential for scale-up in CFPS reactions that incorporate NSAAs into proteins. Specifically, we tested the effect of increasing the CFPS reaction volume in both a microcentrifuge tube and a flat-bottom 24-well plate. By increasing the reaction volume from 15 to 240 mL, the efficiency of wild-type sfGFP production significantly decreased in the microcentrifuge tube, whereas the same reactions in the flat-bottom 24-well plate did not decrease the protein yields (FIG. 6). We observed similar results for the synthesis of modified protein (FIG. 6). Our results are consistent with those of Voloshin and Swartz, who reported these phenomena previously; specifically, the impact of surface-area-to-volume ratios on CFPS yields.[49] In order to confirm that the decrease in production yield was not specific to active GFP formation (i.e., chromophore maturation), we measured total and soluble sfGFP production by radioactive [14C]Leu incorporation, which counts all synthesized sfGFP protein. Total and soluble sfGFP synthesis was decreased as reaction volume was increased. This is consistent with our observations for active sfGFP synthesis (FIG. 6). We next assessed incubation time to see if the reduced CFPS yield as a function of increasing reaction volume was recovered by increasing incubation time. This was not the case. After 24 h, sfGFP production in all batch reactions was saturated and did not increase with further incubation time (FIG. 6B). Modified sfGFP containing single pAcF showed similar results (FIG. 6C). Our results indicate that CFPS with RF1-deficient MCJ.559 extract is scalable when accounting for surface-area-to-volume effects.

We then applied semicontinuous CFPS[50-51] using a microdialysis device (3.5K MWCO) to increase sfGFP production yield. In semicontinuous reactions, substrates and byproducts passively diffuse between the CFPS reaction and a substrate reservoir to sustain small molecule concentrations necessary to keep the reaction active. With a semicontinuous setup, wild-type sfGFP and modified sfGFP production were continually increased until 96 h, yielding titers of about 1900±50 and 1300±100 µgµL$^{-1}$, respectively (FIG. 6B-C). We expect that these titers could be improved further if the external substrate reservoir was exchanged or the extract condensed That said, the modified protein titer from a semicontinuous CFPS setup was >20 times higher than those recently observed in cells on a gram per liter basis.[30, 48] Taken together, our results indicate that the yield was significantly improved by using a semicontinuous reaction setup.

Materials and Methods

Strains and plasmids: The bacterial strains and plasmids used in this study are listed in Table X2. Spectinomycin (20 µg mL$^{-1}$) was used for culturing strains, kanamycin (50 µg mL$^{-1}$) was used for maintaining pY71-based plasmids, and tetracycline (20 µg mL$^{-1}$) was used for maintaining the pDULE-o-tRNA plasmid.

Strain construction and verification: The strains in this study were generated from rEc.E13.ΔprfA[31] by disrupting genes of interest with mutagenic oligonucleotides by MAGE [52] (TABLE 2). Cultures were grown in lysogeny broth (LB)-Lennox medium (10 gL$^{-1}$ tryptone, 5 gL$^{-1}$ yeast extract, and 5 gL$^{-1}$ NaCl)[16] at 32° C. and 250 rpm throughout MAGE cycling steps. MAGE oligonucleotides were designed to introduce an internal stop codon and frameshift of ~1=4 into the target gene sequence, thereby causing early translational termination as previously reported.[52] Single, double, triple, and quadruple disruptions of csdA, rnb, mazF, and endA, including single rna disruption, were generated to investigate the effect of their inactivation on CFPS (TABLE 3). Multiplex allele-specific colony PCR was performed to verify gene disruptions[32] by using wild-type forward (-wt-F) or mutant forward (-mut-F) primers and reverse primers (-R; TABLE 2). Wild-type and mutant forward primers were identical except at the 3'-ends of the oligonucleotides, and the reverse primers were used for detection of both wild-type and mutant alleles. The mutant allele could be amplified by using the mutant forward and reverse primer set (-mut-F and -R) but not the wild-type forward and reverse primer set (-wt-F and -R). MASC PCR was performed in 20 mL reactions by using a multiplex PCR kit (Qiagen) at 95 8 C for 15 min, with 30 cycles of 94 8 C for 30 s, 65 8 C for 30 s, and 72 8 C for 1 min, and a final extension of 72 8 C for 5 min. Mutant alleles were screened by running PCR products on a 2% agarose gel and confirmed by DNA sequencing by using sequencing primers (TABLE 2).

TABLE 2

Primers used for MAGE, MASC PCR, and DNA sequencing. Underlined text indicates mismatch and frameshift insertion. Four bases at 5'-MAGE oligo were phosphorilated (*).

| Primer Name | Primer Sequnce (5' → 3') | SEQ ID. |
|---|---|---|
| MAGE | | |
| rna | G*C*T*G*ATTTTCTGACCGTACATGGTC TGTGGCCAGGAATGTAAATGCTGATGTAT TGCCTAAATCGGTTGCTGCCCGTGGTGTT GATGAAC | 1 |
| csdaA | G*C*T*C*TGGCTGATGTCAGGACGGGTA GTCACGCTTCAGTTAAATGCGCACTTCCT GCGGCTCTTTCATAAAGCGGCGGGTAATG CGACGA | 2 |
| rnb | A*T*T*T*TGTCACCATCGACAGTGCCAG CACAGAAGATATGGATTAACTGACTTTTC GCTAAGGCGTTGCCGGATGACAAACTTCA GCTGAT | 3 |
| maz | T*T*G*A*TTGCGTTGTACAAGGAACACA CAGACACATACCTGTTTTGTTGTTTCAGT TAGAAAGGACTCAGGACAACAGCTGGACG ATGTCC | 4 |
| endA | C*G*G*T*AAAAGTCCACGCTGACGCGCC CGGTACGTTTTATTGCTAACTGAAAAATT AACTGGCAGGGCAAAAAAGGCGTTGTTGA TCTGCA | 5 |
| ompT | T*G*G*A*CAACTCTCGGCAGCCGAGGTG GCAATATGGTCGCGCAGGACTGGATGGAT TCCAGTAACCCCGGAACCTGGACGGATGA AAGTAGA | 6 |
| lon | A*A*C*T*CTGCTTCCGCTTTCTCTTTTG CCTCTTTCGGCATCTTTCAGTTAGTCGAT TTTGCGCTTCAGGGCTTCGTTTTCGTCCG GCGCGT | 7 |
| gor | G*T*T*T*TGATACCACTATCAATAAATT CAACTGGGAAACGTTGTAACTGAAGCCGT ACCGCCTATATCGACCGTATTCATACTTC CTATGA | 8 |
| gdhA | T*G*C*G*CTTCCATCCGTCAGTTAACCT TTCCATTCTCAAATTCTAACTGATTTGAA CAAACCTTCAAAAATGCCCTGACTACTCT GCCGA | 9 |
| sdaA | T*C*T*A*CAGCAAAACTTATTATTCCAT CGGCGGCGGTTTTATCTAACTGAGAAGAA CACTTTGGTCAGGATGCTGCCAACGAAGT AAGCGT | 10 |
| sdaB | A*C*A*G*CCAGACTTACTACTCTATTGG CGGTGGCTTTATCGTTTAACTGAGAGCAT TTTGGCCAGCAGGATAGCGCACCGGTTGA AGTTCC | 11 |
| speA | A*T*C*T*TCTCAATGACCAGATAGACCT TGTGCCCATCTTCTCTCAGTTATAATGC CAGGCGGATATATTCGCGGTCTTTATAAC CGTTGC | 12 |
| gshA | G*A*T*G*CACCAAACAGATAAGGAATGA CCCAACCGAAACGATATCAGTTAGCGGAT AACGCGGAAATAGCCCGCAGAAATTTTCT CTTTGG | 13 |
| tnaA | A*C*C*T*TGAGGGATTAGAACGCGGTAT TGAAGAAGTTGGTCCGTAACTGAGTGCCG TATATCGTTGCAACCATCACCAGTAACTC TGCAGG | 14 |

TABLE 2-continued

Primers used for MAGE, MASC PCR, and DNA sequencing. Underlined text indicates mismatch and frameshift insertion. Four bases at 5'-MAGE oligo were phosphorilated (*).

| Primer Name | Primer Sequnce (5' → 3') | SEQ ID. |
|---|---|---|
| glpK | G*C*A*C*CAAAGTGAAGTGGATCCTCGACCATGTGGAAGGCTCTTAACTGACGTGCACGTCGTGGTGAATTGCTGTTTGGTACGGTTGATAC | 15 |
| MASC PCR | | |
| rna-wt-F | GTACATGGTCTGTGGCCAGGATTGC | 16 |
| rna-mut-F | GGCCAGGAATGTAAATGCTGATGTA | 17 |
| rna-R | TGGCATGACTTCACTTAGTTTAGC | 18 |
| csdA-wt-F | GCCGCAGGAAGTGCGCATTCAGTCC | 19 |
| csdA-mut-F | GCCGCAGGAAGTGCGCATTTAACTGA | 20 |
| csda-R | CAGTGCGCGGTATTGATCCAGATCGC | 21 |
| rnb-wt-F | CCAGCACAGAAGATATGGATGACGCC | 22 |
| rnb-mut-F | CCAGCACAGAAGATATGGATTAACTGA | 23 |
| rnb-F | TCACTTTCAGGCTGCCAGTCACCGG | 24 |
| mazF-wt-F | CTGTTGTCCTGAGTCCTTTCATGTAC | 25 |
| mazF-mut-F | CTGTTGTCCTGAGTCCTTTCTAACTGA | 26 |
| mazF-R | GGCTTTAATGAGTTGTAATTCCTCTG | 27 |
| endA-wt-F | CCCGGTACGTTTTATTGCGGATGT | 28 |
| endA-mut-F | CCCGGTACGTTTTATTGCTAACTGA | 29 |
| endA-R | GCTGGCGCTGGTAATTTCGGCGTCA | 30 |
| ompT-wt-F | CAGCCGAGGTGGCAATATGGTCGAT | 31 |
| ompT-mut-F | CAGCCGAGGTGGCAATATGGTCGCG | 32 |
| ompT-R | GAGTTCAAAATCTTCATAACGATAAC | 33 |
| lon-wt-F | CTGAAGCGCAAAATCGACGCGGCG | 34 |
| lon-mut-F | CTGAAGCGCAAAATCGACTAACTGA | 35 |
| lon-R | AGCGGGTTTTTCACGCCCACTTTCGC | 36 |
| gor-wt-F | TTCAACTGGGAAACGTTGATCGCC | 37 |
| gor-mut-F | TTCAACTGGGAAACGTTGTAACTGA | 38 |
| gor-R | TGCAACATTTCGTCCATACCAAAGC | 39 |
| gdhA-wt-F | CCTTTCCATTCTCAAATTCCTCGGC | 40 |
| gdhA-mut-F | CCTTTCCATTCTCAAATTCTAACTGA | 41 |
| gdhA-R | CTGCCGCCAAATGAAAGGCCCTTAC | 42 |
| sdaA-wt-F | ATCGGCGGCGGTTTTATCGTCGAT | 43 |
| sdaA-mut-F | ATCGGCGGCGGTTTTATCTAACTGA | 44 |
| sdaA-R | CAAGACCCGCAGCAGCCATTGAACAG | 45 |
| sdaB-wt-F | GGCGGTGGCTTTATCGTTGATGAA | 46 |
| sdaB-mut-F | GGCGGTGGCTTTATCGTTTAACTGA | 47 |
| sdaB-R | TACCTGTCCGGCGACCGGGTCACAC | 48 |
| speA-wt-F | GAATATATCCGCCTGGCATTAATTGGC | 49 |
| speA-mut-F | GAATATATCCGCCTGGCATTATAACTGA | 50 |
| speA-R | CGGTGATTACCGTCGGATGCGGCAG | 51 |
| gshA-wt-F | TATTTCCGCGTTATCCGCAATTAC | 52 |
| gshA-mut-F | TATTTCCGCGTTATCCGCTAACTGA | 53 |
| gshA-R | AAATCCTCTTCGCGCAGAATTTCCAGC | 54 |
| tnaA-wt-F | GGTATTGAAGAAGTTGGTCCGAATAAC | 55 |
| tnaA-mut-F | GGTATTGAAGAAGTTGGTCCGTAACTGA | 56 |
| tnaA-R | CTACCGCCAGACGCTCCATCGCGCC | 57 |
| glpK-wt-F | GACCATGTGGAAGGCTCTCGCGAG | 58 |
| glpK-mut-F | GACCATGTGGAAGGCTCTTAACTGA | 59 |
| glpK-R | CAAACAGCGCGGCCTGCTGGTCACC | 60 |
| prfA deletion confirmation | | |
| prfA-F | TGATCTGCAAAGCATCATTTCG | 61 |
| prfA-R | TTGCCTCACGTAACCAGTGTTGATA | 62 |
| prf-R2 | CATAACGGCTGTACATACGGAACAG | 63 |
| CAT plasmid construction | | |
| pY71-F | GGGCGTAAGTCGACCGGCTGCTA | 64 |
| pY71-R | TTCTCCATATGTATATCTCCTTCTTAAAGTT | 65 |
| CAT-F | ATATACATATGGAGAAAAAAATCACTGG | 66 |
| CAT-R | CGGTCGACTTACGCCCCGCCCTG | 67 |
| DNA Sequencing | | |
| rna-seq-F | GTTTCTCTGCTTCCCTTCTCTTCT | 68 |
| csdA-seqF | CTGCTGGACCACCTGAAACGTGGCA | 69 |
| rnb-seq-F | CTGAAAGGCGATCGTTCTTTCTATG | 70 |
| mazF-seq-F | GTAAAGAGCCCGTATTTACGCTTGC | 71 |
| endA-seq-F | ATGTACCGTTATTTGTCTATTGCTGC | 72 |
| ompT-seq-F | CTGACAACCCCTATTGCGATCAGCTC | 73 |
| lon-seq-F | GTGCTGGTGCGTACTGCAATCAGCC | 74 |
| gor-seq-F | TAAACACTATGATTACATCGCCATC | 75 |
| gdhA-seq-F | GCAAGCCGTTCGTGAAGTAATGACC | 76 |
| sdaA-seq-F | TACTCGCGTTGCCGTGGACGTTTATG | 77 |
| sdaB-seq-F | TGACCCGCGTGGTGGTTGACGTGTAC | 78 |
| speA-seq-F | GTGAAAACTCGTGAAGCACAGGGCC | 79 |
| gshA-seq-F | GAACATATGCTGACCTTTATGCGCG | 80 |

TABLE 2-continued

Primers used for MAGE, MASC PCR, and DNA sequencing. Underlined text indicates mismatch and frameshift insertion. Four bases at 5'-MAGE oligo were phosphorilated (*).

| Primer Name | Primer Sequnce (5' → 3') | SEQ ID. |
|---|---|---|
| tnaA-seq-F | CGTAGCTACTATGCGTTAGCCGAG | 81 |
| glpK-seq-F | AGGTTGGGTAGAACACGACCCAATG | 82 |
| mRNA stability | | |
| T7-pro-F | TCGATCCCGCGAAATTAATACGACTCACTATAGG | 83 |
| T7-ter-R | CAAAAAACCCCTCAAGACCCGTTTA | 84 |
| Orthogonal rRNA amplification | | |
| T7tRNA500-F | CCGAAGGTAACTGGCTTCAGCAGAG | 85 |
| T7tRNAopt-R | TGGTCCGGCGGAGGGGATTTGAACCCCTG | 86 |
| ELP CLONING | | |
| flst-NdeI-F | CACTATGCTTAAGGTACTCATATG | 87 |
| flst-SalI-R | CGATCTCCACTAGATGTCGAC | 88 |
| TS-BlpI-R | TAGTTATTGCTCAGCGGTGG | 89 |
| TS-ApaI-F | GTCCCGGGTTATGGGCCC | 90 |
| TS-NotI-F | GTTCATGTCTTCGCGGCCGCA | 91 |
| FI-KpnIApaI-f | GGTCGCGGGGTTGGGCCCAGCAAAGGTGAAGAACTGTTTACCG | 92 |
| FI-KpnIApaI-r | TTTGCTCATGGTACCATCTCCTTCTTAAAGTTAAACAAAATTATTTC | 93 |
| GBLOCK DNA SEQUENCE | | |
| gB-FlSt | CACTATGCTTAAGGTACTCATATGGATTACAAGGATCATGACGGTGATTACAAGGATCATGACATTGATTACAAGGATGACGACGATAAGTACCATGGACCTGCAATAGTTCCGGGCTAGGGCGTTCGTTCCGGGTGTAGGTGTTCATGTCTTCGCGGCCGCATGGAGCCATCCGCAGTTCGAAAAATAAGTCGACATCTAGTGGAGATCG | 94 |
| gB-Twin-Strep-NotIBlpI | GTTCATGTCTTCGCGGCCGCATCGGCGTGGAGCCACCCGCAGTTCGAGAAAGGTGGAGGTTCCGGAGGTGGATCGGGAGGTTCGGCGTGGAGCCACCCGCAGTTCGAAAAATAATAAGTCGACCGGCTGCTAACAAAGCCCGAAAGGAAGCTGAGTTGGCTGCTGCCACCGCTGAGCAATAACTA | 95 |
| gB-Twin-Strep-ApaIBlpI | GTCCCGGGTTATGGGCCCTCGGCGTGGAGCCACCCGCAGTTCGAGAAAGGTGGAGGTTCCGGAGGTGGATCGGGAGGTTCGGCGTGGAGCCACCCGCAGTTCGAAAAATAATAAGTCGACCGGCTGCTAACAAAGCCCGAAAGGAAGCTGAGTTGGCTGCTGCCACCGCTGAGCAATAACTA | 96 |

TABLE 3

Strains and Plasmids.

| Strain/Plasmide | Genotype/relevant characteristics | Source |
|---|---|---|
| STRAINS | | |
| EcNR2 | MG1655 with λ-prophage::bioA/bioB and cmR::mutS | [52] |
| BL21 (DE3) | fhuA2 [lon] ompT gal (λ DE3) [dcm] ΔhsdS λ DE3 = λ sBamHIo ΔEcoRI-B int:⊗ lacI::PlacUV5::T7 gene1) i21 Δnin5 | New England Biolabs |
| BL21 Star™ (DE3) | F- ompT hsdSB (rB-mB-) gal dcm rne131 (DE3) | Life Technologies |
| rEc.E13.ΔprfA (rec13. ΔprfA) | ΔprfA Ω Sp$^R$, Ap$^R$, Cm$^R$, EcNR2 derivative with 13 TAG termination reassigned to TAA at coaD, I, hemA, mreC, murF, lolA, lpxK, yaff, pfpA, sucB, fabH, fliN, and atpE | [8] |
| MCJ.340 | rEc.E13.ΔprfA rna- | |
| MCJ.435 | rEc.E13.ΔprfA rnb- | |
| MCJ.436 | rEc.E13.ΔprfA csdA- | |
| MCJ.437 | rEc.E13.ΔprfA mazF- | |
| MCJ.495 | rEc.E13.ΔprfA endA- | |
| MCJ.438 | rEc.E13.ΔprfA rnb- mazF- | |
| MCJ.527 | rEc.E13.ΔprfA csdA- rnb- | |
| MCJ.526 | rEc.E13.ΔprfA csdA- mazF- | |
| MCJ.560 | rEc.E13.ΔprfA rnb- endA- | |
| MCJ.559 | rEc.E13.ΔprfA csdA- endA- | |
| MCJ.561 | rEc.E13.ΔprfA mazF- endA- | |
| MCJ.485 | rEc.E13.ΔprfA csdA- rnb- mazF- | |
| MCJ.537 | rEc.E13.ΔprfA csdA- rnb- mazF- endA- | |
| C321.ΔA (C321.ΔprfA) | ΔprfA Ω Cb$^R$, Zeo$^R$, EcNR2 derivative with all 321 TAG termination codons reassigned to TAA | [31] |
| C321.ΔA.540 | C321.ΔA. rnb- | |
| C321.ΔA.541 | C321.ΔA. mazF- | |
| C321.ΔA.542 | C321.ΔA. endA- | |
| C321.ΔA.598 | C321.ΔA. rna- | |
| C321.ΔA.618 | C321.ΔA. ompT- | |
| C321.ΔA.620 | C321.ΔA. glpK- | |

TABLE 3-continued

Strains and Plasmids.

| Strain/Plasmide | Genotype/relevant characteristics | Source |
|---|---|---|
| C321.ΔA.626 | C321.ΔA. gshA⁻ | |
| C321.ΔA.628 | C321.ΔA. tnaA⁻ | |
| C321.ΔA.644 | C321.ΔA. gdhA⁻ | |
| C321.ΔA.666 | C321.ΔA. gor⁻ | |
| C321.ΔA.667 | C321.ΔA. lon⁻ | |
| C321.ΔA.668 | C321.ΔA. rne⁻ | |
| C321.ΔA.669 | C321.ΔA. sdaA⁻ | |
| C321.ΔA.672 | C321.ΔA. sdaB⁻ | |
| C321.ΔA.674 | C321.ΔA. speA⁻ | |
| C321.ΔA.544 | C321.ΔA. endA⁻ mazF⁻ | |
| C321.ΔA.678 | C321.ΔA. endA⁻ glpK⁻ | |
| C321.ΔA.679 | C321.ΔA. endA⁻ tnaA⁻ | |
| C321.ΔA.709 | C321.ΔA. endA⁻ gor⁻ | |
| C321.ΔA.711 | C321.ΔA. endA⁻ rne⁻ | |
| C321.ΔA.708 | C321.ΔA. endA⁻ lon⁻ | |
| C321.ΔA.703 | C321.ΔA. endA⁻ gor⁻ glpK⁻ | |
| C321.ΔA.705 | C321.ΔA. endA⁻ gor⁻ rne⁻ | |
| C321.ΔA.706 | C321.ΔA. endA⁻ gor⁻ tnaA⁻ | |
| C321.ΔA.740 | C321.ΔA. endA⁻ gor⁻ mazF⁻ | |
| C321.ΔA.738 | C321.ΔA. endA⁻ gor⁻ lon⁻ | |
| C321.ΔA.759 | C321.ΔA. endA⁻ gor⁻ rne⁻ mazF⁻ | |
| PLASMIDS | | |
| pY71-sfGFP | KmR, PT7::super folder gfp (sfGFP), C-terminal strep-tag | [22] |
| pY71-sfGFP-T216amb | pY71-sfGFP with amber codon at T216 | [22] |
| pY71-sfGFP-2amb | pY71-sfGFP with amber codon at N212 and T216 | [35] |
| pY71-sfGFP-5amb | pY71-sfGFP with amber codon at D36, K101, E132, D190, and E213 | [35] |
| pY71-CAT | KmR, PT7::CAT (chloramphenicol acetyl transferase) | [8] |
| pY71-CAT-D112amb | pY71-CAT with amber codon at D122 | [8] |
| pK7-catGM-CSF | $Km^R$, $P_{T7}$::modified murine ganulocyte-macrophage colony-stimulating factor (catGM-CSF) | [53] |
| pK7-DHFR | $Km^R$, $P_{T7}$::dihydrofolate reductase (DHFR) | New England Biolabs |
| pY71-pAcFRS | PT7::pAcFRS, C-terminal 6x histidine tag | [35] |
| pY71-pPaFRS | $P_{T7}$::pPaFRS, C-terminal 6x histidine tag | [22] |
| pDAK-pAzFRS | $P_{T7}$::pAzFRS, C-terminal 6x histidine tag | |
| pY71-mRFP1-Spinach | PT7::mRFP1-Spinach aptamer | [54] |
| pDULE-o-tRNA | Plpp::o-tRNA, $Tet^R$ | [22] |
| pY71-T7-tz-o-tRNA$^{opt}$ | PT7:: hammer-head ribozyme, o-tRNA$^{opt}$ | [35] |
| pEVOL-pAcF | $Cm^R$, $P_{glnS}$::pAcFRS, $P_{araBAD}$::pAcFRS, $P_{proK}$::o-tRNA | [28] |
| pY71-FlSt | N-ter Flagtag and C-ter Streptag | |
| pY71-ELP8 | ELP-8mer | |
| pY71-ELP16 | ELP-16mer | |
| pY71-ELP24 | ELP-24mer | |
| pY71-ELP32 | ELP-32mer | |
| pY71-ELP40 | ELP-40mer | |
| pY71-ELP48 | ELP-48mer | |
| pY71-ELP56 | ELP-56mer | |
| pY71-ELP64 | ELP-64mer | |
| pY71-sELP8 | sELP-8mer with 8 amber sites | |
| pY71-sELP16 | sELP-16mer with 16 amber sites | |
| pY71-sELP24 | sELP-24mer with 24 amber sites | |
| pY71-sELP32 | sELP-32mer with 32 amber sites | |
| pY71-sELP40 | sELP-40mer with 40 amber sites | |
| pY71-sELP48 | sELP-48mer with 48 amber sites | |
| pY71-sELP56 | sELP-56mer with 56 amber sites | |
| pY71-sELP64 | sELP-64mer with 64 amber sites | |
| pY71-mELP8 | mELP-8mer with 32 amber sites | |
| pY71-mELP16 | mELP-16mer with 64 amber sites | |
| pY71-ELP8-TS | ELP-8mer with Twin-Streptag | |
| pY71-ELP16-TS | ELP-16mer with Twin-Streptag | |
| pY71-sELP8-TS | sELP-8mer with 8 amber sites, Twin-Streptag | |
| pY71-sELP16-TS | sELP-16mer with 16 amber sites, Twin-Streptag | |
| pY71-mELP8-TS | mELP-8mer with 32 amber sites, Twin-Streptag | |
| pY71-mELP16-TS | mELP-16mer with 64 amber sites, Twin-Streptag | |
| pY71-KA-sfGFP | N-ter KpnI and C-ter ApaI restriction site addition on sfGFP | |
| pY71-FI-ELP30 | FI-ELP-30mer | |
| pY71-FI-ELP40 | FI-ELP-40mer | |
| pY71-FI-ELP30X | FI-ELP-30mer with 30 amber sites | |
| pY71-FI-ELP40X | FI-ELP-40mer with 40 amber sites | |

TABLE 3-continued

Strains and Plasmids.

| Strain/Plasmide | Genotype/relevant characteristics | Source |
|---|---|---|
| pY71-FI-ELP30-TS | FI-ELP-30mer with Twin-Streptag | |
| pY71-FI-ELP40-TS | FI-ELP-40mer with Twin-Streptag | |
| pY71-FI-ELP30X-TS | FI-ELP-30mer with 30 amber sites, Twin-Streptag | |
| pY71-FI-ELP40X-TS | FI-ELP-40mer with 40 amber sites, Twin-Streptag | |

$Km^R$, $Sp^R$, $Ap^R$, $Zeo^R$ and $Cm^R$ are kanamycin, spectinomycin, ampicillin, zeocin, and chloramphenicol resistance, respectively. 'Δ' indicates deleted gene, and superscript '−' indicates disabled gene via MAGE.

Growth rate assessment: Overnight cultures of engineered strains grown in LB[37] at 250 rpm and 34° C. were diluted to an $OD_{600}$ of 0.05 in 2×YTPG medium (16 $gL^{-1}$ tryptone, 10 $gL^{-1}$ yeast extract, 5 $gL^{-1}$ NaCl, 7 $gL^{-1}$ K2HPO4, 3 $gL^{-1}$ KH2PO4, and 18 $gL^{-1}$ glucose; adjusted to pH 7.2 with KOH). Diluted cultures (100 µL) were added to 96-well polystyrene plates (Costar 3370; Corning Incorporated, Corning, N.Y., USA). The $OD_{600}$ was measured at 15 min intervals for 15 h at 34° C. in fast shaking mode on a Synergy2 plate reader (Biotek, Winooski, Vt.). Growth data for each strain was obtained from six replicate wells with two independent cultures. Doubling time was calculated during the early exponential growth phase ($OD_{600}$=0.05-0.2).

Cell extract preparation: Cells were grown to an $OD_{600}$ of 4.0 in 2×YTPG medium (2 L) in Tunair shake flasks (1 L culture in each 2.5 L flask) at 34° C. and 220 rpm for rapid prototyping of engineered strains. In order to maintain pH~7, KOH (1 mL, 1 n) was added at OD600=2.0. For the MCJ.559 strain harboring pDULE-o-tRNA, the best CFPS performer, cells were grown in 2×YTPG medium (10 L) in a BIOSTAT C-plus fermenter (Sartorious AG, Gçt-tingen, Germany) to an $OD_{600}$ of 3.0 at 34° C. Cells were pelleted by centrifuging for 15 min at 5000 g and 4° C., washed with cold S30 buffer (3×10 mM tris.acetate pH 8.2, 14 mM magnesium acetate, 60 mM potassium acetate, 1 mM dithiothreitol),[38] and stored at −80° C. To make cell extract, cell pellets were thawed and suspended in S30 buffer (0.8-1 mL per gram of cells) and lysed in an EmulsiFlex-C3 homogenizer (Avestin, Ottawa, Canada) with a single pass at a pressure of ~138-172 MPa. A chilled syringe was used to inject resuspended cells and collect lysed cells for the small volume of cell suspension prepared from shake flasks, and a chilled hopper was used for the cells harvested from fermentation. Cell debris and insoluble components were removed by two rounds of centrifugation for 30 min at 30 000 g and 4° C. The supernatant was incubated for 80 min at 120 rpm and 37° C. in an empty run-off reaction to optimize the extract activity and then centrifuged for 15 min at 15 000 g at 4° C. The supernatant was flash-frozen in liquid nitrogen and stored at −80° C. until use. The total protein concentration of the extracts was 40-50 mg $mL^{-1}$, as measured by Quick-Start Bradford protein assay kits (Bio-Rad).

Purification of His-tagged pAcF-tRNA synthetase: BL21 (DE3) harboring pY71-pAcFRS[35] was grown in LB (1 L) to an $OD_{600}$ of 1.0 at 220 rpm and 37° C. pAcF-tRNA synthetase (pAcFRS) was produced by adding isopropyl-b-d-thiogalactopyranoside (IPTG; 0.2 mM, Sigma-Aldrich) for 3 h. Cells were harvested at 5000 g for 30 min at 4° C., washed with S30 buffer, and stored at −80° C. The frozen cell pellet was thawed in loading buffer (300 mM NaCl, 10 mM imidazole, 50 mM $NaH_2PO_4$, 5 mM Tris-HCl, pH 8.0),[20] lysed by using a homogenizer at ~138-172 MPa, and centrifuged at 16,000 g and 4 8° C. for 30 min. pAcFRS was purified on a 5 mL Ni-NTA column in a Bio-Logic DuoFlow FPLC system (Bio-Rad). The purified pAcFRS in the elution buffer (300 mM NaCl, 250 mM imidazole, 50 mM $NaH_2PO_4$, 5 mM Tris.HCl, pH 8.0)[20] was washed three times with S30 buffer by using an Amicon Ultracel YM-30 centrifugal filter and stored at −80° C. by adding an equal volume of 80% glycerol. The concentration of purified pAcFRS was quantified by Bradford assay.

CFPS reaction: CFPS reactions were performed to evaluate incorporation of pAcF by using a modified PANOx-SP system.[2] Briefly, a 15 µL CFPS reaction in a 1.5 mL microcentrifuge tube was prepared by mixing the following components: ATP (1.2 mM); GTP, UTP, and CTP (0.85 mM each); folinic acid (34.0 µg $mL^{-1}$); E. coli tRNA mixture (170.0 µg $mL^{-1}$); plasmid (13.3 µg $mL^{-1}$); T7 RNA polymerase (100 µg $mL^{-1}$); 20 standard amino acids (2 mM each); nicotinamide adenine dinucleotide (NAD; 0.33 mM); coenzyme-A (0.27 mM); spermidine (1.5 mM); putrescine (1 mM); sodium oxalate (4 mM); potassium glutamate (130 mM); ammonium glutamate (10 mM); magnesium glutamate (12 mM); phosphoenolpyruvate (PEP; 33 mM), and cell extract (27% v/v). For NSAA incorporation, pAcF (2 mM), pAcFRS (0.5 µg $mL^{-1}$), and linear DNA of o-tRNAopt (10 µg $mL^{-1}$) were additionally added. Linear DNA of o-tRNAopt was amplified from pY71-T7-tz-o-tRNAopt plasmid and transcribed during the cell-free reaction.[35] Furthermore, the o-tRNA was ex-pressed in the source strain during the extract preparation.[35] Each CFPS reaction was incubated for 20 h at 30° C. unless noted otherwise. When adding RNase inhibitor, 1 µL (4 U) of inhibitor (Qiagen) was added into the 15 µL cell-free reaction as per the manufacturer's suggestion.

Quantification of active sfGFP: Active full-length sfGFP protein yields were quantified by measuring fluorescence using a Synergy2 plate reader with $\lambda_{ex}$=485 nm, $\lambda_{em}$=528 nm, and cut-off at 510 nm in 96-well half-area black plates (Costar 3694; Corning Incorporated), and the fluorescence units were converted into concentrations by using a standard curve as previously described.[35]

Radioactive[14C] Leu assay: Total and soluble protein yields were quantified by determining radioactive[14C]Leu incorporation by using trichloroacetic acid (TCA).[38] Radioactivity of TCA-precipitated samples was measured by liquid scintillation counting (MicroBeta2; PerkinElmer).

mRNA stability assay: The sfGFP gene was PCR-amplified from the pY71 vector with T7-pro-F and T7-ter-R primers against the T7 promoter and the T7 terminator sequences (TABLE 2). The PCR-amplified linear template was then purified by using a PCR clean-up kit (Promega) and subsequently used as a template for in vitro transcription reactions according to the manufacturer's manual (Ribo-MAX Large Scale RNA Production System, Promega). The final concentration of mRNA was 1.8 µg $mL^{-1}$. In order to track mRNA stability in our extracts, we replaced the plasmid sfGFP with the mRNA of sfGFP (1800 ng) in the CFPS reaction. For direct measurement of mRNA degradation, 5 µL samples were taken from CFPS reactions during incubation at 30° C. and mixed with equal volumes of RNA protect Bacteria Reagent (Qiagen, Valencia, Calif.) and brought to 100 µL with RNase free water. All samples were then purified by using an RNeasy Mini total RNA purification kit (Qiagen) according to the manufacturer's manual. Purified mRNA was visualized on a 2% formaldehyde agarose gel stained with GelRed (Biotium, Hay-ward, CA, USA).

DNA stability assay: We used pY71-mRFP1-Spinach plasmid (TABLE 2) to track DNA stability. A preincubation mixture containing 4 mL of cell extract, 12.96 ng$\mu$L$^{-1}$ of pY71-mRFP1-Spinach plasmid,[51] and 6 nM of 3,5-difluoro-4-hydroxybenzylidene imidazolinone (DFHBI; Lucema, New York, N.Y., USA) was prepared on ice to minimize degradation of plasmid, and then incubated for 0, 60, and 180 min at 30° C. CFPS reaction components were added immediately after the preincubation step, and fluorescence of the Spinach aptamer binding to DFHBI was monitored for 180 min by using a CFX96 real-time (RT) PCR module installed on a C1000 Touch Thermal Cycler (Bio-Rad). The excitation and emission wavelengths of the fluorophore were 450-490 nm and 515-530 nm, respectively. The highest fluorescence was detected after 1 h incubation in the RT-PCR machine. For direct assessment of DNA degradation, 15 µL of plasmid DNA and extract mixture was prepared that contained 1 µg of pY71-sfGFP plasmid, 4 µL of extracts from the MCJ.495 or rEc.E13.∆prfA strain, and 3 µL of S30 buffer. After incubation at 30° C. for 0, 15, 30, and 60 min, samples were flash frozen in liquid nitrogen and stored at −20° C. To remove RNA, 100 µL of RNaseA-containing solution I from an E.Z.N.A. Miniprep kit (Omega Bio-Tek, Norcross, Ga., USA) was added to the sample and incubated for 20 min at room temperature, then 200 µL of water was added. Proteins were precipitated by the same volume of phenol/chloroform/isoamyl alcohol (25:24:1) solution, and the plasmid was purified by using a DNA Clean &Concentrator kit (Zymo Research, Irvine, Calif., USA). The purified plasmid was digested with BamHI at 37° C. for 90 min to be linearized and was visualized on a 0.7% agarose gel.

Full-length sfGFP purification and mass spectrometry: To confirm pAcF incorporation at corresponding amber sites, semi-quantitative mass spectrometry (MS) analysis was performed on purified sfGFP with pAcF putatively incorporated. First, full-length sfGFP was purified from CFPS reactions by using C-terminal strep-tags and 0.2 mL gravity-flow Strep-Tactin Sepharose mini-columns (IBA GmbH, Gottingen, Germany) and concentrated by using Microcon YM-10 centrifugal filter columns (Millipore). The purified sfGFP protein was then analyzed by nanocapillary LC-MS using a 100 mm×75 µm IDPLRP-S column in line with an Orbitrap Elite (ThermoFisher). All MS methods included the following events: 1) FT scan, m/z 400-2000, 120000 resolving power and 2) data-dependent MS/MS on the top two peaks in each spectrum from scan event 1 by using higher-energy collisional dissociation (HCD) with normalized collision energy of 25, isolation width 15 m/z, and detection of ions with resolving power of 60000. All data were analyzed by using QualBrowser, part of the Xcalibur software packaged with the ThermoFisher Orbitrap Elite (ThermoFisher). Smaller peaks to the right of the colored peaks ($\Delta m$=+16 Da) are due to oxidation of the protein—a common electrochemical reaction occurring during electrospray ionization. To remove non-covalent salt and water adducts from intact proteins (in this case, sfGFP), a small level of in-source collision energy (15 eV) was applied. As a result, water loss events from the intact sfGFP ($\Delta m$=−18 Da) were detected at minor levels to the left of the major peak.

CAT plasmid construction: Gibson assembly was used for seam-less construction of plasmids.[55] The wild-type chloramphenicol acetyl transferase (CAT) gene was amplified from pK7CAT[56] by using CAT-F an—-R primers (TABLE 2), and the pY71 plasmid backbone was amplified from pY71-sfGFP by using pY71-F an—-R primers (TABLE 2). Both PCR products were cleaned and mixed with Gibson assembly reactants as previously described[55] and incubated at 50° C. for 60 min to construct the pY71-CAT plasmid (TABLE 3). Likewise, CAT-D112Amb, with a single amber site corresponding to Asp112,[57] was amplified from pREP-CMD112 to construct the pY71-CAT-D112amb plasmid (TABLE 3).

CAT activity assay: Active CAT production was quantified by determining the enzymatic activity of CAT. Cell-free reaction sample (100× diluted, 2 µL) was added to reagent mix (178 µL) containing acetyl-CoA (20 µL, 1 mM) and 5,5'-dithio-bis(2-nitrobenzoic acid) (DTNB; 20 µL, 4 mg mL$^{-1}$). After incubation at 37° C. for 15 min, chloramphenicol (20 µL, 1 mM) was added, and the solution was immediately mixed. The increase in $A_{412\ nm}$ over approximately 5 min was recorded by using the Synergy2 plate reader, and $\Delta A_{412\ nm}$ min$^{-1}$ was calculated. CAT activity of the cell-free synthesized sample was quantified by comparison to CAT standard activity (C8413, Sigma-Aldrich).

Scaled-up CFPS: Cell-free reaction volumes were increased from 15 to 240 µL in Axygen 1.5 mL polypropylene microcentrifuge tubes (MCT-150-C; Corning, Union City, Calif., USA) and a flat-bottom 24-well polystyrene plate (353226; BD Biosciences, San Jose, Calif., USA). There was appreciable volume loss due to evaporation in CFPS reactions with volumes less than 100 µL in the flat-bottom 24-well plate; thus, 120 and 240 µL reactions were tested. By filling the outer chambers surrounding the wells with water, which humidified the air, negligible sample evaporation was achieved. Reactions were performed at 30° C. for 20 h.

Semicontinuous cell-free reaction: Cell-free reactions (120 µL) were carried out in a microdialysis device (3.5 K MWCO) in a Pierce 96-well Microdialysis Plate (Thermo Fisher Scientific).[51] The micro-dialysis device interfaces with 1500 µL of dialysis buffer that contains CFPS reagents as described in the "CFPS reaction" section without T7 RNA polymerase, plasmid, cell extract, o-tRNAopt, or pAcFRS. Time course reactions were monitored at 30° C. for 144 h.

Example 2

Figure 7:
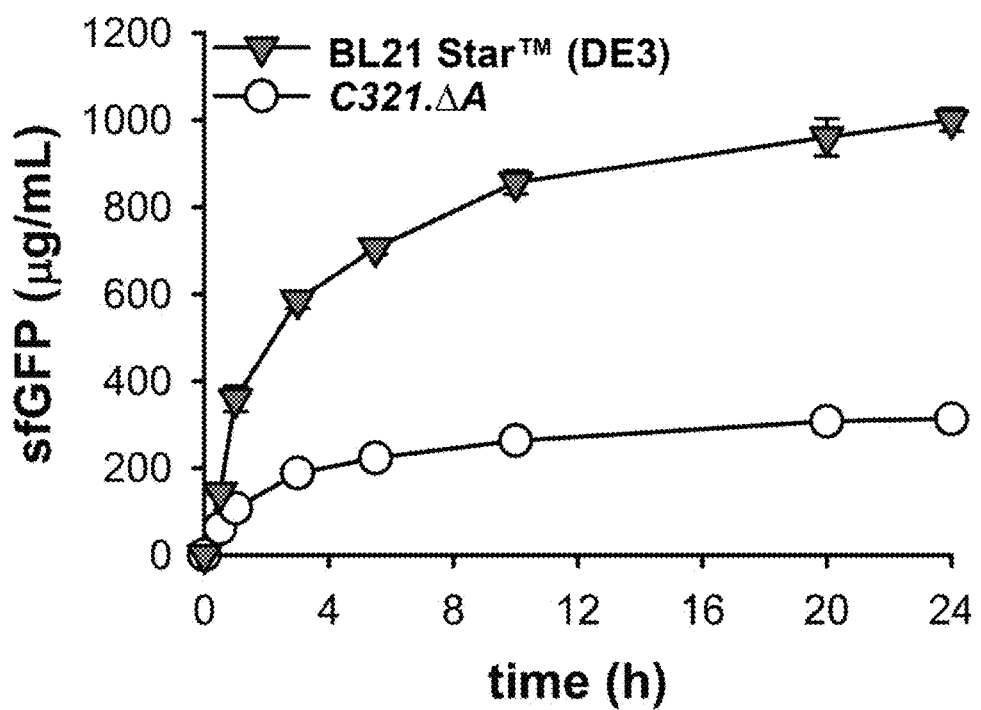
FIG. 7 shows time-course of superfolder green fluorescent protein (sfGFP) synthesis using extracts derived from a commercial strain, BL21 Star™ (DE3), and the genomically recoded organism, C321.ΔA.

Methods of Making and Using RF1 Deficient C321.∆A Strains for the Preparation of Proteins and Sequence-defined Biopolymers The genomically recoded organism, C321.∆A, has been utilized for the synthesis of proteins with NSAAs and is ideal for multi-site incorporation due to the lack of RF1. In efforts to utilize this strain for cell-free synthesis of proteins containing NSAAs, we first wanted to gauge the maximal production of protein in a standard cell-free environment. The activity of lysate generated from C321.∆A was compared in a time course expression test alongside the current cell-free, state-of-the-art expression system derived from BL21 Star™ (DE3) (FIG. 7). Reactions were run for 24 h at 30° C. in batch mode. Not surprisingly, C321.∆A protein yields were 3.2-fold lower at 24 h likely because protein expression had not been previously optimized for CFPS.

Figure 8A:
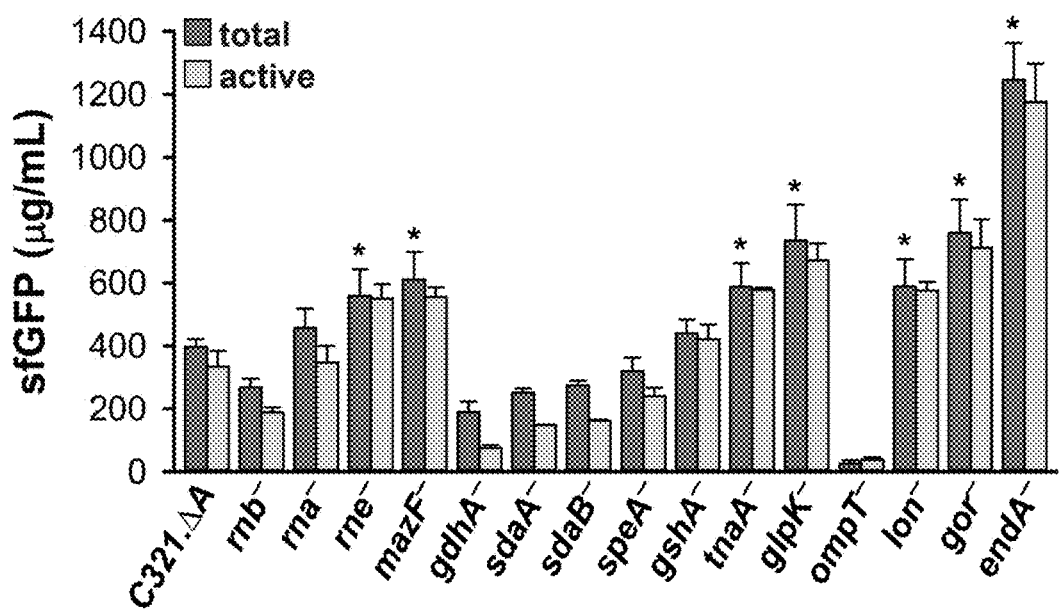
FIG. 8A shows Wild-type (WT) sfGFP yields using cell extracts derived from C321.ΔA and genomically engineered strains comprising an additional knock-out mutation.

To improve the CFPS yields of C321.ΔA, we sought a genomic engineering approach to eliminate putative negative effectors in efforts to stabilize important biomolecules in reactions. First, we targeted the functional inactivation of nucleases, encoded by rna, rnb, rne, mazF, and endA. To streamline our genome engineered approach, we utilized Multiplex Automated Genome Engineering (MAGE) to insert a nonsense mutation into the open reading frames encoding gene-targets, thereby, eliminating the active protein from the proteome and cell-free reaction. A single mutant of each gene-target was generated as part of the first round of our design-build-test cycle. For faster prototyping of engineered strains, we ran cell-free reactions with crude cell lysates made using sonication and synthesized sfGFP over 20 h to analyze bulk protein-synthesis capabilities. Activities from single mutants ranged over two orders of magnitude, spanning from 20 μg/mL to 1.2 mg/mL (FIG. 8A). The highest yielding strain harbored an endA mutation (C321.ΔA.542), which suggests that DNA stability is one of the most important limitations for C321.ΔA in cell-free. C321.ΔA.542 improved active protein yield by ~3.5-fold without appreciably changing cellular fitness, as measured by doubling time. It is interesting to note the functional genomic deletion of the lon protease increases the doubling rate by 19% in relation to the parent strain and also leads to an 80% increase in CFPS performance. In contrast, deletion of the ompT protease does not appear to affect cellular fitness, yet the resulting extracts display dramatic decreases in extract activity upon its deletion (FIG. 8A). It is generally believed that faster growing cells lead to increased cell-free performance, which does not appear to hold across different strains as shown in this work. Additionally, this work demonstrates the difficulty in predicting CFPS productivities from engineered strains and supports the need for efficient, robust, and scalable design cycles for strain engineering to improve cell-free productivities. Looking forward, we sought to identify synergistic benefits of CFPS productivity by combining highly productive mutations.

Figure 8B:
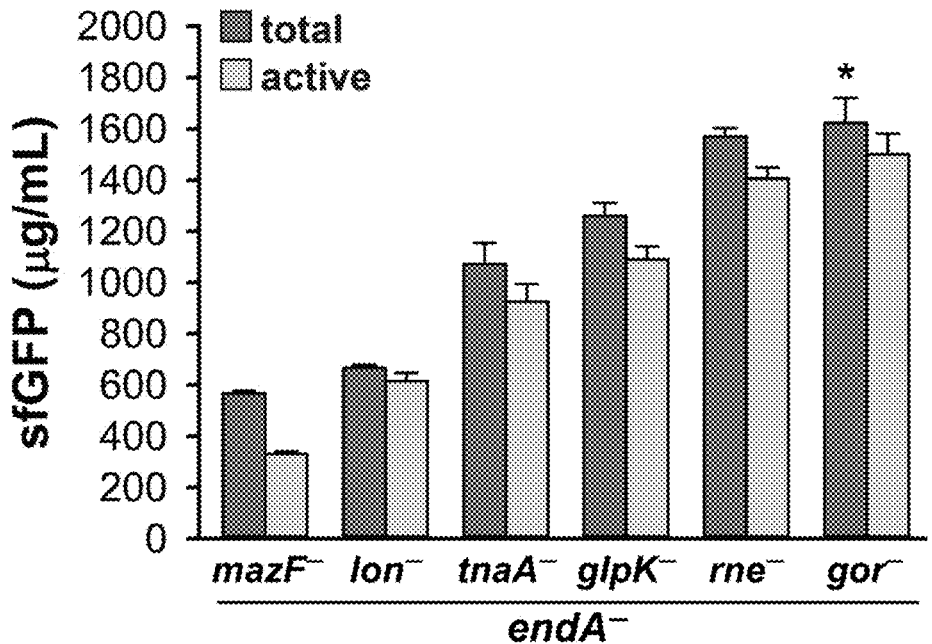
FIG. 8B shows WT sfGFP yields using cell extracts derived from C321.ΔA. and genomically engineered strains comprising two additional knock out mutations.
Figure 8C:
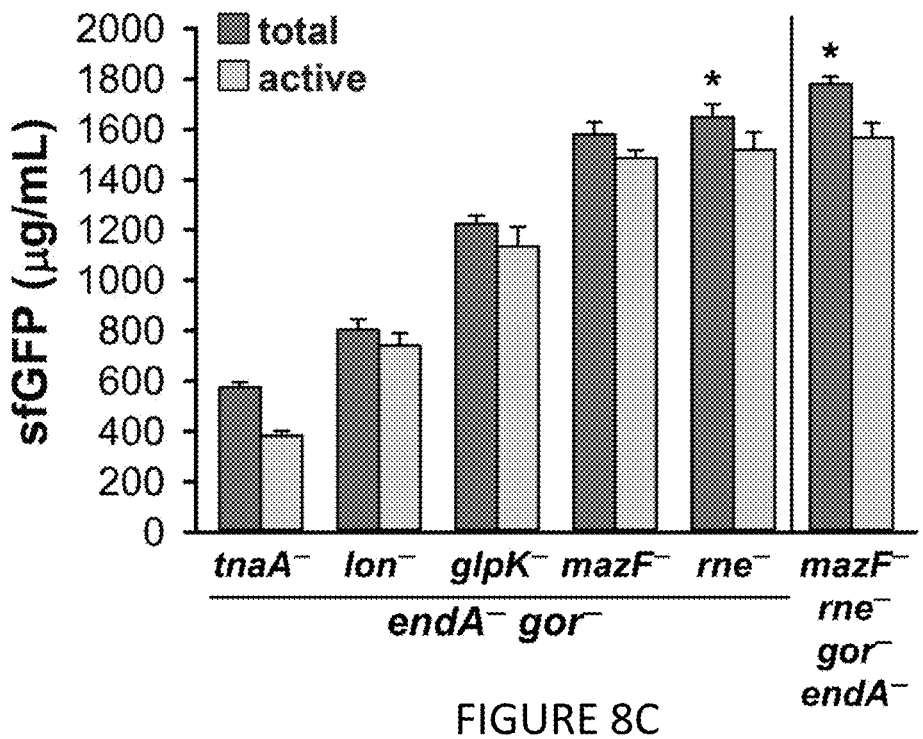
FIG. 8C shows WT sfGFP yields using cell extracts derived from C321.ΔA. and genomically engineered strains comprising three or four additional knock out mutations.
Figure 9:
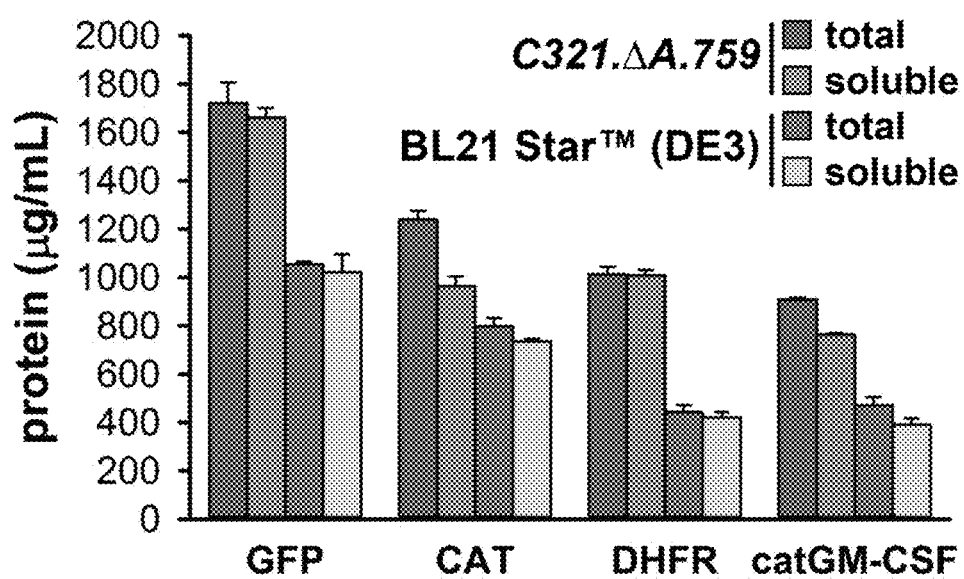
FIG. 9 shows total and soluble protein yields of sfGFP, chloramphenicol acetyltransferase (CAT), dihydrofolate reductase (DHFR), and modified granulocyte-macrophage colony-stimulating factor (catGM-CSF) using lysate derived from C321.ΔA.759 and BL21 Star™ (DE3).

Mutations from strains with productivities significantly greater than C321.ΔA (rne, mazF, tnaA, glpK, lon, and gor) were used in subsequent combinations with the new parent strain, C321.ΔA.542 (FIG. 8B). An improved strain contained an additional gor mutation (C321.ΔA.709) yielded 1.5 mg/mL active sfGFP. Intriguingly, sfGFP does not contain disulfide bonds, so the mechanism for how eliminating glutathione reductase from crude lysates leads to an increase in general protein yields is not clear. This result further provides support for screening efforts that may elucidate new pathways that increase cell-free protein yields in a strain-dependent manner. For our third DBT cycle, we chose C321.ΔA.709 to be the new parent strain and found that the addition of rne (C321.ΔA.705) increased yields to 1.52 mg/mL by potentially providing lysates greater mRNA stability (FIG. 8C). To increase transcript stability further we found a benefit from the addition of a mazF mutation (C321.ΔA.759) which increased yields to 1.55 mg/mL of active protein (FIG. 8C). In general, only slight improvements in lysate productivity were observed in the last two DBT cycles, which suggested diminishing returns in our strain engineering efforts using our gene disruption set. The development of C321.ΔA.759 increased active sfGFP yields by ~4.7-fold, making it potentially one of the highest yielding extract-based systems for NSAA incorporation. To demonstrate generality of CFPS improvements in C321.ΔA.759, we expressed four model proteins and compared productivities to BL21 Star™ (DE3) (FIG. 9). In general a 30 to 60% increase in soluble and total protein synthesis is observed for C321.ΔA. 759 produced sfGFP, chloramphenicol acetyltransferase (CAT), dihydrofolate reductase (DHFR), and modified murine granulocyte-macrophage colony-stimulating factor (catGM-CSF) relative to BL21 Star™ (DE3). Autoradiograms of C321.ΔA.759 produced sfGFP, CAT, DHFR, and catGM-CSF show high purity of our product of interest. The ability to form disulfide bonds in the model catGM-CSF is also observed.

To assess how the targeted deletion of negative protein CFPS effectors in our engineered strains affected various metabolic processes, we performed proteomic studies on select strains. We sought to verify deletion of targeted negative effectors from the proteome as well as analyze how other pathways may have been impacted as a result. Three strains were analyzed for proteomic analysis: C321.ΔA, C321.ΔA.740 (endA$^-$gor$^-$mazF$^-$), and C321.ΔA.705 (endA$^-$gor$^-$ rne$^-$). As validation, in all strains RF1 was not detected. Somewhat unexpectedly, EndA was not detected in all three strains, which could mean it is present at low abundances in C321.ΔA. All other protein products behaved as expected. Gor was only detected in C321.ΔA. MazF was detected in both C321.ΔA and C321.ΔA.705. Full-length Rne was found in C321.ΔA and C321.ΔA.740 and a truncated form consistent with the type of genomic modification (rne131 mutation) made was observed in C321.ΔA.705. In comparison to C321.ΔA, both engineered strains had little differences overall at the proteome level, and only minor differences in the abundance of a few proteins found in specific metabolic pathways (e.g., purine biosynthesis upregulation in C321.ΔA.705). This suggests the mutations we intended to make in C321.ΔA strains translated to the loss of the corresponding protein product and no major changes in metabolism occurred as a results, allowing us to link genotype to phenotype.

In the C321.ΔA strain, the formation of spontaneous mutations occurs at a rate 100-fold more frequent than wild-type strains as a result of a mutS deficiency, which was strategically done in order to increase the efficiency of genome modifications. Because we use this mechanism to increase our MAGE efficiency when making genomic modifications, we also sought to sequence the genomes of six key strains that were produced during our screening efforts: C321.ΔA, C321.ΔA.542, C321.ΔA.705, C321.ΔA.709, C321.ΔA.740, C321.ΔA.759. We found gene targets were confirmed as we expected form MASC PCR and sequencing confirmation, and no severe point mutations were detected that would reasonably change CFPS performance. In all, it appears that only specific changes occurred a desired in our engineered strains and the major improvements in cell-free synthesis is likely a result of a specific deletion of the negative effector(s) in our final strains.

To test our hypothesis that inactivation of RNases would stabilize mRNA in our reactions, we carried out cell-free TL-only reactions for 120 min at 30° C., priming the reaction with purified mRNA template from the sfGFP gene, as opposed to DNA template. Without the ability to replenish mRNA from T7 RNA polymerase, we could now observe the impact of the genomic changes on RNA stability. For this analysis, we specifically focused on extract from C321.ΔA.759. As compared to the extract from the parent strain (C321.ΔA), disruption of mazF and rne increased cell-free translation two-fold. In addition to quantifying sfGFP synthesis by cell-free TL-only reactions, we also examined the mRNA degradation profiles by incubating purified sfGFP mRNA in the cell-free reaction. As expected, mRNA levels were maintained at higher levels in extracts from our enhanced RNase-deficient strain. Specifically, more than ~30% of sfGFP mRNA remained after 120 min incubation with the extracts from double disruption of mazF and me and mRNA levels in the parent extract derived from C321.ΔA were entirely degraded. These results were consistent with the TX-TL reactions and indicate that inactivating RNases from the lysate source strain reduces mRNA degradation and, in turn, improves CFPS.

We next investigated the effects of disrupting the DNA-specific endonuclease I in C321.ΔA.759. We hypothesized that the improved CFPS yields were a result of plasmid DNA stability. To test this hypothesis, we pre-incubated plasmid DNA with extracts from strains with or without endonuclease I, followed by CFPS. If the DNA template was degraded during pre-incubation, or the transcription reaction was inhibited by endonuclease I in some way, less mRNA would be synthesized, which in turn could be responsible for higher CPFS yields when endA was disabled. Plasmid DNA containing the mrPS1 Spinach aptamer gene was pre-incubated with cell extract and a fluorophore molecule, 3,5-difluoro-4-hydroxybenzylidene imidazolinone (DHFBI), for 0, 60, and 180 min. Then, mRNA was synthesized upon addition of CFPS reagents and quantified by measuring the fluorescence of DFHBI-bound Spinach aptamer mRNA. Nearly 50% of Spinach aptamer mRNA was synthesized in C321.ΔA.759 (endA⁻) extracts before and after the pre-incubation. In contrast, the extract with endonuclease I (C321.ΔA) decreased the maximum mRNA syntheses level by 74% after pre-incubation. These results support the hypothesis that endA disruption improves CFPS by helping stabilize the DNA template.

Figure 10A:
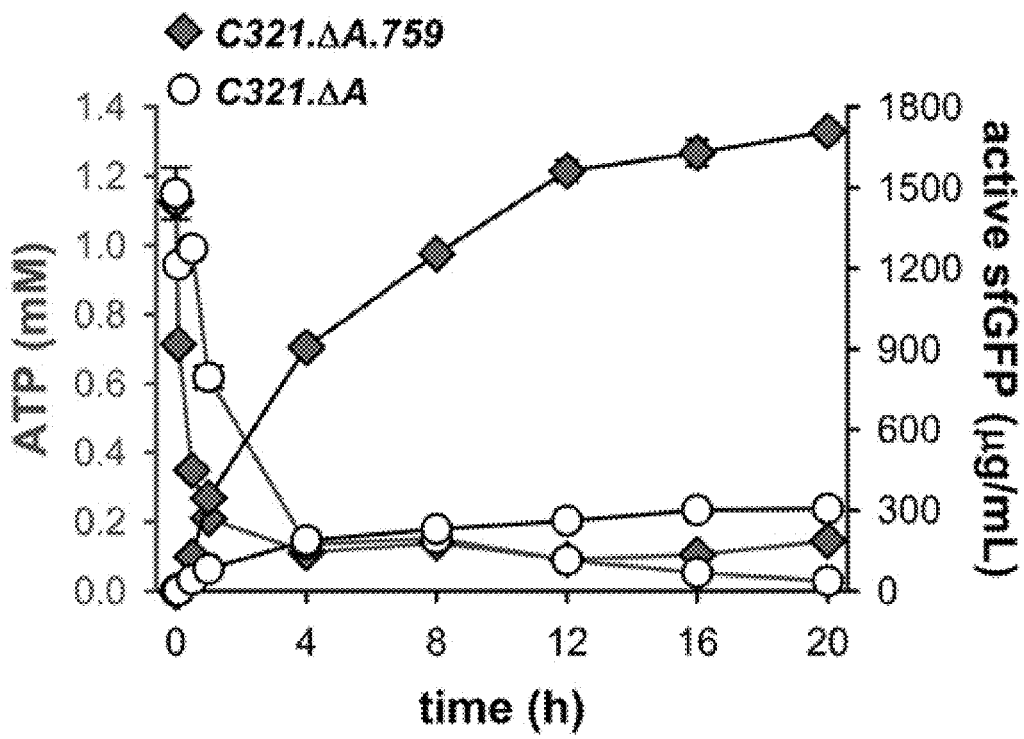
FIG. 10A shows a time-course of active sfGFP production and ATP concentration in cell-free reactions using either C321.ΔA.759 or C321.ΔA extract.
Figure 10B:
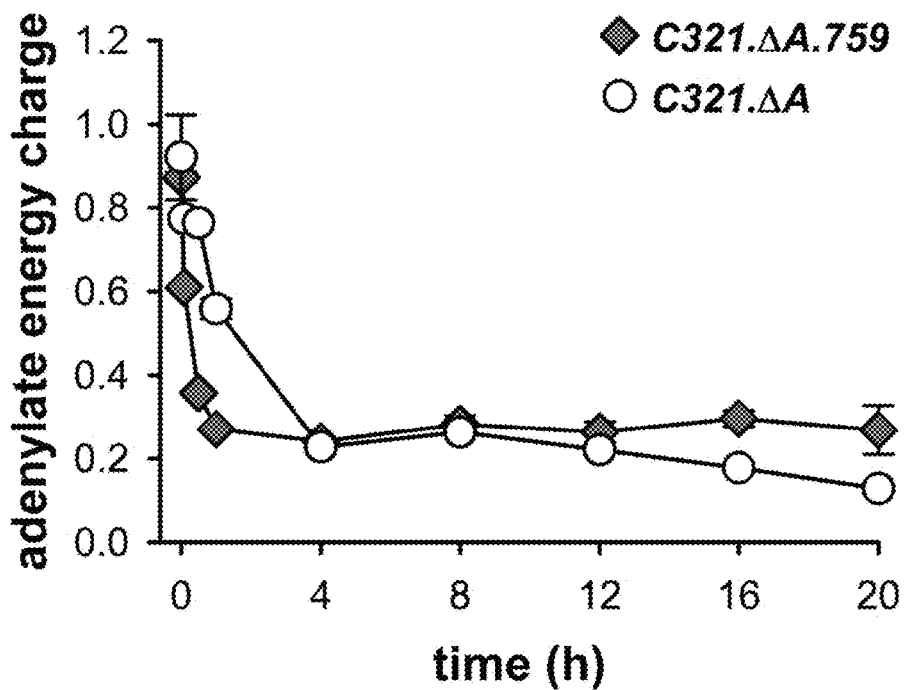
FIG. 10B shows energy charge, energy charge=([ATP]+[ADP]/2)/([ATP]+[ADP]+[AMP]), plotted as a function of reaction time for CFPS reactions using lysate derived from either C321.ΔA.759 or C321.ΔA.

To confirm that DNA and mRNA stability was the main driving force for the increases in yields we observed for C321.ΔA.759, we also analyzed energy and amino acid substrates in the cell-free reaction. Time-course reactions were run over a 20 h time course and samples were collected for high-performance liquid chromatography (HPLC) analysis. To assess any changes to stability that may have occurred in C321.ΔA.759, we compared our results to that obtained using the original parent strain (C321.ΔA) and found little differences in the overall trend for ATP supply (FIG. 10A) in our reactions as well as the resulting adenylate energy charge (FIG. 10B), indicating overall energy stability in cell-free remain unchanged between strains. Importantly, ATP levels in C321.ΔA.759 stay above the previously found limiting threshold of 27 µM found for the *E. coli* CFPS system[34]. With the exception of the 20 h time point, C321.ΔA does not either. By examining the kinetics of sfGFP synthesis, it is observed that >50% of total final product from a 20 h reaction is produced within the first 4 hours, which attests to the rapid, robust, and powerful method in which proteins could be produced in cell-free. Reactions likely slow down after 4 h likely due to the decreased availability of resources and accumulation of inhibitory molecules (e.g., inorganic phosphate).

Amino acid stability was also analyzed using HPLC methods to quantify the concentration of each of the 20 amino acids present in a cell-free reaction mixture. The amino acid profiles for all except glutamate, aspartic acid, and methionine are shown due to technical limitations that make it difficult to resolve the previously mentioned amino acids. In general, very little differences between C321.ΔA.759 and C321.ΔA trends are observed. Despite obtaining high yields over 20 h of CFPS, we observed five amino acids appear to reach near-zero values within 4 h, including: asparagine, serine, glutamine, threonine, and valine. To study if yields could be further improved by increasing the presence of these 5 amino acids, we fed into reactions either 2 or 5 mM of a specific amino acid and a combination of the 5 either 0.5 or 1 h into the reaction. Results from final protein yields after a 20 h reaction suggest that amino acid substrates alone do not increase yields substantially likely because something else is limiting the reaction (e.g., accumulation of inorganic phosphate) unlike what has been observed before[17].

Figure 11A:
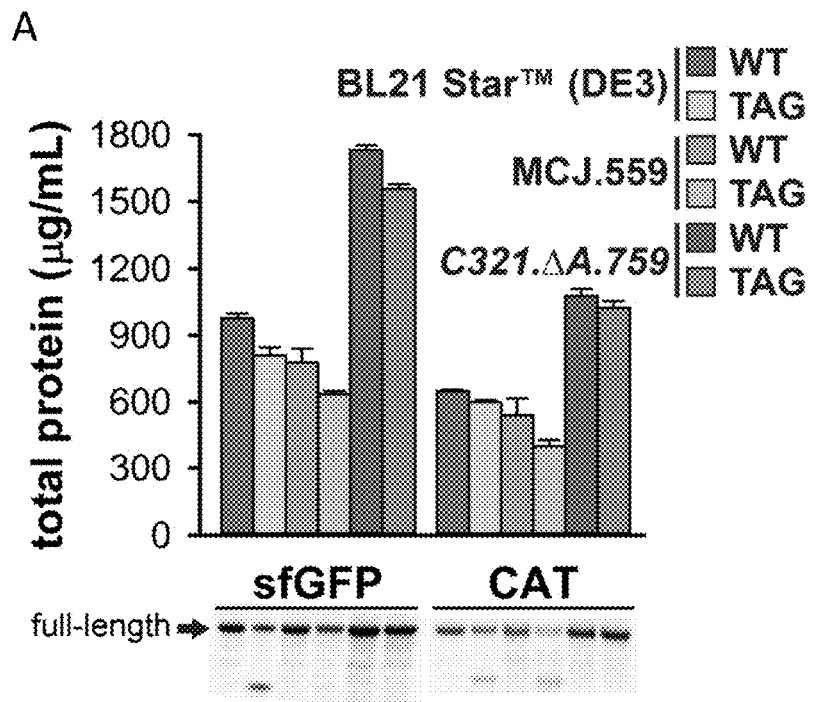
FIG. 11A shows total protein yields for WT and 1 TAG versions of sfGFP and CAT are shown along with an autoradiogram of the resulting protein product.
Figure 11B:
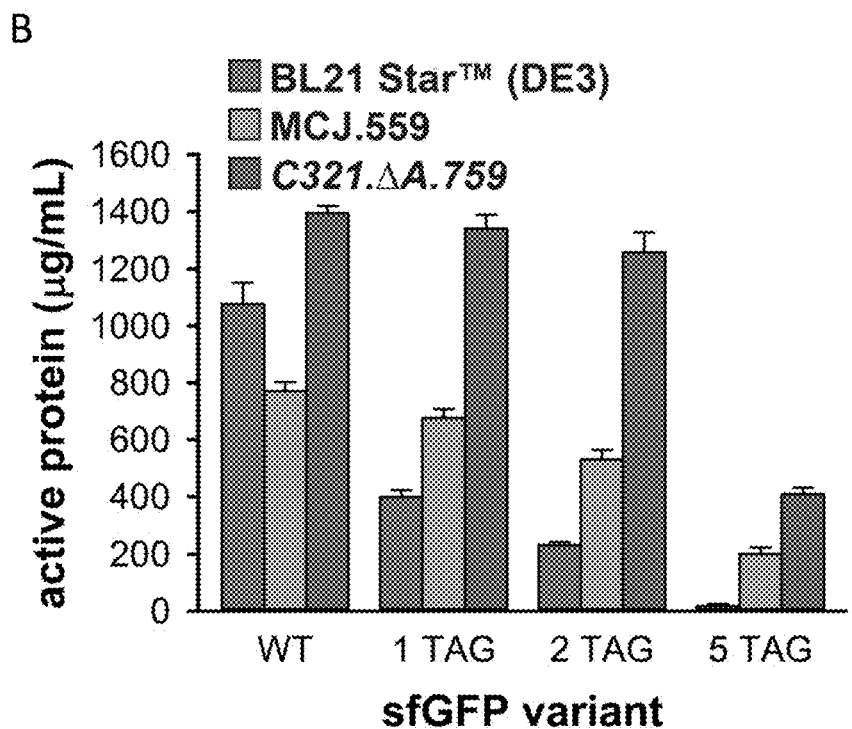
FIG. 11B shows multi-site incorporation of pAcF into sfGFP as measured by active protein produced.

To demonstrate the utility of our genomically engineered strains for NSAA incorporation, we applied lysates from C321.ΔA.759 to the production of proteins with NSAAs incorporated cotranslationally. In the field of non-standard amino acid incorporation, the vector pEVOL is often used to endow strains with the molecular machinery for non-standard amino acid incorporation[33]. This plasmid has been optimized to allow for constant expression of o-tRNA that decodes the UAG stop codon found on transcripts for directed NSAA incorporation. Additionally, it also contains a copy of the orthogonal synthetase under low constitutive expression as well as an arabinose inducible promoter. This plasmid was transformed into three *E. coli* strains to test for the ability of NSAA incorporation and determine whether our engineered strains did in fact improve our ability to add multiple NSAAs into proteins at high yields and purity. The three strains tested were BL21 Star™ (DE3) containing RF1, genomically engineered derived from C13.ΔA[31] (MCJ.559)[8], as well as C321.ΔA.759. To show generality in the improvements observed in our enhanced strain, we first set to synthesize two model proteins, sfGFP and CAT, as either their wild-type form or a version containing one TAG stop codon that codes for the insertion of a NSAA into the protein (FIG. 11A). Total protein produced was maximized from reactions run with C321.ΔA.759+pEVOL-pAcF lysate (FIG. 11A). To demonstrate the purity of NSAA incorporated protein, autoradiograms of the synthesized proteins are shown. Only full-length protein is observed for C321.ΔA.759 for both reporter proteins. However, truncated product is observed for BL21 Star™ (DE3) produced protein with 1 TAG due to RF1 competition[26]. Upregulation of rescue mechanisms for ribosome stalling is likely causing the increase in truncation product observed for the synthesis of CAT-1TAG and is also slightly observed in sfGFP-1TAG [31]. These results clearly display the benefit of using the fully genomically recoded strain lacking RF1 for high-yielding and pure NSAA incorporation.

We next set to extend our comparison to multi-site NSAA incorporation to demonstrate that increases in yields observed for C321.ΔA.759 also apply in the presence of increasing TAG codons in an open reading frame of a protein. This was tested using sfGFP variants, 1 TAG (T216), 1 TAG (E132), 2 TAG (N212 and T216), and 5 TAG (D36, K101, E132, D190, and E213), that only fluoresce upon full-length synthesis and whose active yields correspond to ~85% of total protein produced with the exception of 5 TAG (35%). Results for BL21 Star™ (DE3) display an exponential decrease in active sfGFP synthesized with an increasing presence of TAG, leading to the production of no detectable active protein for sfGFP-STAG. Active protein produced by MCJ.559 was typically half the amount produced by C321.ΔA.759, suggesting that benefits observed in increased yield can be extended to multi-site NSAA incorporation. We then carried out top-down mass spectrometry (i.e., MS analysis of whole intact proteins) to detect and provide semi-quantitative data for the incorporation efficiency of pAcF into sfGFP by C321.ΔA.759. The MS spectra show the 28+ charge state of sfGFP and clearly illustrates mass shifts corresponding to the incorporation of one, two, and five pAcF residues. Site-specific incorporation of pAcF, as detected by MS, was greater than 95% in all samples, with less ≤3 ppm difference between experimental and theoretical protein masses. In other words, we achieved efficient, and high yielding site-specific pAcF incorporation into sfGFP utilizing C321.ΔA.759 lysate.

Thus far, cell-free reactions for producing protein with NSAAs were supplemented with the OTS components as previously optimized for 1 NSAA incorporation (0.5 mg/mL of pAcFRS, 2 mM NSAA, and 10 ng/μL of o-tz-tRNA)[35]. To improve production of proteins with multiple identical NSAAs, we sought to optimize the levels of additional purified OTS added into reactions producing sfGFP-STAG catalyzed by C321.ΔA.759 lysate (FIGS. 12A-C). A 30% increase in 5 TAG sfGFP production was observed upon increasing pAcFRS levels 2-fold, pAcF levels 2.5-fold, and o-tz-tRNA 3-fold. These enhanced levels of OTS components (OTS$^{opt}$) should generally be useful for the production of proteins with multiple identical NSAAs, as was tested in the production of elastin-like polypeptides (ELPs).

Interestingly, upon performing OTS optimization experiments, we note that in the 0 control for pAcFRS optimization we have no productivity of 2 or 5 tag sfGFP (FIG. 12A). This was not expected because we anticipated having low levels of active pAcFRS from culturing cells with the pEVOL plasmid. To further investigate this issue, we ran an individual component assay to determine which components and in what combination are necessary for NSAA incorporation. Said another way, we wanted to deduce which components are being produced from the pEVOL-pAcF plasmid and are maintained in the extract. We note that there is plenty of o-tRNA produced from pEVOL in our cells during culture and thus a large supply of o-tRNA remains in our lysate. We found no active pAcFRS in our lysates as a result of the medium and synthetase induction conditions utilized. To increase pAcFRS activity in our lysates we found it necessary to culture cell in the absence of glucose and in the presence of high levels of the arabinose inducer. However, under pAcFRS overexpression conditions, the overall protein synthesis activity decreases as well as measured by WT-sfGFP synthesis, likely as a result of increased cell stress. Together, these results suggested to us that in order to maintain high yields of protein synthesis, it is beneficial to add in purified synthetase to our cell-free reactions.

Figure 13:
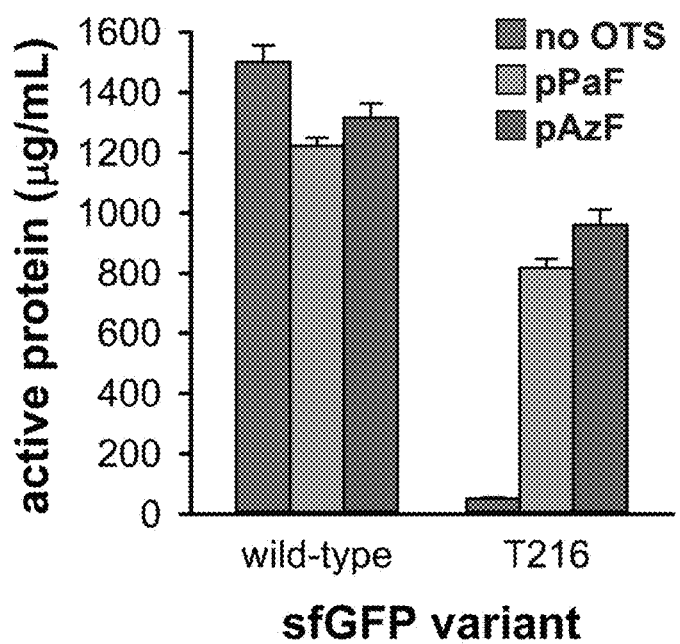
FIG. 13 shows multiple orthogonal translation systems are active in crude lysates derived from C321.ΔA.759. Using OTS$^{opt}$ conditions, pPaF and pAzF were incorporated into position T216 in sfGFP using lysates derived from C321.ΔA.759 overexpressing o-tRNA only from the pDULE plasmid.

To demonstrate that lysates generated from C321.ΔA.759 are compatible with multiple OTS systems, we also demonstrated the synthesis of modified sfGFP using two different orthogonal translation systems that code for pPaF and pAzF (FIG. 13).

Elastin-like polypeptides (ELPs) are highly biocompatible and stimuli-responsive biopolymers which can be applied for drug delivery and tissue engineering. Typically, ELPs consist of repeats of the pentapeptide sequences, VPGVG (TABLE 4). This pentapeptide is known to be a key component in elastin and exhibits interesting self-assembly behavior (random coil to helix) above transition temperature. At a temperature below transition temperature (Tt), ELP molecules assume to have an extended conformation, and thus are soluble in aqueous solution. Upon a temperature shift higher than Tt, however, ELPs become insoluble and form a segregated phase turning into more 'rigid' form [36]. The structure and function of elastin is maintained as long as the glycine and proline residues are present; however, the second valine residue can be replaced with any amino acid. This flexibility in the character of the fourth residue presents an opportunity for modulation of the temperature-responsive properties through introduction of NSAAs. Here, we sought to produce ELPs containing NSAAs using cell-free protein synthesis catalyzed by C321.ΔA.759. We constructed plasmid templates of different monomer sizes, where each monomer contains four pentapeptide, via recursive directional ligation method where n is the number of monomer repeats and X is the NSAA incorporation site (TABLE 4).

TABLE 4

Elastin like polypeptide (ELP) monomers.

| Monomer | | SEQ ID |
|---|---|---|
| ELP | (VPGVG VPGVG VPGVG VPGVG)$_n$ | 97 |
| sELP | (VPGVX VPGVG VPGVG VPGVG)$_n$ | 98 |
| mELP | (VPGVX VPGVX VPGVX VPGVX)$_n$ | 99 |

Figure 14:
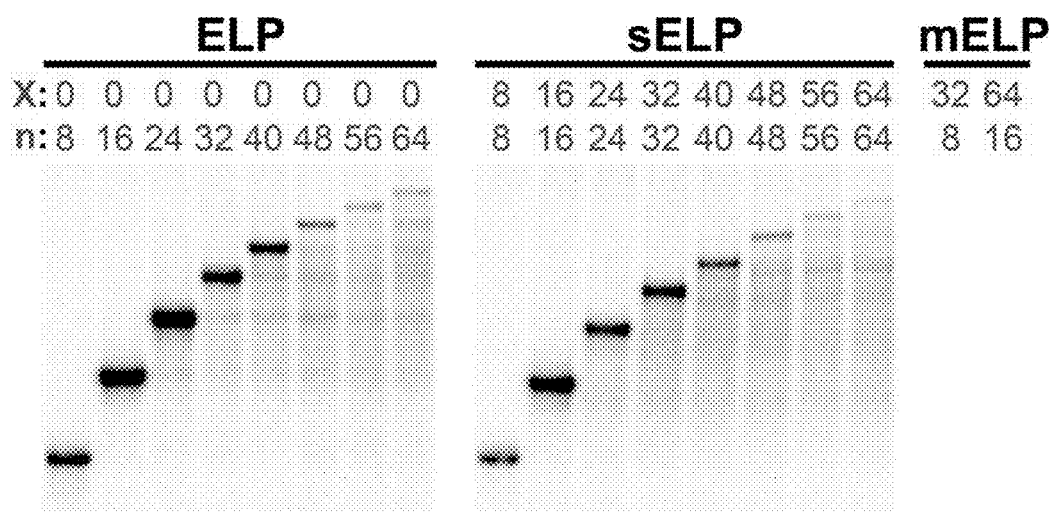
FIG. 14 shows autoradiogram of cell-free produced ELPs, sELPs, and mELPs with increasing monomer units. sELPs and mELPs were produced with the addition of OTS$^{opt}$ into the cell-free reaction to test multi-site NSAA incorporation into locations

Upon application of our OTS$^{opt}$ conditions to the synthesis of sELPs containing 32, 40, and 48 TAGs in the open reading frame, total yields increased by nearly 3-fold. We next applied these conditions to the full synthesis of an array of ELPs containing a range of 8 to 64 TAG codons (FIG. 14). Total $^{14}$C-glycine counts were used to estimate the amount of product produced. In general, the level of protein synthesis capacity is maintained at ~150 to 200 μg/mL of protein over 20 h reactions. However, because of the presence of truncated product, it is estimated that ≥80% of total protein measured is full-length protein as measured by densitometry analysis for constructs with 40 monomers or less. To demonstrate generality, a different construct encoding ELPs with a different amino acid sequence and also showed the ability for C321.ΔA. 759 to synthesize a protein polymer with multiple identical NSAAs. In addition, we also demonstrate the ability for our cell-free system to scale-up reaction volumes by more than 30-fold while maintaining nearly identical production levels of sfGFP-2TAG as well as sELP-8mer construct.

Materials and Methods

Strains and plasmids: The bacterial strains and plasmids used in this study are listed in TABLE 3. Carbenicillin (50 μg/mL) was used for culturing C321.ΔA derivative strains, kanamycin (50 μg/mL) was used for maintaining pY71-based plasmids, and chloramphenicol (34 μg/mL) was used to maintain the pEVOL-pAcF plasmid. E. coli total tRNA mixture (from strain MRE600) and phosphoenolpyruvate was purchased from Roche Applied Science (Indianapolis, Ind.). ATP, GTP, CTP, UTP, 20 amino acids and other materials were purchased from Sigma (St. Louis, Mo.) without further purification. T7 RNA Polymerase was purified in house using ion exchange chromatography.

Strain construction and verification: The strains in this study (TABLE 3) were generated from C321.ΔA[31] by disrupting genes of interest with mutagenic oligonucleotides via MAGE (TABLE 2). Cultures were grown in LB-Lennox media (10 g/L tryptone, 5 g/L yeast extract and 5 g/L NaCl)[37] at 32° C. at 250 rpm throughout MAGE cycling steps. MAGE oligonucleotides were designed to introduce an internal stop codon and frameshift~¼ into the target gene sequence thereby causing early translational termination as previously reported[8]. Combinatorial disruptions of endA, mazF, rna, rnb, rne, gor, lon, ompT, gdhA, gshA, sdaA, sdaB, speA, tnaA, and glpK were generated to investigate the effect of their inactivation in CFPS. Multiplex allele-specific colony PCR was performed to verify gene disruptions[37] using wild-type forward (-wt-F) or mutant forward (-mut-F) primers and reverse primers (-R) (TABLE 2). Wild-type and mutant forward primers were identical except at the 3'-ends of the oligonucleotides, and the reverse primers were used for detection of both wild-type and mutant alleles. The mutant allele could be amplified using the mutant forward and reverse primer set (-mut-F an—-R) but not amplified by the wild-type forward and reverse primer set (-wt-F an—-R). MASC PCR was performed in 20 µL reactions using multiplex PCR kit (Qiagen, Valencia, Calif.) at 95° C. for 15 min, with 30 cycles of 94° C. for 30 sec, 65° C. for 30 sec, and 72° C. for 1 min, and a final extension of 72° C. for 5 min. Mutant alleles were screened by running PCR products on a 2% agarose gel and confirmed by DNA sequencing using sequencing primers (TABLE 2).

Growth rate assessment: Overnight cultures of engineered strains grown in Luria-Bertani (LB)[38] at 250 rpm at 34° C. were diluted 1000-fold in 2×YTPG media (31 g/L 2×YT, 7 g/L $K_2HPO_4$, 3 g/L $KH_2PO_4$, and 18 g/L glucose; adjusted pH to 7.2 with KOH). 100 µl of the diluted cultures were added to 96-well polystyrene plates (costar 3370; Corning, Corning, N.Y.). OD was measured at 15 min intervals for 15 h at 34° C. in fast shaking mode on a Synergy 2 plate reader (Biotek, Winooski, Vt.). Growth data of each strain was obtained from three independent cultures each split into three replicate wells (9 total samples per strain). Doubling time was calculated during the early exponential growth phase ($OD_{600}$ of 0.02 to 0.2).

Cell extract preparation: For rapid prototyping of engineered strains, cells were grown in 1 L of 2×YTPG media (pH 7.2) in a 2.5 L Tunair® shake flask and incubated at 34° C. at 220 rpm to $OD_{600}$ of 3.0. Cells were pelleted by centrifuging for 15 min at 5000×g at 4° C., washed three times with cold S30 buffer (10 mM tris-acetate pH 8.2, 14 mM magnesium acetate, 60 mM potassium acetate, 1 mM dithiothreitol)[39], and stored at −80° C. To make cell extract, cell pellets were thawed and suspended in 0.8 mL of S30 buffer per gram of wet cell mass and 1.4 mL of cell slurry was transferred into 1.5 mL microtubes. The cells were lysed using a Q125 Sonicator (Qsonica, Newtown, Conn.) with 3.175 mm diameter probe at a 20 kHz frequency and 50% amplitude. To minimize heat damage during sonication, samples were placed in an ice-water bath. For each 1.4 mL sample, the input energy was ~944 Joules and was monitored during sonication. Lysate was then centrifuged at 12,000×g at 4° C. for 10 min. For strain derivatives of MG1655, a run-off reaction (37° C. at 250 rpm for 1 h) and second centrifugation (10,000×g at 4° C. for 10 min) were performed[40]. The supernatant was flash-frozen using liquid nitrogen and stored at −80° C. until use. The total protein concentration of the extracts were 40~50 mg/mL as measured by Quick-Start Bradford protein assay kits (Bio-Rad, Hercules, Calif.).

Purification of His-tagged orthogonal tRNA synthetase: BL21 (DE3) harboring pY71 plasmid encoding either pAcFRS, pAzFRS, or pPaFRS were grown in 1 L of 2×YT to an $OD_{600}$ of 1.0 at 220 rpm and 37° C. Orthogonal synthetase production was induced by adding 0.3 mM isopropyl-β-D-thiogalactopyranoside (IPTG, Sigma-Aldrich, St. Louis, Mo.) and cells were allowed to grow for an additional 3 h. Cells were harvested at 5,000× g for 15 min at 4° C., washed with S30 buffer, and stored at −80° C. Frozen cell pellets were thawed in loading buffer (1 mL of 300 mM NaCl, 10 mM imidazole, 50 mM $NaH_2PO_4$, pH 8.0 solution per gram of wet cells), lysed using sonication as described above and centrifuged at 16,000×g at 4° C. for 10 min. The supernatant was diluted 1:1 with loading buffer and incubated at 4° C. for 1 h with Ni-NTA beads prewashed with dilution buffer (300 mM NaCl, 50 mM $NaH_2PO_4$, pH 8.0). The orthogonal synthetase was purified using elution buffer (300 mM NaCl, 250 mM imidazole, 50 mM $NaH_2PO_4$, pH 8.0) and subsequently dialyzed against S30 buffer and 25% glycerol in a Slide-A-Lyzer™ G2 Dialysis Cassette (Life Technology, Grand Island, N.Y.). Dialyzed synthetase was concentrated using Amicon Ultracel YM-30 centrifugal filter and stored at −80° C. Purified synthetase was quantified by the Quick-Start Bradford protein assay kit (Bio-Rad, Hercules, Calif.).

CFPS reaction: A modified PANOx-SP system was utilized for CFPS reactions testing incorporation of $pAcF^2$. Briefly, a 15 µL CFPS reaction in a 1.5 mL microtube was prepared by mixing the following components: 1.2 mM ATP; 0.85 mM each of GTP, UTP, and CTP; 34 µg/mL folinic acid; 170 µg/mL of E. coli tRNA mixture; 13.3 µg/mL plasmid; 16 µg/mL T7 RNA polymerase; 2 mM for each of the 20 standard amino acids; 0.33 mM nicotinamide adenine dinucleotide (NAD); 0.27 mM coenzyme-A (CoA); 1.5 mM spermidine; 1 mM putrescine; 4 mM sodium oxalate; 130 mM potassium glutamate; 10 mM ammonium glutamate; 12 mM magnesium glutamate; 57 mM HEPES, pH 7.2; 33 mM phosphoenolpyruvate (PEP), and 27% v/v of cell extract. For NSAA incorporation, 2 mM pAcF, 0.5 mg/mL pAcFRS, and 10 µg/mL of o-tz-tRNA linear DNA were supplemented to cell-free reactions. For multi-site NSAA incorporation, $OTS^{opt}$ levels were increased to 5 mM pAcF, 1 mg/mL pAcFRS, and 30 µg/mL o-tz-tRna. o-tRNA linear DNA was amplified from pY71-T7-tz-o-tRNA plasmid as described previously[35] and transcribed during the cell-free reaction. Furthermore, the o-tRNA was expressed in the source strain prior to extract preparation. Each CFPS reaction was incubated for 20 h at 30° C. unless noted otherwise.

Fed-batch CFPS reactions: For fed-batch reactions, 15 µL CFPS batch reactions were prepared as described above. At the specified time, the reactions were removed from the incubator, supplied with 0.5 µL of feeding solution containing the appropriate concentration of the desired amino acid(s), mixed with a pipette, and returned to the incubator. All reactions were incubated at 30° C. for 20 h total and assayed.

Scale up CFPS: Cell-free reaction volumes were scaled to 300 µL in flat-bottom 24-well polystyrene plate (model 353226; BD Biosciences, San Jose, Calif.). Three 300 µL reactions were run in parallel for the production of milligram quantities of mELP8 (32 NSAA) and sfGFP-2TAG. Remaining wells around the perimeter of the plate were filled with water for internal humidification, which resulted in reduced sample evaporation. By filling the outer chambers surrounding the wells with water, which humidified the air, negligible sample evaporation was achieved. Reactions were performed at 30° C. for 20 h while shaking at 300 RPM in a ThermoMixer (Eppendorf, Mississauga, Ontario).

Quantification of active sfGFP: Active full-length sfGFP protein yields were quantified by measuring fluorescence using a Synergy 2 plate reader (BioTek, Winooski, Vt.) with excitation at 485 nm, emission at 528 nm, and cut-off at 510 nm in 96-well half area black plates (Costar 3694; Corning, Corning, N.Y.). sfGFP fluorescence units were converted to concentration using a standard curve established with 14C-Leu quantified sfGFP as described previously[35].

Quantification of total and soluble protein: Radioactive $^{14}C$-Leu was added into 15 µL CFPS reactions 15 µL cell-free reactions. Reactions were taken at the indicated time and 5 µL of sample was removed for total protein quantitation. The remaining sample was centrifuged at 16,000×g at 4° C. for 10 min and the top 5 μL was used to measure the soluble protein. Total and soluble protein yields were quantified by determining radioactive $^{14}$C-Leu incorporation into trichloroacetic acid (TCA—-precipitated protein[39]. Radioactivity of TCA-precipitated samples was measured using liquid scintillation counting (MicroBeta2, PerkinElmer, Waltham, Mass.). For autoradiogram analysis, 2.5 μL of each reaction was loaded on 4-12% NuPAGE SDS-PAGE gel after denaturing the sample. The gel was soaked in Gel Drying solution (Bio-Rad, Hercules, Calif.) for 30 min, fixed with cellophane films, dried by applying heat for 1 h in GelAir Dryer (Bio-Rad, Hercules, Calif.) for 30 min, fixed with cellophane films, dried by applying heat for 1 h in GelAir Dryer (Bio-Rad, Hercules, Calif.), and exposed overnight on Storage Phosphor Screen (GE Healthcare Biosciences, Pittsburgh, Pa.). Autoradiograms were scanned using Storm Imager (GE Healthcare Biosciences, Pittsburgh, Pa.) and analyzed using Quantity One software (Bio-Rad, Hercules, Calif.).

All-in-one cell-free system for pAcF incorporation: C321.ΔA.759 harboring the pEVOL-pAcF plasmid was cultured with varying levels of arabinose to induce the overexpression of pAcFRS in vivo prior to extract preparation. C321.ΔA. 759+pEVOL-pAcF was grown on 2×YTPG media (31 g/L 2×YT, 7 g/L $K_2HPO_4$, 3 g/L $KH_2PO_4$, and 18 g/L glucose; adjusted pH to 7.2 with KOH) and induced with 0.2% arabinose at 0.6 $OD_{600}$ for low expression of pAcFRS. For larger levels of pAcFRS overexpression, 2×YTP media (31 g/L 2×YT, 7 g/L $K_2HPO_4$, 3 g/L $KH_2PO_4$; adjusted pH to 7.2 with KOH) with 2% arabinose induction at 0.6 $OD_{600}$ and 2×YTPA media (31 g/L 2×YT, 7 g/L $K_2HPO_4$, 3 g/L $KH_2PO_4$, and 18 g/L arabinose; adjusted pH to 7.2 with KOH) were utilized for growth. Cells were then harvested and corresponding extracts were produced as described above. Overexpression of pAcFRS was analyzed by Coomassie-blue staining analysis on a 4-12% SDS-PAGE gel (Life Technology, Grand Island, N.Y.) and by the cell-free synthesis of proteins with NSAAs without additional purified pAcFRS or o-tRNA.

Whole genome sequencing: To analyze the occurrences of random mutations appearing in strains, the following genomically engineered strains were sequenced: C321.ΔA, C321.ΔA.542, C321.ΔA.705, C321.ΔA.709, C321.ΔA.740, C321.ΔA.759. One milliliter of confluent cell culture in LB broth was processed with a Qiagen DNeasy Blood and Tissue (cat: 69504) to extract genomic DNA. gDNA quality was assessed on a spectrophotometer (assay for A260/280 ratio between 1.8 and 2.0) and by gel electrophoresis (assay for a tight smear at ~50 kB). 2.5 μg of gDNA, eluted in 50-μl TE pH 8.0, was sent to the Yale Center Genome Analysis for library prep as described previously[41].

mRNA stability assay: mRNA stability was assessed as described previously[8]. Briefly, the sfGFP gene was PCR amplified from the pY71 vector and purified by PCR cleanup kit (Promega, Madison, Wis.). This template was used for T7-driven in vitro transcription reactions. In order to track mRNA stability in our extracts, sfGFP was synthesized using purified mRNA (1,800 ng) in the CFPS reaction. For direct measurement of mRNA degradation, purified mRNA samples from the cell-free reaction were visualized on a 2% formaldehyde agarose gel stained with GelRed (Biotium, Hayward, Calif.).

DNA stability assay: DNA stability was assessed as described previously[8]. Briefly, A preincubation mixture containing 4 μL of cell extract, 12.96 ng/μL of pY71-mRFP1-Spinach plasmid (TABLE 3), and 6 nM of 3,5-difluoro-4-hydroxybenzylidene imidazolinone (DFHBI; Lucerna, New York, N.Y.) was incubated for 0, 60, and 180 min at 30° C. Then, CFPS reaction components were added immediately after the preincubation step, and fluorescence of the Spinach aptamer binding to DFHBI was monitored for 180 min using CFX96 Real-Time RT-PCR module installed on C1000 Touch Thermal Cycler (Bio-Rad, Hercules, Calif.). The excitation and emission wavelength of the fluorophore were 450-490 nm and 515-530 nm, respectively.

Nucleotide and amino acid concentration quantitative HPLC assay. High-performance liquid chromatography (HPLC) analysis was used to measure nucleotide and amino acid concentrations. For both assays, 5% v/v TCA was added to the cell-free reaction mixture in a 1:1 volumetric ratio. Samples were centrifuged at 16,000×g for 15 min at 4° C. The supernatant was collected and samples were analyzed using an Agilent 1260 series HPLC system (Agilent, Santa Clara, Calif.) as described previously[41].

ELP construction: ELP genes were synthesized at GenScript (Piscataway Township, N.J.) and codon optimized for E. coli expression. Wild-type ELP genes contained eight monomer units with four pentapeptides (VPGVG) in a monomer unit[36], sELP genes contained an amber site (TAG) to direct the incorporation of a NSAA (X) at the fourth residue of one of the repeats (VPGXG) in a monomer unit, and mELP genes contained four amber sites in a monomer unit (TABLE 4). The synthesized ELP 8-mer genes were provided on a pUC57 vector and cloned into pY71-FlSt vector containing N-terminal Flagtag and C-terminal Streptag for purification purposes using NcoI and NotI restriction sites (TABLE 2). The number of monomers were increased via recursive directional ligation method using BveI and BpiI restriction sites[42] resulting in 8, 16, 24, 32, 40, 48, 56, and 64mers for ELP-wt and sELP, and 8 and 16mers for mELP (FIG. 14). In order to enhance Streptag column purification of ELP for mass spectrometry analysis, we added Twin-Streptag into 8 and 16mers of ELPs using NotI and BlpI restriction sites (TABLE 2). To demonstrate the generality of our system, we also tested different versions of ELPs obtained from Farren Isaacs and colleagues (in revision). FI-ELPs contained three pentapeptides in a monomer unit for 30 and 40mers and an amber site in a monomer unit for NSAA incorporation. First, we constructed pY71-KA-sfGFP vector by adding KpnI and ApaI restriction sites at 5'- and 3'-end of sfGFP gene, respectively (TABLE 2), and then FI-ELP genes were cloned into this vector using same restriction sites resulting in ELPs with C-terminal sfGFP fusion. For MS analysis, we added Twin-Streptag using ApaI and BlpI restriction sites in place of sfGFP gene (TABLE 2). All ELP plasmids are listed in TABLE 3.

Full-length sfGFP and ELP purification and mass spectrometry: To confirm pAcF incorporation at corresponding amber sites, semi-quantitative mass spectrometry (MS) analysis was performed on purified sfGFP and ELP reporter protein with pAcF putatively incorporated. First, full-length reporter protein was purified from CFPS reactions using C-terminal strep-tags and 0.2 mL gravity-flow Strep-Tactin Sepharose mini-columns (IBA GmbH, Gottingen, Germany) and concentrated using Microcon centrifugal filter columns YM-10 (Millipore, Billerica, Mass.). The purified reporter protein was then analyzed by nano-capillary LC-MS using a 100 mm×75 μm ID PLRP-S column in-line with an Orbitrap Elite (ThermoFisher, Waltham, Mass.). All MS methods included the following events: 1) FT scan, m/z 400-2,000, 120,000 resolving power and 2) data-dependent MS/MS on the top 2 peaks in each spectrum from scan event 1 using higher-energy collisional dissociation (HCD) with normalized collision energy of 25, isolation width 15 m/z, and detection of ions with resolving power of 60,000. All data were analyzed using QualBrowser, part of the Xcalibur software packaged with the ThermoFisher Orbitrap Elite (ThermoFisher, Waltham, Mass.). In the MS spectra, smaller peaks to the right of the main peaks ($\Delta m=+16$ Da) are due to oxidation of the protein—a common electrochemical reaction occurring during electrospray ionization. The presence of the initial methionine amino acid residue on a protein will also increase the mass ($\Delta m=+131$ Da) and are detected to the right of the major peak. To remove non-covalent salt and water adducts from intact proteins (in this case sfGFP), a small level of in-source collision energy (15 eV) was applied. As a result, water loss events from the intact sfGFP ($\Delta m=-18$ Da) are detected at minor levels to the left of the major peak.

Example 3

Methods of Making and Using and Using RF1 Deficient C321.ΔA Strains for the Preparation of Proteins and Sequence-defined Biopolymers Incorporating Pyrrolysine-based NSAAs We tested the incorporation of two NSAAs: 1) $N^6$-(5-Norbornen-2-yloxycarbonyl)-L-Lysine Hydrochloride hereafter referred to as Pyrrolysine Norbornene and 2) $N^6$-(propargyloxycarbonyl)-L-Lysine Hydrochloride hereafter referred to as Propargyl Carbamate. Leveraging the open nature of the cell-free system, we first optimized the expression of modified proteins (i.e., those containing NSAA) by adjusting the composition of purified cell-free components (e.g., tRNAcuAPyl, PylRS, etc.). We did so in two different strains, with and without RF1. Second, we assessed the impact of PylRS and tRNAcuAPyl in the extract during source strain generation rather than adding them as purified exogenous components. Third, we directly compared the results from the CFPS system to those from cells. The resulting CFPS platform synthesized the highest reported yield of modified protein harboring single and multiple identical pyrrolysine-based NSAAs, outperformed the in vivo system, and underscores the importance of using extracts from genomically recoded extracts lacking RF1 for efficient and accurate NSAA incorporation.

Creation of an efficient CFPS platform for incorporation of pyrrolysine-based NSAAs required the following 3 components in addition to added buffers and enzymes: 1) Purified PylRS, 2) a purified Pyl tRNA construct and 3) suitable 830 extract.

PylRS was cloned into a pET21 a vector with C-terminal His Tag and expressed in 8121 DE3 cells. The expressed protein is highly insoluble forming aggregates making it difficult to purify. However, shocking the cells with heat at 42° C. prior to induction of the protein makes it more soluble and therefore allows for efficient purification of the synthetase from the cell lysate using Ni-NT A agarose beads (58).

The tRNA construct, known as transzyme was created to allow for synthesis of the tRNA in the same reaction as the protein of interest in the cell-free reaction. Pyl tRNA was cloned downstream of a T7 promoter and a ribozyme sequence (TABLE 5). This technique has been successfully applied to synthesize orthogonal tRNA in cell-free reactions (35, 21). Both the ribozyme and the tRNA are transcribed by T7 polymerase, following which the ribozyme is able to cleave itself, allowing for the release of the correctly folded tRNA. For use in our system, the t-RNA construct was amplified from the plasmid with an additional 500 bases at the N-terminal in order to allow the T7 enzyme to properly bind to the construct.

S30 extract is prepared using the standard S30 extract preparation protocol as outlined in the methods section. Selection of the right cell strain, as well as expression of the Pyl AARS and Pyl tRNA during the S30 extract preparation is key to efficient CFPS reactions and will be described in the following sections.

S30 BL21 extract was initially prepared using the standard S30 extract preparation protocol on Bl21 DE3 cells as outlined in the methods section. We tested the ability of this extract (supplemented with purified PylRS and Pyl tRNA) to incorporate Pyrrolysine Norbornene into an in-frame amber stop codon in sfGFP at position 216 (sfGFPT216). Results indicated that this extract did not produce any measurable level of sfGFP as measured by fluorescence. In order to improve the performance of the extract we expressed a pEvol Pyl plasmid containing two copies of the PylRS and a single copy of the Pyl tRNA during the exponential phase of cell growth. This extract, termed BL21 pEvol, was able to incorporate pyrrolysine norbornene into sfGFP as measured by fluorescence.

We then carried out an assay to optimize the different concentrations of PylRS and Pyl tRNA that needs to be added to this BL21 pEvol extract. Increasing concentrations of PylRS and PyltRNA were added to the reaction in various combinations and the resulting sfGFP fluorescence of each reaction was plotted in Matlab in a two point lattice. We observed an increase in the fluorescence values with increasing concentrations of PylRS but not so with increasing concentrations of tRNA. This indicated that PylRS and not tRNA was limiting in the reactions even at the highest concentration of PylRS added to the reaction. We were unable to concentrate the PylRS further due to insolubility issues and therefore attempted to increase the concentration of PylRS in the extract by expressing a second plasmid during extract preparation time. Extract BL21 pEvolpET was created by expressing the pEvol Pyl plasmid from above along with a pET21 aMmPyl vector with a single inducible copy of the PylRS cloned into it. When we tested this new extract (BL21 pEvolpET) we found that it performed slightly better than the BL21 pEvol extract indicating that additional PylRS facilitates incorporation of the NSAA.

A separate assay was carried out to test if expressing PylRS during extract preparation time is equivalent/better or worse than adding exogenous purified PylRS (6.8 μM). Results indicate that initially it is critical to express the pEvol Pyl plasmid in the extract, as adding exogenous PylRS does not facilitate the reaction. However, once the extract has a certain concentration of PylRS such as in the BL21 pEvol extract, further addition of exogenous PylRS (6.8 μM) is approximately equivalent to expressing a second PylRS containing plasmid during extract preparation (Bl21 pEvolpET extract). The reaction can be further improved if this final BL21 pEvolpET extract is supplemented with additional purified exogenous PylRS (6.8 μM).

We then tested the new BL21 pEvolpET extract with added tRNA and synthetase for the incorporation of a second NSAA, Propargyl carbamate, and compared its incorporation to that of Pyrrolysine Norbornene. sfGFP fluorescence was measured for samples with and without the added NSAAs and converted to concentration (μg/ml) according to a standard curve (35). We were able to see 303.5±16.8 μg/ml of GFP produced when propargyl carbamate was added to the extract and 179.8±8.3 μg/ml when pyrrolysine norbornene was added. We also used autoradiography to visualize radiolabeled sfGFP produced in all three extracts with and without the two NSAAs. As with the fluorescence data, we observed only truncated sfGFP in the BL21 extract with and without the NSAAs. This extract is unable to incorporate the NSAA into the amber position at amino acid 216 and therefore we see no full length product. The other two extracts do show the presence of full-length sfGFP upon addition of the NSAAs. However, the majority of the protein is still truncated which is to be expected in an extract that still has RF1.

We obtained the C321.ΔA E. coli strain lab which has been genomically recoded to delete RF1 and replace all 321 UAG amber codons with UAA codons (21). This strain shows increased ability to incorporate NSAAs. We therefore used the C321.ΔA.ΔendA strain, henceforth known as rEcoli strain and compared this extra"t's activity to the BL21 strains.

Figure 15:
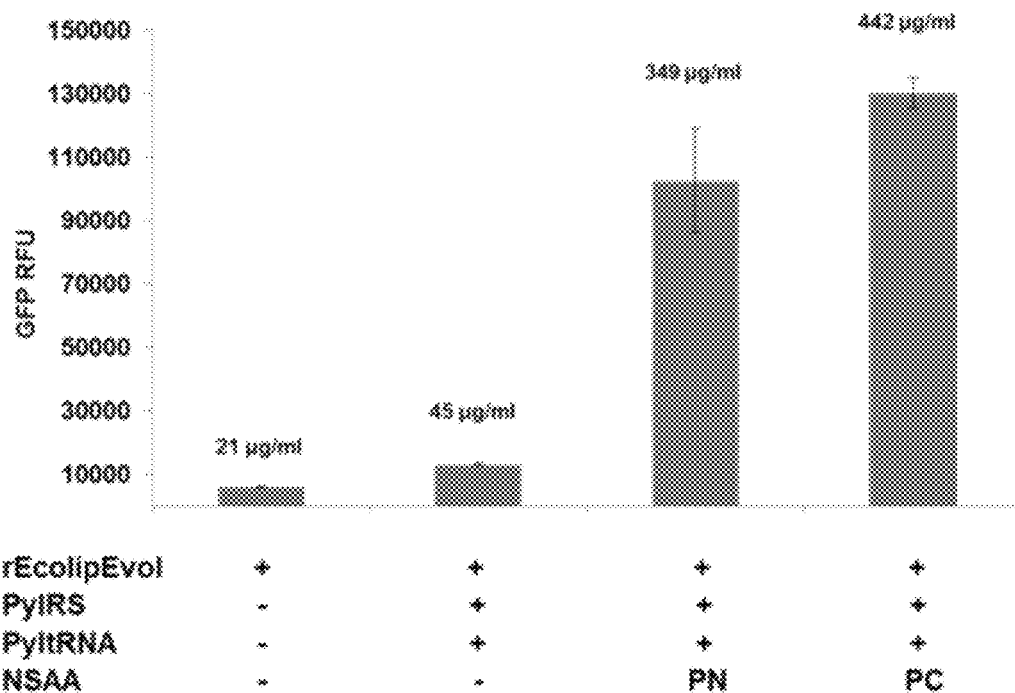
FIG. 15 shows a comparison of sfGFP relative fluorescence units in samples in the presence (+) and absence (−) of NSAAs (PN: Pyrrolysine Norbornene; PC: Propargyl Carbamate) in rEcolipEvol extract from samples in which a single amber codon is suppressed (position T216).

We produced S30 extract from rEcoli cells transformed with the pEvol plasmid (rEcoli pEvol Extract). Experiments to determine if we were AARS or tRNA limited in this extract indicated that addition of extra PylRS or Pyl tRNA did not significantly affect the incorporation of NSAAs. Additionally, we were unable to express the pET vector with the single copy of the PylRS gene due to the absence of the T7 cassette from this new strain. As with BL21, we tested the amount of sfGFP produced in the rEcoli pEvol extracts with and without the addition of the two NSAAs. We saw 349±79 μg/ml of sfGFP with pyrrolysine norbornene and over 442±22.8 μg/ml with propargyl carbamate (FIG. 15). This is a significant improvement in the amount of sfGFP produced by the best performing BL21 extract. Autoradiography experiments to visualize protein showed a drastic reduction in the amount of truncated protein and a corresponding increase in the amount of full length sfGFP.

Figure 16:
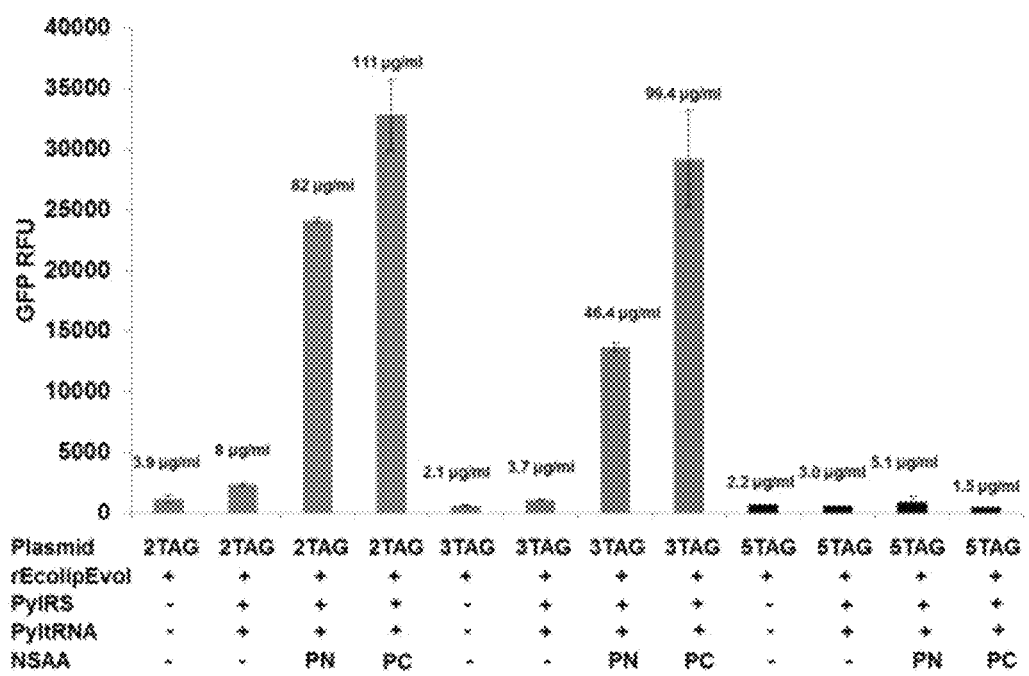
FIG. 16 shows a comparison of sfGFP relative fluorescence units in samples in the presence (+) and absence (−) of NSAAs (PN: Pyrrolysine Norbornene; PC: Propargyl Carbamate) in rEcolipEvol extract from samples in which a 2 (2TAG), 3 (3TAG), and 5 (5TAG) amber codons are suppressed.

Published results using the C321.ΔA strain show that it is able to suppress multiple amber codons in vivo, whereas the BL21 strain is unable to do so due to the presence of RF1 in the extracts. We next studied if our newly created cell-free extract had the ability to incorporate multiple NSAAs into sfGFP. We tested 2, 3 and 5 TAG containing sfGFP constructs for incorporation of both pyrrolysine norbornene and propargyl carbamate (FIG. 16). The 2TAG construct produced 82 and 111 μg/ml of sfGFP respectively in the rEcoli pEvol extracts whereas the 3TAG construct produced around 46 and 99 μg/ml of sfGFP. We were not able to detect levels of sfGFP much above background in the STAG construct. Therefore this cell-free extract can be used to incorporate up to 3 unnatural pyrrolysine-derivative NSAAs into sfGFP. By comparison, the BL21 based extracts were not able to incorporate multiple NSAAs.

We used top-down (TD) mass spectrometry (i.e., MS analysis of intact proteins) to detect the incorporation of pyrrolysine norbornene and propargyl carbamate into sfGFP. In vitro CFPS reactions were set up and incubated overnight following which the synthesized protein was purified over a Strep-Tactin column that bound to the C-terminal Strep tag. Results show >95% incorporation for each of these NSAAs at the TAG site in sfGFP constructs with 1, 2 and 3 TAGs.

In order to test how our in vitro extracts compared to in vivo incorporation of these two NSAAs into sfGFP we co-transformed the pEvol Pyl vector and a plasmid containing sfGFP with an amber codon in place of Threonine 216 (sfGFPT216) into BL21 DE3 cells. We inoculated an overnight culture of this strain in LB and grew for approximately an hour till OD 0.1 (as measured by the Synergy H1) after which we added NSAAs to a final concentration of 2 mM and shook till OD 0.2. We then added IPTG and Arabinose to final concentrations of 5 mM and 0.1% respectively and shook overnight while measuring the sfGFP fluorescence every 30 minutes for 15 hours. In comparison to the induced sample with no NSAAs and the uninduced sample with no NSAAs, the samples that contain the NSAAs are approximately 6-7 fold higher in GFP fluorescence indicating incorporation of the NSAAs into sfGFP. We also quantified the total sfGFP produced from 20 ml of the same culture. Following induction of the cells and overnight growth we lysed the cells using sonication and purified the sfGFP from the extract using a Strep-Tactin column. The sample with pyrrolysine norbornene incorporated into the T216 position produced 9.52±0.03 mg/L and the sfGFP sample with propargyl carbamate incorporated into the T216 position produced 17.84±0.26 mg/L of sfGFP. We also confirmed the site-specific incorporation of the correct NSAA by top-down mass spectrometry to detect the incorporation. The results show >95% incorporation of the NSAA at the correct position.

Materials and Methods

PylRS purification: An overnight culture of BL21(DE3) transformed with pET21aMmPyl was inoculated into 1 L of LB (1:100 dilution) and grown at 250 rpm and 37° C. till OD 0.1 (600 nm). At this point the cells were moved to 42° C. for heat shock treatment and grown at 250 rpm till OD 0.5. Protein production was induced by adding 0.5 mM isopropyl-β-D-thiogalactopyranoside (Sigma, St. Louis, Mo.) and cells were moved to a 33° C. incubator and grown at 250 rpm for 2.5 hours. Cells were harvested at 6,000× g for 15 min at 4° C., washed with 1×PBS buffer, and stored at −80° C. The frozen cell pellet was thawed in lysis buffer (1 OOmM Hepes pH 7.2, 500 mM NaCl, 5 mM BME) and lysed using a homogenizer at 20,00-25,000 psi. After clarification by centrifuging at 12,000×g at 4° C. for 15 min, imidazole was added to the supernatant at a final concentration of 1 OmM and it was loaded onto 2 ml of Ni-NT A agarose slurry (Qiagen) that had been washed twice with 1×PBS. The beads were rotated for 1 hour at room temp and spun down at 5,000×g at 4° C. for 4 min. The beads were washed twice with 10 ml wash buffer (100 mM Hepes pH 7.2, 500 mM NaCl, 50 mM imidazole) by slow rotation at room temp for 25 minutes followed by pelleting the beads as before. The His-tagged AARS was eluted in 1 ml of elution buffer (100 mM Hepes pH 7.2, 500 mM NaCl, 750 mM imidazole) and rotated for 20 minutes. The beads were spun down and the eluate was collected and dialyzed against an excess of dialysis buffer (100 mM Hepes pH 7.2, 10 mM MgCl2, 10 mM KCI) overnight at 4° C. (change buffer once in the middle) to remove imidazole. Protein purity was confirmed by 4-12% NuPAGE SOS-PAGE (Life Technologies, Grand Island, N.Y.). Concentrations were determined by Quick-Start Bradford protein assay kit (Bio-Rad, Hercules, Calif.) and the protein was stored at −80° C.

Cell extract preparation: E. coli cells (BL21 DE3 and C321.flA strain) with and without transformed plasmids were grown in 2×YTPG media (Tryptone 16 g/L, Yeast extract 10 g/L, NaCl 5 g/L, K2HP04 7 g/L KH2P04 3 g/L, glucose 18 g/L) at 34° C. Cells harboring plasmids were induced at OD (600) 0.4 with 0.1% final cone of arabinose (or arabinose and 0.5 mM isopropyl-β-D-thiogalactopyranoside where pEvol and pET21 aMMPyl were both expressed) and grown further till OD 3. Cells were pelleted by centrifuging for 15 min at 6000×g at 4° C., washed twice with cold 830 buffer (10 mM tris-acetate pH 8.2, 14 mM magnesium acetate, 60 mM potassium acetate, 1 mM dithiothreitol)(23), and stored at −80° C. Thawed cells were suspended in 1 ml of 830 buffer per gram cells and lysed using a sonicator (Q-Sonica Model CL-18) using 50% amplitude and three pulses (45 sec on and 59 sec off) on ice. 3 µl of OTT (1 M) was added per ml of sample and the lysate was spun down at 12000×g for 10 min at 4° C. The clarified samples were incubated for 80 min at 120 rpm at 37° C. to optimize the extract activity and centrifuged for 15 min at 15,000×g at 4° C. The supernatant was flash-frozen using liquid nitrogen and stored at −80° C. until use. Total protein concentration of the extracts was approximately 55 mg/ml, as measured by Quick-Start Bradford protein assay kits (Bio-Rad, Hercules, Calif.).

CFPS reaction. CFPS reactions were performed as described previously (35) testing for incorporation of Pyrrolysine Norbornene and Propargyl Carbamate using a modified PANOx-SP system (2). Briefly, 15 µl of CFPS reaction in a 1.5 ml microcentrifuge tube was prepared by mixing the following components: 1.2 mM ATP; 0.85 mM each of GTP, UTP, and CTP; 34.0 µg/ml folinic acid; 170.0 µg/ml of E. coli tRNA mixture; 100 µg/ml T7 RNA polymerase; 2 mM each of 20 standard amino acids; 0.33 mM nicotinamide adenine dinucleotide (NAO); 0.27 mM coenzyme-A (CoA); 1.5 mM spermidine; 1 mM putrescine; 4 mM sodium oxalate; 130 mM potassium glutamate; 10 mM ammonium glutamate; 12 mM magnesium glutamate; 33 mM phosphoenolpyruvate (PEP); 200 ng of sfGFPT216 plasmid, 6.8 µM PylRS (where indicated); 0.045 µM PyltRNA (where indicated); 2 mM Pyrrolysine Norbornene or Propargyl Carbamate (where indicated) and 27% v/v of cell extract. The sample was incubated for 20 h at 30° C.

Quantification of the synthesized sfGFP: Total protein yields were quantified by determining radioactive 14C-Leu incorporation using trichloroacetic acid (TCA) (10). Radioactivity of TCA-precipitated samples was measured using liquid scintillation counting, (MicroBeta2, PerkinElmer, Waltham, Mass.). Active sfGFP protein yields were quantified by measuring fluorescence. 2 µL of CFPS reaction was added in the middle of the flat bottom of 96-well half area black plates along with 48 ul nucleas-free water (Costar 3694; Corning Incorporated, Corning, N.Y.). sfGFP was excited at 485 nm while measuring emission at 528 nm with a 510 nm cut-off filter. The fluorescence of sfGFP was converted to concentration (µg/ml) according to a standard curve described previously (35)

Autoradiography analysis: Radioactive 14C-Gly was added in CFPS reactions. 5 µL of each reaction was heated at 90° C. with 1 OmM OTT and LOS sample loading buffer from Novex (Life Technologies) and loaded onto a 4-12% NuPAGE SOS-PAGE gel. The gel was stained using simply blue safe stain (Invitrogen), destained in water and soaked in Gel Drying Solution (Bio-Rad, Hercules, Calif.) for 30 min, fixed with cellophane films, dried without applying heat overnight in GelAir Dryer (Bio-Rad, Hercules, Calif.), and exposed for 48 hours on a Storage Phosphor Screen (GE Healthcare Biosciences, Pittsburgh, Pa.). The autoradiogram was scanned using a Storm imager (GE Healthcare Biosciences, Pittsburgh, Pa.) and analyzed using Quantity One software (Bio-Rad, Hercules, Calif.).

Preparation of sfGFP proteins in vitro for mass spectrometry: Multiple CFPS reactions were set up (up to 20 reactions per sample) and incubated overnight at 30° C. The following day the samples were combined and purified using 0.2 ml gravity-flow Strep-Tactin Sepharose mini-columns (IBA GmbH, Gottingen, Germany). Eluted protein samples were concentrated using Microcon centrifugal filter columns YM-10 (Millipore, Billerica, Mass.). Concentrations were determined by Quick-Start Bradford protein assay kit (Bio-Rad, Hercules, Calif.). The samples were analyzed by top down mass spectrometry as detailed in the following section.

In vivo amber suppression: pEvolPylRSWT was co-transformed into BL21 cells along with a plasmid that expresses an IPTG inducible form of sfGFP containing a single amber stop codon (sfGFPT216). sfGFP production can take place solely in the presence of the NSAA by its incorporation into the amber stop position at residue 216. For small scale production of sfGFP a single colony from the transformed BL21 cells was inoculated into 5 mls of LB media supplemented with the appropriate antibiotics (Kanamycin and Chloroamphenicol) for overnight growth at 37° C. with rotation. The following morning 6 µl of overnight culture was inoculated into 172 µl of LB media (containing the same antibiotics) into wells of a 96 well plate (black plate clear bottom). The samples were grown with shaking at 37° C. and the OD of the culture was monitored. NSAA (2 mM final concentration) was added at OD 0.15 (as measured by the Synergy H1) and the inducer was added at OD 0.2 (as measured by the Synergy H1). Samples were induced with a final concentration of 5 mM IPTG and 0.1% arabinose. The OD (600 nm) and GFP (excitation 485 nm and emission 528 nm) readings were monitored over a 15 hour time period using a Synergy H1 Hybrid reader from BioTek. Each sample was repeated at a minimum in triplicate and the average and standard deviation of GFP/OD were graphed.

For larger scale production of sfGFP (20 ml) a single colony from the transformed BL21 cells was inoculated into 5 ml of LB media supplemented with the appropriate antibiotics (Kanamycin and Chloroamphenicol) for overnight growth at 37° C. with rotation. The following morning 200 µl of overnight culture was inoculated into 20 ml of LB media (containing the same antibiotics) into a 125 ml glass flask. The samples were grown with shaking at 37° C. and the OD of the culture was monitored. NSAA (2 mM final concentration) was added at OD 0.2 and the inducer was added at OD 0.4. Samples were induced with a final concentration of 5 mM IPTG and 0.1% arabinose. Samples were kept shaking at 250 rpm at 37° C. overnight. Cells were pelleted and lysed using sonication (50% power 45 second pulse followed by 1 minute cooling). The lysate was cleared by centrifugation at 12,000×g for 10 min at 4° C. and C-terminal tagged full-length sfGFP was purified from the lysate using 0.2 ml gravity-flow Strep-Tactin Sepharose mini-columns (IBA GmbH, Gottingen, Germany). Eluted protein samples were concentrated using Microcon centrifugal filter columns YM-10 (Millipore, Billerica, Mass.). Concentrations were determined by Quick-Start Bradford protein assay kit (Bio-Rad, Hercules, Calif.). Each sample was repeated twice and the average and standard error of total sfGFP protein were calculated.

Mass spectrometry: The purified protein was analyzed by nano-capillary LC-MS using a 100 mm×75 µm ID PLRP-S column in-line with an Orbitrap Elite (ThermoFisher, Waltham, Mass.). All MS methods included the following events: 1) FT scan, m/z 400-2,000, 120,000 resolving power and 2) data-dependent MS/MS on the top 2 peaks in each spectrum from scan event 1 using higher-energy collisional dissociation (HCD) with normalized collision energy of 25, isolation width 50 m/z, and detection of ions with resolving power of 60,000. All data were analyzed using QualBrowser, part of the Xcalibur software packaged with the ThermoFisher Orbitrap Elite.

Preparation of NSAAs: $N^6$-(5-Norbornen-2-yloxycarbonyl)-L-Lysine Hydrochloride and $N^6$-(propargyloxycarbonyl)-L-Lysine Hydrochloride were synthesized by the Center for Molecular Innovation & Drug Discovery. The methods are detailed in the supplementary methods section. Both NSAAs were soluble in nuclease-free water. Stock solutions of 500 mM were made for use in experiments.

Plasmids and cloning: Plasmid pEvolPylRSWT[59], plasmids sfGFPWT and sfGFPT216[22], and plasmid STAG (sfGFP D36xK101xE132xD190xE213x)[35] were described previously. 2TAG (sfGFPS2xT216x) was created by introducing an amber codon at the 82 site in sfGFPT216x and 3TAG (sfGFPS2xT216x) was created by introducing an amber codon at the 82 site in sfGFPN212xT216x that has been previously described [35]. The amber codon was introduced at 82 by performing PCR using primers 82-f forward primer and 82-r reverse primer (TABLE 5) with Phusion High-Fidelity DNA polymerase (New England Biolabs, Ipswich, Mass.) at 98° C. for 30 sec, with 30 cycles of 98° C. for 10 sec, 49° C. for 30 sec, and 72° C. for 3 min, and a final extension of 72° C. for 5 min followed by gel extraction of the band and ligation. Plasmid pET21 aMmPyl was created as follows. The wildtype PylRS DNA sequence was amplified using primers AR108 and AR109 (TABLE 5) from pEvolPylRSWT and the PCR product was digested with Not1 and Nde1. This digested product was ligated with vector pET21a (EMO Millipore) that had also been digested with Not1 and Nde1 to get the PylRS gene upstream of a fused C-terminal His tag.

TABLE 5

Oligonucleotides used in Example 3.

| Oligo name | Sequence | SEQ ID |
|---|---|---|
| AR109 | GATATCCATATGGATAAAAAACCACTAA ACACTCTG | 100 |
| AR108 | GGTAGCGCGGCCGCCAGGTTGGTAGAAA TCCCG | 101 |
| AR045 | TGGCGGAAACCCCGGGAATC | 102 |
| GB1 | GCTTTTAGATCTTAATACGACTCACTAT AGGGAGACCGGCTGATGAGTCCGTGAGG ACGAAACGGTACCCGGTACCGTCGGAAA CCTGATCATGTAGATCGAATGGACTCTA AATCCGTTCAGCCGGGTTAGATTCCCGG GGTTTCCGCCAGGAAGCTTACATCCGTC GACCAAAAGC | 103 |
| T7500up | CCGAAGGTAACTGGCTTAGCAGAG | 104 |
| S2-f | TAGAAAGGTGAAGAACTGTTTAC | 105 |
| S2-r | CATATGTATATCTCCTTCTTAAAGTTAA AC | 106 |
| T7 Promoter | TAATACGACTCACTATAGGGAGA | 107 |
| Ribozyme | CCGGCTGATGAGTCCGTGAGGACGAAAC GGTACCCGGTACCGTC | 108 |
| Pyl tRNA | GGAAACCTGATCATGTAGATCGAATGGA CTCTAAATCCGTTCAGCCGGGTIAGATT CCCGGGGTTTCCGCCA | 109 |

Construction of linear DNA templates for expressing Pyl tRNA: A plasmid pY71 GB1f was created to contain the transzyme sequence [21] composed of the DNA sequence of the T7 promoter followed by the hammerhead Ribozyme and the Pyl tRNA. Briefly, a gBlocks GB1 (TABLE 5) was obtained (Integrated DNA technologies, Coralville, Iowa) and digested with Bgl11 and Sal1 and ligated into cloned into pY71 plasmid using Bgl11 and Sal1 restriction sites. The linear DNA template was created by amplifying the transzyme sequence as well as 500 basepairs of upstream sequence in the plasmid using primers T7500 up forward primer (TABLE 5) and AR045 reverse primer. The PCR was performed using Phusion High-Fidelity DNA polymerase (New England Biolabs, Ipswich, Mass.) at 98° C. for 30 sec, with 30 cycles of 98° C. for 40 sec, 58° C. for 40 sec, and 72° C. for 1 min, and a final extension of 72° C. for 5 min. The PCR was purified using the E.Z.N.A. Cycle Pure Kit (Omega biotech) and quantified using a nanodrop 2000c (Thermo Scientific).

Example 4

Methods of Making and Using RF1 Deficient C321.ΔA Strains with Positive Effector Upregulation for the Preparation of Proteins and Sequence-defined Biopolymers Upregulation of positive effector via increased genomic copy number: One method for upregulation of a gene of interest is to increase the copy number of that gene in the organism. Along these lines, we devised a scheme whereby synthetic copies of putative positive effectors of interest would be augmented with an affinity tag (His tag) and placed under the control of a very strong promoter and a synthetic ribosome binding site designed for maximal expression, and inserted into the genome of strain C321.ΔA.705. Putative positive effector 70ufafA, tufB, groL, ackA, frr, cdd, ndk, dsbC were selected for upregulation in strain C321.ΔA.705. Synthetic linear inserts encoding each positive effector of interest as well as a kanamycin resistance cassette were assembled by overlap extension PCR (OE-PCR) from four base component pieces: i) a promoter piece encoding strong promoter LppS, ii) an effector piece encoding the positive effector of interest, iii) a terminator piece encoding a synthetic transcriptional terminator[43] iv) a kan-resist piece encoding a kanamycin resistance cassette. The insert locus (nucleotide 1,422,263 in the genome of C321.ΔA.705) was identified from a bioinformatics search for highly recombinogenic loci. Promoter pieces were PCR-amplified from plasmid pDTT1-LppS-EF-Tu using a forward primer designed to introduce 50 bp of homology to the genomic region upstream of the insert locus and a reverse primer designed to introduce synthetic ribosome binding site sequences and ensure 20 bp of overlap with the adjacent piece. Effector pieces were PCR-amplified from the genome of C321.ΔA.705 using primers designed to ensure 20 bp of overlap with adjacent pieces. Terminator pieces were PCR-amplified from synthetic annealed oligonucleotides using primers designed to ensure 20 bp of overlap with adjacent pieces. Kan-resist pieces were PCR-amplified from plasmid pKD4 using a forward primer designed to ensure 20 bp of overlap with the adjacent piece and a reverse primer designed to introduce 50 bp of homology to the genomic region downstream of the insert locus. DpnI digestion was used to remove contaminating plasmid templates, and each piece was run on a 1% agarose gel (100V, 1 hr) followed by gel extraction of the DNA. Each effector construct was assembled by OE-PCR: promoter/effector/terminator/kan-resist piece DNAs were combined in stoichiometric proportions (160 ng total DNA) along with end primers (TABLE 6). The PCR was performed using Phusion High-Fidelity DNA polymerase (New England Biolabs, Ipswich, Mass.) at 98° C. for 3 min, with 30 cycles of 98° C. for 30 sec, 43° C.

for 30 sec, and 72° C. for 5 min, and a final extension of 72° C. for 10 min. Total PCR products for each construct were run on a 1% agarose gel (100V, 1 hr) and correctly assembled DNAs were excised and extracted from the gel and quantified using a nanodrop 2000c (Thermo Scientific). Each construct was further amplified by PCR using end primers (TABLE 6), with each PCR purified using the E.Z.N.A. Cycle Pure Kit (Omega biotech) and quantified using a nanodrop 2000c (Thermo Scientific). Construct DNA solutions were diluted to 70 ng/µL. C321.ΔA.705 cells were made electrocompetent using established protocols [31], resuspended in 50 µL of construct DNA, and each construct was delivered into cells via electroporation using a Micropulser electroporator (Bio-Rad). Colony PCR was used to identify successful transformants (TABLE 6).

TABLE 6

Primers used in Example 4.

| Oligo name | Sequence | SEQ ID |
|---|---|---|
| rEcoli_homoins_F | CCTCAACTCAGATTAAAATTCGTTTTGTTCAGTGAATGATCTTGCCGGATATCAAAAAAATATTGACAAC | 110 |
| rEcoli_homoins_R | GAAATCTGAAAGAAATAGCCTGCGTATGGCGCAGGCTATGAACAGTGTGTGGTGGAATCGAAATCTCGTGATG | 111 |
| rEcoli_ins_F | CCTCAACTCAGATTAAAATTCG | 112 |
| rEcoli_ins_R | GAAATCTGAAAGAAATAGC | 113 |
| kanR_F | GAAGCGGAACACGTAGAAAG | 114 |
| tufB_promRBS_R | CCTCCTTACTGTTGATTCCTGATGAAATCAATTGTTATCCGCTCACAATTCC | 115 |
| tufB_genomic_F | CAGGAATCAACAGTAAGGAGGCCCCAatgTCTAAAGAAAAGTTTGAACG | 116 |
| tufB_genomicHIS_R | GTGGTGATGGTGATGATGGCCGCTACCGCTCAGAACTTTTGCTACAACG | 117 |
| tufB_HISterm_F | GCCATCATCACCATCACCACTAATTGCCGATAACATTTGACG | 118 |
| tufB_termkanR_R | CTTTCTACGTGTTCCGCTTCAAAGAAAATCACTGATGAGC | 119 |
| tufA_promRBS_R | GTTTTCCTCCTTAAAATGCTTAATATATGAATTGTTATCCGCTCACAATTCC | 120 |
| tufA_genomic_F | GCATTTTAAGGAGGAAAACAgtgTCTAAAGAAAAATTTGAACG | 121 |
| tufA_genomicHIS_R | GTGGTGATGGTGATGATGGCCGCTACCGCCCAGAACTTTAGCAACAACG | 122 |
| tufA_HISterm_F | GCCATCATCACCATCACCACTAATTACACGTTAATTAGTTTTG | 123 |
| tufA_termkanR_R | CTTTCTACGTGTTCCGCTTCATAATTTATTCGTTCTGACAG | 124 |
| groL_promRBS_R | CTGTTACCTCCTTATCTGGGTTGAATTGTTATCCGCTCACAATTCC | 125 |

TABLE 6-continued

Primers used in Example 4.

| Oligo name | Sequence | SEQ ID |
|---|---|---|
| groL_genomic_F | CCAGATAAGGAGGTAACAGatgGCAGCTAAAGACGTAAAATTCG | 126 |
| groL_genomicHIS_R | GTGGTGATGGTGATGATGGCCGCTACCCATCATGCCGCCCATGCCAC | 127 |
| groL_HISterm_F | GCCATCATCACCATCACCACtaaTTGCCCTGCACCTCGCAG | 128 |
| groL_termkanR_R | CTTTCTACGTGTTCCGCTTCGTCGTCCGTGTCTGAATC | 129 |
| ackA_promRBS_R | GACCTCCTTATCTTCCGTTTTGGTGTTAATTGTTATCCGCTCACAATTCC | 130 |
| ackA_genomic_F | CAAAACGGAAGATAAGGAGGTCAAAAatgTCGAGTAAGTTAGTACTGG | 131 |
| ackA_genomicHIS_R | GTGGTGATGGTGATGATGGCCGCTACCGGCAGTCAGGCGGCTCGCGTC | 132 |
| ackA_HISterm_F | GCCATCATCACCATCACCACtgatttcaCACCGCCAGCTCAGC | 133 |
| ackA_termkanR_R | CTTTCTACGTGTTCCGCTTCGGGATCAGCATAATAATACG | 134 |
| dsbC_promRBS_R | ACCCGACCGTCCTTAAGTGACTACCCCTAGGTAATTGTTATCCGCTCACAATTC | 135 |
| dsbC_genomic_F | ACCTAGGGGTAGTCACTTAAGGACGGTCGGGTatgAAGAAAGGTTTTATGTTG | 136 |
| dsbC_genomicHIS_R | GTGGTGATGGTGATGATGGCCGCTACCTTTACCGCTGGTCATTTTTTGG | 137 |
| dsbC_HISterm_F | GGTAGCGGCCATCATCACCATCACCACtaaTTGCCCTGCACCTCGCAG | 138 |
| dsbC_termkanR_R | CTTTCTACGTGTTCCGCTTCGTCGTCCGTGTCTGAATCTTATAC | 139 |
| frr_promRBS_R | CCTATACCTCCTTATTTTCTGTAAATTGTTATCCGCTCACAATTC | 140 |
| frr_genomic_F | TACAGAAAATAAGGAGGTATAGGgtgATTAGCGATATCAGAAAAG | 141 |
| frr_genomicHIS_R | GTGGTGATGGTGATGATGGCCGCTACCGAACTGCATCAGTTCTGCTTC | 142 |
| frr_HISterm_F | GGTAGCGGCCATCATCACCATCACCACtgaTTTCTTGAACGACAAAAACG | 143 |
| frr_termkanR_R | CTTTCTACGTGTTCCGCTTCTGAGACAGAATAAAAAGC | 144 |
| cdd_promRBS_R | AGTATACCTCCTTAATTCCGGATAATTGTTATCCGCTCACAATTC | 145 |
| cdd_genomic_F | ATCCGGAATTAAGGAGGTATACTatgCATCCACGTTTTCAAACC | 146 |

TABLE 6-continued

Primers used in Example 4.

| Oligo name | Sequence | SEQ ID |
|---|---|---|
| cdd_genomicHIS_R | GTGGTGATGGTGATGATGGCCGC TACCAGCGAGAAGCACTCGGTCG | 147 |
| cdd_HISterm_F | GGTAGCGGCCATCATCACCATCA CCACtaaGCCTGGTGCCGGATGC | 148 |
| cdd_termkanR_R | CTTTCTACGTGTTCCGCTTCAAT TTCGACACCAGGAGAGG | 149 |
| ndk_promRBS_R | TTAGAGGACCTCCTTATATTTAA GTTTGTAATTGTTATCCGCTCAC AATTC | 150 |
| ndk_genomic_F | ACAAACTTAAATATAAGGAGGTC CTCTAAatgGCTATTGAACGTAC TTTTTCC | 151 |
| ndk_genomicHIS_R | GTGGTGATGGTGATGATGGCCGC TACCACGGGTGCGCGGGCACACT TCG | 152 |
| ndk_HISterm_F | GGTAGCGGCCATCATCACCATCA CCACtaaTAATTTCGTAAATGC | 153 |
| ndk_termkanR_R | CTTTCTACGTGTTCCGCTTCGGG TTGAAAAAAGAAACG | 154 |
| infB_promRBS_R | TTTATACCTCCTTATTCTAGTTT GTTGTGTGGGTCAATTGTTATCC GCTCACAATTC | 155 |
| infB_RBSgenomic_F | GACCCACACAACAAACTAGAATA AGGAGGTATAAAatgACAGATGT AACGATTAAAACG | 156 |
| infB_genomicHIS_R | GTGGTGATGGTGATGATGGCCGC TACCAGCAATGGTACGTTGGATC TCG | 157 |
| infB_HISterm_F | GGTAGCGGCCATCATCACCATCA CCACtaaGGTTTTTAGGGTTCCA TGC | 158 |
| infB_termkanR_R | CTTTCTACGTGTTCCGCTTCAAA TTAATTTCAGGTGGAAGG | 159 |
| poseff_cPCR1_F | CTGCTCCCGGTTTTAGTTCC | 160 |
| groL_cPCR1_R | TACCGATCTCTTCAGAGATC | 161 |
| tufX_cPCR1_R | CACTTCAGATTCGAACTTGG | 162 |
| ackA_cPCR1_R | GGGTACCTTCTTTGTTGATG | 163 |
| dsbC_cPCR1_R | GGAATTCTTTCATCTCTTTCG | 164 |
| frr_cPCR1_R | ACGTTGATTTTCAGTGTACG | 165 |
| cdd_cPCR1_R | TTCAACAGAATTAACGCTCC | 166 |
| ndk_cPCR1_R | CAAAGAAATAAGCGATTTCG | 167 |
| infB_cPCR1_R | GACGCAGGATAACTTTATGG | 168 |
| poseff_cPCR2_F | CGAGAAAGTATCCATCATGG | 169 |
| poseff_cPCR2_R | ATCTGAAAGAAATAGCCTGC | 170 |

Genomic synthetic positive effector gene inserts are functional: 5 mL cultures (LB, 50 µg/mL carbenicillin, 50 µg/mL kanamycin) of each colony PCR-confirmed transformant were supplemented with 1 mM IPTG and allowed to grow for 20 h at 32° C. Soluble protein samples were prepared from each culture, separated by size via SDS-PAGE (12% polyacrylamide, 3 h), and transferred to IVDF membrane (400 mA, 45 minutes). Western blots using an antibody against each effector protein's His-tag confirmed that the effector proteins are being synthesized at the correct size in each effector strain.

Figure 17:
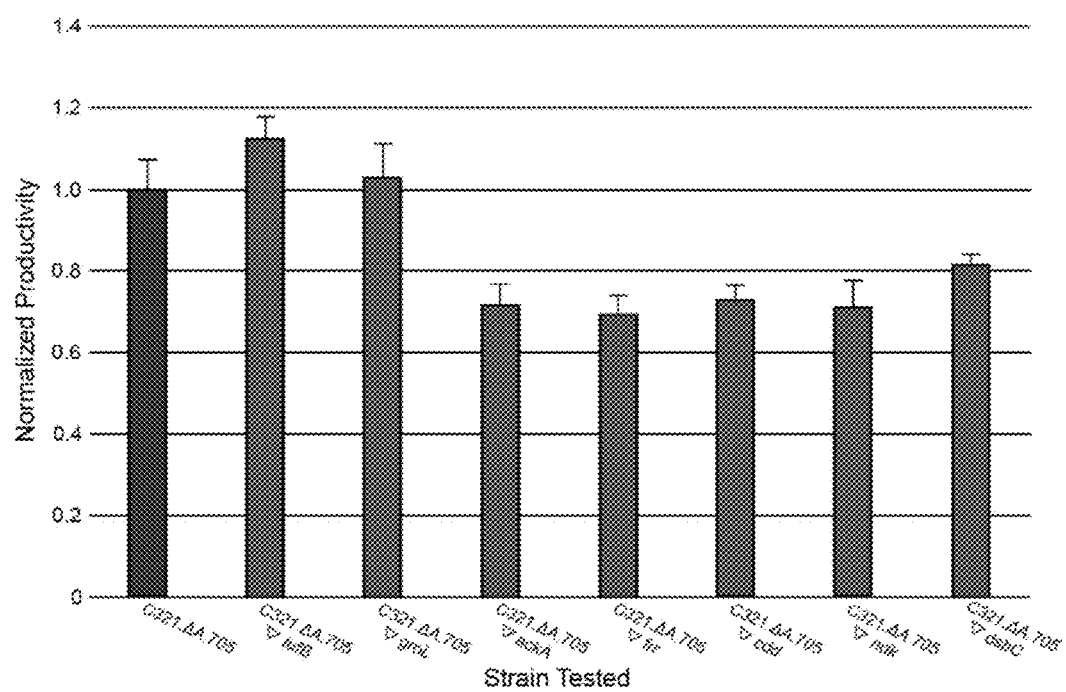
FIG. 17 shows a comparison of cell-free synthesized sfGFP using extracts generated from genomic insertion mutants (tufB, groL, ackA, frr, cdd, ndk, and dsbC) relative to parental strain (C321.ΔA.705). Protein yields were normalized to those obtained from C321.ΔA.705.

Upregulation of putative positive effectors increase strain yields in CFPS: Confirmed positive effector strains were harvested, with S30 lysates prepared using established protocols. To assess strain productivities, CFPS reactions were assembled using each lysate, directed to synthesize sfGFP for 20 h at 30° C. 2 µL of each reaction were diluted in 48 µL nanopure water, and fluorescence was measured on Synergy2 plate reader. Based on relative productivities normalized to C321.ΔA.705 yields, strains overexpressing elongation factor (tufB) and the protein chaperone (groL) show marked increases in CFPS productivity (FIG. 17). These results suggest that augmenting protein translation factors and enhancing protein folding in the source strain can further improve CFPS.

REFERENCES

1. Carlson, E. D. et al. *Biotechnology advances* 30, 1185 (2012).
2. Jewett, M. C. & Swartz, J. R. *Biotechnology and bioengineering* 86, 19 (2004).
3. Caschera, F. & Noireaux, V. *Biochimie* 99, 162 (2014).
4. Dudley, Q. M. et al. *Biotechnology journal* 10, 69 (2015).
5. Chappell, J. et al. *Nucleic acids research* 41, 3471 (2013).
6. Takahashi, M. K. et al. *Methods* (2015).
7. Zawada, J. F. et al. *Biotechnology and bioengineering* 108, 1570 (2011).
8. Hong, S. H. et al. *Chembiochem: a European journal of chemical biology* 16, 844 (2015).
9. Yang, W. C. et al. *Biotechnology and bioengineering* 104, 1047 (2009).
10. Michel-Reydellet, N., et al. *Journal of molecular microbiology and biotechnology* 9, 26 (2005).
11. Raines, R. T. *Chemical reviews* 98, 1045 (1998).
12. Jiang, X. et al. *Journal of bioscience and bioengineering* 93, 151 (2002).
13. Airen, I. O. in Stanford University, Vol. PhD (Stanford University (USA), 2011).
14. Michel-Reydellet, N., et al. *Metabolic engineering* 6, 197 (2004).
15. Calhoun, K. A. & Swartz, J. R. *Journal of biotechnology* 123, 193 (2006).
16. Jewett, M. C. et al. *Molecular systems biology* 4, 220 (2008).
17. Kim, T. W. et al. *Biotechnol Bioproc E* 13, 464 (2008).
18. Hong, S. H. et al. *Frontiers in chemistry* 2, 34 (2014).
19. Liu, C. C. & Schultz, P. G. *Annual review of biochemistry* 79, 413 (2010).
20. Goerke, A. R. & Swartz, J. R. *Biotechnology and bioengineering* 102, 400 (2009).
21. Albayrak, C. & Swartz, J. R. *Nucleic acids research* 41, 5949 (2013).
22. Bundy, B. C. & Swartz, J. R. *Bioconjugate chemistry* 21, 255 (2010).
23. Sun, S. B. et al. *Chembiochem: a European journal of chemical biology* 15, 1721 (2014).
24. Lu, Y. et al. *Biotechnology and bioengineering* 110, 2073 (2013).
25. Ugwumba, I. N. et al. *Journal of the American Chemical Society* 133, 326 (2011).

26. Des Soye, B. J. et al. *Current opinion in chemical biology* 28, 83 (2015).
27. Chin, J. W. *Annual review of biochemistry* 83, 379 (2014).
28. Young, T. S. & Schultz, P. G. The *Journal of biological chemistry* 285, 11039 (2010).
29. Loscha, K. V. et al. *Angewandte Chemie (International ed. in English)* 51, 2243 (2012).
30. Johnson, D. B. et al. *Nature chemical biology* 7, 779 (2011).
31. Lajoie, M. J. et al. *Science* 342, 357 (2013).
32. Wang, H. H. & Church, G. M. *Methods in enzymology* 498, 409 (2011).
33. Jewett, M. C. et al. *Journal of bacteriology* 191, 1083 (2009).
34. Young, T. S. et al. *Journal of molecular biology* 395, 361 (2010).
35. Hong, S. H. et al. *ACS synthetic biology* 3, 398 (2014).
36. Chu, H.-S. et al. *Enzyme Microb Technol* 46, 87 (2010).
37. Sambrook, J. et al. Molecular Cloning, A Laboratory Manual, Cold Spring Harbor Laboratory Press. ColdSS Spring Harbor, NY. (1989).
38. Swartz, J. R. et al. *Methods in molecular biology* 267, 169 (2004).
39. Kwon, Y. C. & Jewett, M. C. *Scientific reports* 5, 8663 (2015).
40. Gallagher, R. R. et al. *Nucleic acids research* 43, 1945 (2015).
41. Schoborg, J. A. et al. *Biotechnology journal* 9, 630 (2014).
42. Chu, H. S. et al. *Protein expression and purification* 74, 298 (2010).
43. Chen, Y. J. et al. *Nat Methods* 10, 659 (2013).
44. Borja, G. et al., *Microb. Cell Fact.* 11, 132 (2012).
45. Lehman, I. R. et al. *J. Biol. Chem.* 237, 829 (1962).
46. Chizzolini, F. et al. *ACS Synth. Biol.* 3, 363 (2014).
47 Zawada, J. & Swartz, J. *Biotechnol. Bioeng.* 89, 407 (2005).
48. Chatterjee, A. et al. *Biochemistry* 52, 1828 (2013).
49. Voloshin, A. M. & Swartz, J. R. *Biotechnol. Bioeng.* 91, 516 (2005).
50. Kim, D.-M. & Choi, C.-Y. *Biotechnol. Prog.* 12, 645 (1996).
51. Liu, Y. et al. *ACS Synth. Biol.* 4, 454 (2015).
52. Wang, H. H. *Nature* 460, 894 (2009).
53. Yang, J. et al. *Biotechnology progress* 20, 1689 (2004).
54. Fritz, B. R. & Jewett, M. C. *Nucleic acids research* 42, 6774 (2014).
55. Gibson, D. G. et al. *Nat. Methods* 6, 343 (2009).
56. Kim, D.-M. & Swartz, J. R. *Biotechnol. Bioeng.* 74, 343 (2009).
57. Chatterjee, A. et al. *Angew. Chem. Int. Ed.* 52, 5106 (2013).
58. Chen, J. et al. *J. Mol. Microbiol. Biotechnol.* 4, 255 (2002).
59. Plass, T. et al. *Angew. Chem. Int. Ed.* 51, 4166 (2012).

All references, including publications, patent applications, and patents, cited herein are hereby incorporated by reference to the same extent as if each reference were individually and specifically indicated to be incorporated by reference and were set forth in its entirety

What is claimed:

1. A platform for preparing a sequence defined biopolymer or a protein in vitro, the platform comprising a cellular extract from a genomically recoded E. coli strain comprising:
   (i) a genetic knock-out mutation in release factor 1 (RF-1) or a genetic homolog thereof; and
   (ii) a genetic knock-out mutation in endA.

2. The platform of claim 1, wherein the strain is (a) E. coli strain C321.ΔprfA, (b) E. coli strain rec13.ΔprfA, or a derivative of either (a) or (b), further modified to comprise the genetic knock-out mutations as defined in (i) and (ii).

3. The platform of claim 1, wherein the cellular extract from the strain is capable of preparing a sequence defined biopolymer or a protein in greater yield and/or purity than a strain that does not have the genetic knock-out mutations as defined in (i) and (ii).

4. The platform of claim 1, wherein the sequence defined biopolymer or the protein comprises a product prepared from the platform that includes at least 5 unnatural amino acids.

5. The platform of claim 1 further comprising an orthogonal translation system component configured to incorporate unnatural amino acids.

6. The platform of claim 5, wherein the orthogonal translation system component is expressed from a plasmid present in the genomically recoded strain, expressed from an integration site in the genome of the genetically recoded strain, co-expressed from both a plasmid present in the genomically recoded strain and an integration site in the genome of the genetically recoded strain, expressed in an in vitro transcription and translation reaction, or added exogenously.

7. The platform of claim 1 further comprising T7 RNA polymerase.

8. The platform of claim 7, wherein the T7 RNA polymerase is expressed from a plasmid present in the genetically recoded strain or an integration site in the genome of the genetically recoded strain.

9. The platform of claim 1, wherein the cellular extract from the genomically recoded strain is a component in a reaction mixture.

10. A method for cell-free protein synthesis of a sequence defined biopolymer or a protein in vitro, the method comprising contacting a RNA template encoding the sequence defined biopolymer with a reaction mixture comprising the platform of claim 1.

11. The method of claim 10, wherein the cellular extract from the strain of the genomically recoded strain is capable of preparing the sequence defined biopolymer or the protein in greater yield and/or purity than a strain that (i) is not deficient in release factor 1 (RF-1), and (ii) is not deficient in endA.

12. The method of claim 10, wherein the sequence defined biopolymer or the protein comprises a product prepared from the method that includes at least 5 unnatural amino acids.

13. The method of claim 10, wherein the sequence defined biopolymer encoded by the RNA template comprises at least 5 unnatural amino acids and wherein a product prepared from the method includes at least 80% of the encoded unnatural amino acids.

14. The method of claim 10, wherein the sequence defined biopolymer encoded by the RNA template comprises at least 5 unnatural amino acids and wherein at least 80% of a plurality of products prepared from the method include 100% of the encoded unnatural amino acids.

15. The method of claim 10, wherein at least 80% of a plurality of products prepared from the method are full length.

16. The method of claim 10, wherein the sequence defined biopolymer or the protein encodes a therapeutic product, a diagnostic product, a biomaterial product, an adhesive product, a biocomposite product, or an agricultural product.

17. A platform for preparing a sequence defined biopolymer or a protein in vitro, the platform comprising a cellular extract from a genomically recoded E. coli strain comprising a genetic knock-out mutation in release factor 1 (RF-1) or a genetic homolog thereof and the genomically recoded strain further comprising at least one additional upregulated gene product, wherein the at least one addition upregulated gene product improves energy supply, chaperone levels, translation function, ribosome recycling, or any combination thereof, and the at least one additional upregulated gene product comprises a member selected from the group consisting of ackA, ndk, pykF, cdd, dsbC, dnaK, dnaJ, crpE, tig, groS, groL, infA, infB, fusA, efp, lepA, tufB, hslR, ffr, and any combination thereof.

18. The platform of claim 17, wherein the strain is (a) E. coli strain C321.ΔprfA, (b) E. coli strain rec13.ΔprfA, or a derivative of either (a) or (b)), further modified to comprise the at least one additional upregulated gene product.

19. The platform of claim 17, wherein a cellular extract from the strain is capable of preparing a sequence defined biopolymer or a protein in greater yield and/or purity than a strain that (i) is not deficient in release factor 1 (RF-1), and (ii) does not have the at least one additional upregulated gene product.

20. The platform of claim 17, wherein the at least one additional upregulated gene product improves chaperone levels or translation function.

21. A method for cell-free protein synthesis of a sequence defined biopolymer or a protein in vitro, the method comprising contacting a RNA template encoding the sequence defined biopolymer with a reaction mixture comprising the platform of claim 17.

22. A platform for preparing a sequence defined biopolymer or a protein in vitro, the platform comprising a cellular extract from a genomically recoded *E. coli* strain comprising:
   (i) a genetic knock-out mutation in release factor 1 (RF-1) or a genetic homolog thereof;
   (ii) a genetic knock-out mutation in endA; and
   (iii) a genetic knock-out mutation in a gene selected from the group consisting of mazF, ma, mb, rne, gor, Ion, ompT, gdhA, gshA, sdaA, sdaB, speA, WaaL, tnaA, glpK, and any combination thereof.

23. A platform for preparing a sequence defined biopolymer or a protein in vitro, the platform comprising a cellular extract from a genomically recoded *E. coli* strain comprising:
   (i) a genetic knock-out mutation in release factor 1 (RF-1) or a genetic homolog thereof;
   (ii) a genetic knock-out mutation in endA; and
   (iii) a genetic knock-out mutation in a gene selected from the group consisting of mazF, rne, gor, and a combination thereof.

* * * * *

```
SEQUENCE LISTING

<160> NUMBER OF SEQ ID NOS: 170

<210> SEQ ID NO 1
<211> LENGTH: 90
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 1
gctgattttc tgaccgtaca tggtctgtgg ccaggaatgt aaatgctgat gtattgccta      60
aatcggttgc tgcccgtggt gttgatgaac                                       90

<210> SEQ ID NO 2
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 2
gctctggctg atgtcaggac gggtagtcac gcttcagtta aatgcgcact tcctgcggct      60
ctttcataaa gcggcgggta atgcgacga                                        89

<210> SEQ ID NO 3
```

```
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 3
attttgtcac catcgacagt gccagcacag aagatatgga ttaactgact tttcgctaag      60
gcgttgccgg atgacaaact tcagctgat                                       89

<210> SEQ ID NO 4
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 4
ttgattgcgt tgtacaagga acacacagac acatacctgt tttgttgttt cagttagaaa      60
ggactcagga caacagctgg acgatgtcc                                       89

<210> SEQ ID NO 5
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 5
cggtaaaagt ccacgctgac gcgcccggta cgttttattg ctaactgaaa aattaactgg      60
cagggcaaaa aaggcgttgt tgatctgca                                       89

<210> SEQ ID NO 6
<211> LENGTH: 90
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 6
tggacaactc tcggcagccg aggtggcaat atggtcgcgc aggactggat ggattccagt      60
aaccccggaa cctggacgga tgaaagtaga                                      90

<210> SEQ ID NO 7
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
```

```
<222> LOCATION: (1)..(4)
<223> OTHER INFORMATION: Phosphorylated

<400> SEQUENCE: 7
aactctgctt ccgctttctc ttttgcctct ttcggcatct ttcagttagt cgattttgcg    60
cttcagggct tcgttttcgt ccggcgcgt                                      89

<210> SEQ ID NO 8
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 8
gttttgatac cactatcaat aaattcaact gggaaacgtt gtaactgaag ccgtaccgcc    60
tatatcgacc gtattcatac ttcctatga                                      89

<210> SEQ ID NO 9
<211> LENGTH: 88
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 9
tgcgcttcca tccgtcagtt aacctttcca ttctcaaatt ctaactgatt tgaacaaacc    60
ttcaaaaatg ccctgactac tctgccga                                       88

<210> SEQ ID NO 10
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 10
tctacagcaa aacttattat tccatcggcg gcggttttat ctaactgaga agaacactt     60 ggtcaggatg ctgccaacga agtaagcgt                                      89

<210> SEQ ID NO 11
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 11
acagccagac ttactactct attggcggtg gctttatcgt ttaactgaga gcattttggc    60
```
cagcaggata gcgcaccggt tgaagttcc                                              89

<210> SEQ ID NO 12
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 12
atcttctcaa tgaccagata gaccttgtgc cccatcttct ctcagttata atgccaggcg           60
gatatattcg cggtctttat aaccgttgc                                              89

<210> SEQ ID NO 13
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 13
gatgcaccaa acagataagg aatgacccaa ccgaaacgat atcagttagc ggataacgcg           60
gaaatagccc gcagaaattt tctctttgg                                              89

<210> SEQ ID NO 14
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 14
accttgaggg attagaacgc ggtattgaag aagttggtcc gtaactgagt gccgtatatc           60
gttgcaacca tcaccagtaa ctctgcagg                                              89

<210> SEQ ID NO 15
<211> LENGTH: 89
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(4)
<223> OTHER INFORMATION: Phosphorylated

<400> SEQUENCE: 15
gcaccaaagt gaagtggatc ctcgaccatg tggaaggctc ttaactgacg tgcacgtcgt           60
ggtgaattgc tgtttggtac ggttgatac                                              89

<210> SEQ ID NO 16
<211> LENGTH: 25
<212> TYPE: DNA
<213> ORGANISM: Artificial Sequence

```
<220> FEATURE:
<223> OTHER INFORMATION: Primer

<400> SEQUENCE: 16
gtacatggtc tgtggccagg attgc                                              25

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
ggccaggaat gtaaatgctg atgta                                              25

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
tggcatgact tcacttagtt tagc                                               24

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
gccgcaggaa gtgcgcattc agtcc                                              25

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
gccgcaggaa gtgcgcattt aactga                                             26

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
cagtgcgcgg tattgatcca gatcgc                                             26

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
ccagcacaga agatatggat gacgcc                                             26
```

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
ccagcacaga agatatggat taactga                                27

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
tcactttcag gctgccagtc accgg                                  25

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
ctgttgtcct gagtcctttc atgtac                                 26

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
ctgttgtcct gagtcctttc taactga                                27

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
ggctttaatg agttgtaatt cctctg                                 26

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
cccggtacgt tttattgcgg atgt                                   24

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
cccggtacgt tttattgcta actga                                              25

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gctggcgctg gtaatttcgg cgtca                                              25

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
cagccgaggt ggcaatatgg tcgat                                              25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
cagccgaggt ggcaatatgg tcgcg                                              25

<210> SEQ ID NO 33
<211> LENGTH: 26
<212> TYPE: DNA
<213> ORGANISM: Artificial Sequence
<220> FEATURE:
<223> OTHER INFORMATION: Primer

<400> SEQUENCE: 33
gagttcaaaa tcttcataac gataac                                             26

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
ctgaagcgca aaatcgacgc ggcg                                               24

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
ctgaagcgca aaatcgacta actga                                              25

<210> SEQ ID NO 36

```
<211> LENGTH: 26
<212> TYPE: DNA
<213> ORGANISM: Artificial Sequence
<220> FEATURE:
<223> OTHER INFORMATION: Primer

<400> SEQUENCE: 36
agcgggtttt tcacgcccac tttcgc                                      26

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
ttcaactggg aaacgttgat cgcc                                        24

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
ttcaactggg aaacgttgta actga                                       25

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
tgcaacattt cgtccatacc aaagc                                       25

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
cctttccatt ctcaaattcc tcggc                                       25

<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
cctttccatt ctcaaattct aactga                                      26

<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
```
ctgccgccaa atgaaaggcc cttac                                    25

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
atcggcggcg gttttatcgt cgat                                     24

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
atcggcggcg gttttatcta actga                                    25

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
caagacccgc agcagccatt gaacag                                   26

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
ggcggtggct ttatcgttga tgaa                                     24

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
ggcggtggct ttatcgttta actga                                    25

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
tacctgtccg gcgaccgggt cacac                                    25

<210> SEQ ID NO 49
<211> LENGTH: 27
<212> TYPE: DNA

```
<213> ORGANISM: Artificial Sequence
<220> FEATURE:
<223> OTHER INFORMATION: Primer

<400> SEQUENCE: 49
gaatatatcc gcctggcatt aattggc                                    27

<210> SEQ ID NO 50
<211> LENGTH: 28
<212> TYPE: DNA
<213> ORGANISM: Artificial Sequence
<220> FEATURE:
<223> OTHER INFORMATION: Primer

<400> SEQUENCE: 50
gaatatatcc gcctggcatt ataactga                                   28

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
cggtgattac cgtcggatgc ggcag                                      25

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
tatttccgcg ttatccgcaa ttac                                       24

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
tatttccgcg ttatccgcta actga                                      25

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
aaatcctctt cgcgcagaat ttccagc                                    27

<210> SEQ ID NO 55
<211> LENGTH: 27
<212> TYPE: DNA
<213> ORGANISM: Artificial Sequence
<220> FEATURE:
<223> OTHER INFORMATION: Primer

<400> SEQUENCE: 55
ggtattgaag aagttggtcc gaataac                                    27
```

<210> SEQ ID NO 56
<211> LENGTH: 28
<212> TYPE: DNA
<213> ORGANISM: Artificial Sequence
<220> FEATURE:
<223> OTHER INFORMATION: Primer

<400> SEQUENCE: 56
ggtattgaag aagttggtcc gtaactga                                        28

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57
ctaccgccag acgctccatc gcgcc                                           25

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
gaccatgtgg aaggctctcg cgag                                            24

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
gaccatgtgg aaggctctta actga                                           25

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
caaacagcgc ggcctgctgg tcacc                                           25

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
tgatctgcaa agcatcattt cg                                              22

<210> SEQ ID NO 62
<211> LENGTH: 25
<212> TYPE: DNA
<213> ORGANISM: Artificial Sequence
<220> FEATURE:

<223> OTHER INFORMATION: Primer

<400> SEQUENCE: 62
ttgcctcacg taaccagtgt tgata                                        25

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
cataacggct gtacatacgg aacag                                        25

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
gggcgtaagt cgaccggctg cta                                          23

<210> SEQ ID NO 65
<211> LENGTH: 31
<212> TYPE: DNA
<213> ORGANISM: Artificial Sequence
<220> FEATURE:
<223> OTHER INFORMATION: Primer

<400> SEQUENCE: 65
ttctccatat gtatatctcc ttcttaaagt t                                 31

<210> SEQ ID NO 66
<211> LENGTH: 28
<212> TYPE: DNA
<213> ORGANISM: Artificial Sequence
<220> FEATURE:
<223> OTHER INFORMATION: Primer

<400> SEQUENCE: 66
atatacatat ggagaaaaaa atcactgg                                     28

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
cggtcgactt acgccccgcc ctg                                          23

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gtttctctgc ttcccttctc ttct                                         24

<210> SEQ ID NO 69
<211> LENGTH: 25
<212> TYPE: DNA
<213> ORGANISM: Artificial Sequence
<220> FEATURE:
<223> OTHER INFORMATION: Primer

<400> SEQUENCE: 69
ctgctggacc acctgaaacg tggca                                       25

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
ctgaaaggcg atcgttcttt ctatg                                       25

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
gtaaagagcc cgtatttacg cttgc                                       25

<210> SEQ ID NO 72
<211> LENGTH: 26
<212> TYPE: DNA
<213> ORGANISM: Artificial Sequence
<220> FEATURE:
<223> OTHER INFORMATION: Primer

<400> SEQUENCE: 72
atgtaccgtt atttgtctat tgctgc                                      26

<210> SEQ ID NO 73
<211> LENGTH: 26
<212> TYPE: DNA
<213> ORGANISM: Artificial Sequence
<220> FEATURE:
<223> OTHER INFORMATION: Primer

<400> SEQUENCE: 73
ctgacaaccc ctattgcgat cagctc                                      26

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
gtgctggtgc gtactgcaat cagcc                                       25

<210> SEQ ID NO 75
<211> LENGTH: 25
<212> TYPE: DNA
<213> ORGANISM: Artificial Sequence
<220> FEATURE:
<223> OTHER INFORMATION: Primer

<400> SEQUENCE: 75
taaacactat gattacatcg ccatc        25

<210> SEQ ID NO 76
<211> LENGTH: 25
<212> TYPE: DNA
<213> ORGANISM: Artificial Sequence
<220> FEATURE:
<223> OTHER INFORMATION: Primer

<400> SEQUENCE: 76
gcaagccgtt cgtgaagtaa tgacc        25

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
tactcgcgtt gccgtggacg tttatg        26

<210> SEQ ID NO 78
<211> LENGTH: 26
<212> TYPE: DNA
<213> ORGANISM: Artificial Sequence
<220> FEATURE:
<223> OTHER INFORMATION: Primer

<400> SEQUENCE: 78
tgacccgcgt ggtggttgac gtgtac        26

<210> SEQ ID NO 79
<211> LENGTH: 25
<212> TYPE: DNA
<213> ORGANISM: Artificial Sequence
<220> FEATURE:
<223> OTHER INFORMATION: Primer

<400> SEQUENCE: 79
gtgaaaactc gtgaagcaca gggcc        25

<210> SEQ ID NO 80
<211> LENGTH: 25
<212> TYPE: DNA
<213> ORGANISM: Artificial Sequence
<220> FEATURE:
<223> OTHER INFORMATION: Primer

<400> SEQUENCE: 80
gaacatatgc tgacctttat gcgcg        25

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
cgtagctact atgcgttagc cgag        24

<210> SEQ ID NO 82
<211> LENGTH: 25

```
<212> TYPE: DNA
<213> ORGANISM: Artificial Sequence
<220> FEATURE:
<223> OTHER INFORMATION: Primer

<400> SEQUENCE: 82
aggttgggta gaacacgacc caatg                                              25

<210> SEQ ID NO 83
<211> LENGTH: 34
<212> TYPE: DNA
<213> ORGANISM: Artificial Sequence
<220> FEATURE:
<223> OTHER INFORMATION: Primer

<400> SEQUENCE: 83
tcgatcccgc gaaattaata cgactcacta tagg                                    34

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
caaaaaaccc ctcaagaccc gttta                                              25

<210> SEQ ID NO 85
<211> LENGTH: 25
<212> TYPE: DNA
<213> ORGANISM: Artificial Sequence
<220> FEATURE:
<223> OTHER INFORMATION: Primer

<400> SEQUENCE: 85
ccgaaggtaa ctggcttcag cagag                                              25

<210> SEQ ID NO 86
<211> LENGTH: 29
<212> TYPE: DNA
<213> ORGANISM: Artificial Sequence
<220> FEATURE:
<223> OTHER INFORMATION: Primer

<400> SEQUENCE: 86
tggtccggcg gagggatttt gaacccctg                                          29

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
cactatgctt aaggtactca tatg                                               24

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
```
cgatctccac tagatgtcga c                                              21

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
tagttattgc tcagcggtgg                                                20

<210> SEQ ID NO 90
<211> LENGTH: 18
<212> TYPE: DNA
<213> ORGANISM: Artificial Sequence
<220> FEATURE:
<223> OTHER INFORMATION: Primer

<400> SEQUENCE: 90
gtcccgggtt atgggccc                                                  18

<210> SEQ ID NO 91
<211> LENGTH: 21
<212> TYPE: DNA
<213> ORGANISM: Artificial Sequence
<220> FEATURE:
<223> OTHER INFORMATION: Primer

<400> SEQUENCE: 91
gttcatgtct tcgcggccgc a                                              21

<210> SEQ ID NO 92
<211> LENGTH: 43
<212> TYPE: DNA
<213> ORGANISM: Artificial Sequence
<220> FEATURE:
<223> OTHER INFORMATION: Primer

<400> SEQUENCE: 92
ggtcgcgggg ttgggcccag caaaggtgaa gaactgttta ccg                      43

<210> SEQ ID NO 93
<211> LENGTH: 47
<212> TYPE: DNA
<213> ORGANISM: Artificial Sequence
<220> FEATURE:
<223> OTHER INFORMATION: Primer

<400> SEQUENCE: 93
tttgctcatg gtaccatctc cttcttaaag ttaaacaaaa ttatttc                  47

<210> SEQ ID NO 94
<211> LENGTH: 211
<212> TYPE: DNA
<213> ORGANISM: Artificial Sequence
<220> FEATURE:
<223> OTHER INFORMATION: Primer

<400> SEQUENCE: 94
cactatgctt aaggtactca tatggattac aaggatcatg acggtgatta caaggatcat    60
gacattgatt acaaggatga cgacgataag taccatggac ctgcaatagt tccgggctag   120
ggcgttcgtt ccgggtgtag gtgttcatgt cttcgcggcc gcatggagcc atccgcagtt   180
cgaaaaataa gtcgacatct agtggagatc g                                  211

<210> SEQ ID NO 95
<211> LENGTH: 185
<212> TYPE: DNA
<213> ORGANISM: Artificial Sequence
<220> FEATURE:
<223> OTHER INFORMATION: Primer

<400> SEQUENCE: 95

```
gttcatgtct tcgcggccgc atcggcgtgg agccacccgc agttcgagaa aggtggaggt    60
tccggaggtg gatcgggagg ttcggcgtgg agccacccgc agttcgaaaa ataataagtc   120
gaccggctgc taacaaagcc cgaaaggaag ctgagttggc tgctgccacc gctgagcaat   180
aacta                                                              185
```

<210> SEQ ID NO 96
<211> LENGTH: 182
<212> TYPE: DNA
<213> ORGANISM: Artificial Sequence
<220> FEATURE:
<223> OTHER INFORMATION: Primer

<400> SEQUENCE: 96

```
gtcccgggtt atgggccctc ggcgtggagc cacccgcagt tcgagaaagg tggaggttcc    60
ggaggtggat cgggaggttc ggcgtggagc cacccgcagt tcgaaaaata ataagtcgac   120
cggctgctaa caaagcccga aggaagctg agttggctgc tgccaccgct gagcaataac   180
ta                                                                 182
```

<210> SEQ ID NO 97
<211> LENGTH: 20
<212> TYPE: PRT
<213> ORGANISM: Artificial Sequence
<220> FEATURE:
<223> OTHER INFORMATION: Elastin-like polypeptide

<400> SEQUENCE: 97

Val Pro Gly Val Gly Val Pro Gly Val Gly Val Pro Gly Val Gly Val
1               5                   10                  15

Pro Gly Val Gly
            20

<210> SEQ ID NO 98
<211> LENGTH: 20
<212> TYPE: PRT
<213> ORGANISM: Artificial Sequence
<220> FEATURE:
<223> OTHER INFORMATION: Elastin-like polypeptide
<220> FEATURE:
<221> NAME/KEY: MISC_FEATURE
<222> LOCATION: (5)..(5)
<223> OTHER INFORMATION: "Xaa" is any nonstandard amino acid

<400> SEQUENCE: 98

Val Pro Gly Val Xaa Val Pro Gly Val Gly Val Pro Gly Val Gly Val
1               5                   10                  15

Pro Gly Val Gly
            20

<210> SEQ ID NO 99
<211> LENGTH: 20
<212> TYPE: PRT
<213> ORGANISM: Artificial Sequence
<220> FEATURE:

```
<223> OTHER INFORMATION: Elastin-like polypeptide
<220> FEATURE:
<221> NAME/KEY: MISC_FEATURE
<222> LOCATION: (5)..(5)
<223> OTHER INFORMATION: "Xaa" is any nonstandard amino acid
<220> FEATURE:
<221> NAME/KEY: MISC_FEATURE
<222> LOCATION: (10)..(10)
<223> OTHER INFORMATION: "Xaa" is any nonstandard amino acid
<220> FEATURE:
<221> NAME/KEY: MISC_FEATURE
<222> LOCATION: (15)..(15)
<223> OTHER INFORMATION: "Xaa" is any nonstandard amino acid
<220> FEATURE:
<221> NAME/KEY: MISC_FEATURE
<222> LOCATION: (20)..(20)
<223> OTHER INFORMATION: "Xaa" is any nonstandard amino acid

<400> SEQUENCE: 99

Val Pro Gly Val Xaa Val Pro Gly Val Xaa Val Pro Gly Val Xaa Val
1               5                   10                  15

Pro Gly Val Xaa
            20

<210> SEQ ID NO 100
<211> LENGTH: 36
<212> TYPE: DNA
<213> ORGANISM: Artificial Sequence
<220> FEATURE:
<223> OTHER INFORMATION: Primer

<400> SEQUENCE: 100
gatatccata tggataaaaa accactaaac actctg                             36

<210> SEQ ID NO 101
<211> LENGTH: 33
<212> TYPE: DNA
<213> ORGANISM: Artificial Sequence
<220> FEATURE:
<223> OTHER INFORMATION: Primer

<400> SEQUENCE: 101
ggtagcgcgg ccgccaggtt ggtagaaatc ccg                                33

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
tggcggaaac cccgggaatc                                               20

<210> SEQ ID NO 103
<211> LENGTH: 178
<212> TYPE: DNA
<213> ORGANISM: Artificial Sequence
<220> FEATURE:
<223> OTHER INFORMATION: Primer

<400> SEQUENCE: 103
gcttttagat cttaatacga ctcactatag ggagaccggc tgatgagtcc gtgaggacga   60
aacggtaccc ggtaccgtcg gaaacctgat catgtagatc gaatggactc taaatccgtt  120
cagccgggtt agattcccgg ggtttccgcc aggaagctta catccgtcga ccaaaagc    178
```

```
<210> SEQ ID NO 104
<211> LENGTH: 24
<212> TYPE: DNA
<213> ORGANISM: Artificial Sequence
<220> FEATURE:
<223> OTHER INFORMATION: Primer

<400> SEQUENCE: 104
ccgaaggtaa ctggcttagc agag                                           24

<210> SEQ ID NO 105
<211> LENGTH: 23
<212> TYPE: DNA
<213> ORGANISM: Artificial Sequence
<220> FEATURE:
<223> OTHER INFORMATION: Primer

<400> SEQUENCE: 105
tagaaaggtg aagaactgtt tac                                            23

<210> SEQ ID NO 106
<211> LENGTH: 30
<212> TYPE: DNA
<213> ORGANISM: Artificial Sequence
<220> FEATURE:
<223> OTHER INFORMATION: Primer

<400> SEQUENCE: 106
catatgtata tctccttctt aaagttaaac                                     30

<210> SEQ ID NO 107
<211> LENGTH: 23
<212> TYPE: DNA
<213> ORGANISM: Artificial Sequence
<220> FEATURE:
<223> OTHER INFORMATION: Primer

<400> SEQUENCE: 107
taatacgact cactataggg aga                                            23

<210> SEQ ID NO 108
<211> LENGTH: 44
<212> TYPE: DNA
<213> ORGANISM: Artificial Sequence
<220> FEATURE:
<223> OTHER INFORMATION: Primer

<400> SEQUENCE: 108
ccggctgatg agtccgtgag gacgaaacgg tacccggtac cgtc                     44

<210> SEQ ID NO 109
<211> LENGTH: 72
<212> TYPE: DNA
<213> ORGANISM: Artificial Sequence
<220> FEATURE:
<223> OTHER INFORMATION: Primer

<400> SEQUENCE: 109
ggaaacctga tcatgtagat cgaatggact ctaaatccgt tcagccgggt tagattcccg    60
gggtttccgc ca                                                        72

<210> SEQ ID NO 110
<211> LENGTH: 70
<212> TYPE: DNA
<213> ORGANISM: Artificial Sequence
<220> FEATURE:
```

```
<223> OTHER INFORMATION: Primer

<400> SEQUENCE: 110
cctcaactca gattaaaatt cgttttgttc agtgaatgat cttgccggat atcaaaaaaa     60
tattgacaac                                                           70

<210> SEQ ID NO 111
<211> LENGTH: 73
<212> TYPE: DNA
<213> ORGANISM: Artificial Sequence
<220> FEATURE:
<223> OTHER INFORMATION: Primer

<400> SEQUENCE: 111
gaaatctgaa agaaatagcc tgcgtatggc gcaggctatg aacagtgtgt ggtggaatcg     60
aaatctcgtg atg                                                       73

<210> SEQ ID NO 112
<211> LENGTH: 22
<212> TYPE: DNA
<213> ORGANISM: Artificial Sequence
<220> FEATURE:
<223> OTHER INFORMATION: Primer

<400> SEQUENCE: 112
cctcaactca gattaaaatt cg                                             22

<210> SEQ ID NO 113
<211> LENGTH: 19
<212> TYPE: DNA
<213> ORGANISM: Artificial Sequence
<220> FEATURE:
<223> OTHER INFORMATION: Primer

<400> SEQUENCE: 113
gaaatctgaa agaaatagc                                                 19

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
gaagcggaac acgtagaaag                                                20

<210> SEQ ID NO 115
<211> LENGTH: 52
<212> TYPE: DNA
<213> ORGANISM: Artificial Sequence
<220> FEATURE:
<223> OTHER INFORMATION: Primer

<400> SEQUENCE: 115
cctccttact gttgattcct gatgaaatca attgttatcc gctcacaatt cc            52

<210> SEQ ID NO 116
<211> LENGTH: 49
<212> TYPE: DNA
<213> ORGANISM: Artificial Sequence
<220> FEATURE:
<223> OTHER INFORMATION: Primer

<400> SEQUENCE: 116
```
caggaatcaa cagtaaggag gccccaatgt ctaaagaaaa gtttgaacg                49

<210> SEQ ID NO 117
<211> LENGTH: 49
<212> TYPE: DNA
<213> ORGANISM: Artificial Sequence
<220> FEATURE:
<223> OTHER INFORMATION: Primer

<400> SEQUENCE: 117
gtggtgatgg tgatgatggc cgctaccgct cagaactttt gctacaacg                49

<210> SEQ ID NO 118
<211> LENGTH: 42
<212> TYPE: DNA
<213> ORGANISM: Artificial Sequence
<220> FEATURE:
<223> OTHER INFORMATION: Primer

<400> SEQUENCE: 118
gccatcatca ccatcaccac taattgccga taacatttga cg                       42

<210> SEQ ID NO 119
<211> LENGTH: 40
<212> TYPE: DNA
<213> ORGANISM: Artificial Sequence
<220> FEATURE:
<223> OTHER INFORMATION: Primer

<400> SEQUENCE: 119
ctttctacgt gttccgcttc aaagaaaatc actgatgagc                          40

<210> SEQ ID NO 120
<211> LENGTH: 52
<212> TYPE: DNA
<213> ORGANISM: Artificial Sequence
<220> FEATURE:
<223> OTHER INFORMATION: Primer

<400> SEQUENCE: 120
gttttcctcc ttaaaatgct taatatatga attgttatcc gctcacaatt cc            52

<210> SEQ ID NO 121
<211> LENGTH: 43
<212> TYPE: DNA
<213> ORGANISM: Artificial Sequence
<220> FEATURE:
<223> OTHER INFORMATION: Primer

<400> SEQUENCE: 121
gcattttaag gaggaaaaca gtgtctaaag aaaaatttga acg                      43

<210> SEQ ID NO 122
<211> LENGTH: 49
<212> TYPE: DNA
<213> ORGANISM: Artificial Sequence
<220> FEATURE:
<223> OTHER INFORMATION: Primer

<400> SEQUENCE: 122
gtggtgatgg tgatgatggc cgctaccgcc cagaacttta gcaacaacg                49

<210> SEQ ID NO 123
<211> LENGTH: 43
<212> TYPE: DNA

```
<213> ORGANISM: Artificial Sequence
<220> FEATURE:
<223> OTHER INFORMATION: Primer

<400> SEQUENCE: 123
gccatcatca ccatcaccac taattacacg ttaattagtt ttg                43

<210> SEQ ID NO 124
<211> LENGTH: 41
<212> TYPE: DNA
<213> ORGANISM: Artificial Sequence
<220> FEATURE:
<223> OTHER INFORMATION: Primer

<400> SEQUENCE: 124
ctttctacgt gttccgcttc ataatttatt cgttctgaca g                  41

<210> SEQ ID NO 125
<211> LENGTH: 46
<212> TYPE: DNA
<213> ORGANISM: Artificial Sequence
<220> FEATURE:
<223> OTHER INFORMATION: Primer

<400> SEQUENCE: 125
ctgttacctc cttatctggg ttgaattgtt atccgctcac aattcc             46

<210> SEQ ID NO 126
<211> LENGTH: 44
<212> TYPE: DNA
<213> ORGANISM: Artificial Sequence
<220> FEATURE:
<223> OTHER INFORMATION: Primer

<400> SEQUENCE: 126
ccagataagg aggtaacaga tggcagctaa agacgtaaaa ttcg               44

<210> SEQ ID NO 127
<211> LENGTH: 47
<212> TYPE: DNA
<213> ORGANISM: Artificial Sequence
<220> FEATURE:
<223> OTHER INFORMATION: Primer

<400> SEQUENCE: 127
gtggtgatgg tgatgatggc cgctacccat catgccgccc atgccac            47

<210> SEQ ID NO 128
<211> LENGTH: 41
<212> TYPE: DNA
<213> ORGANISM: Artificial Sequence
<220> FEATURE:
<223> OTHER INFORMATION: Primer

<400> SEQUENCE: 128
gccatcatca ccatcaccac taattgccct gcacctcgca g                  41

<210> SEQ ID NO 129
<211> LENGTH: 38
<212> TYPE: DNA
<213> ORGANISM: Artificial Sequence
<220> FEATURE:
<223> OTHER INFORMATION: Primer

<400> SEQUENCE: 129
ctttctacgt gttccgcttc gtcgtccgtg tctgaatc                      38
```

<210> SEQ ID NO 130
<211> LENGTH: 50
<212> TYPE: DNA
<213> ORGANISM: Artificial Sequence
<220> FEATURE:
<223> OTHER INFORMATION: Primer

<400> SEQUENCE: 130
gacctcctta tcttccgttt tggtgttaat tgttatccgc tcacaattcc      50

<210> SEQ ID NO 131
<211> LENGTH: 48
<212> TYPE: DNA
<213> ORGANISM: Artificial Sequence
<220> FEATURE:
<223> OTHER INFORMATION: Primer

<400> SEQUENCE: 131
caaaacggaa gataaggagg tcaaaaatgt cgagtaagtt agtactgg      48

<210> SEQ ID NO 132
<211> LENGTH: 48
<212> TYPE: DNA
<213> ORGANISM: Artificial Sequence
<220> FEATURE:
<223> OTHER INFORMATION: Primer

<400> SEQUENCE: 132
gtggtgatgg tgatgatggc cgctaccggc agtcaggcgg ctcgcgtc      48

<210> SEQ ID NO 133
<211> LENGTH: 43
<212> TYPE: DNA
<213> ORGANISM: Artificial Sequence
<220> FEATURE:
<223> OTHER INFORMATION: Primer

<400> SEQUENCE: 133
gccatcatca ccatcaccac tgatttcaca ccgccagctc agc      43

<210> SEQ ID NO 134
<211> LENGTH: 40
<212> TYPE: DNA
<213> ORGANISM: Artificial Sequence
<220> FEATURE:
<223> OTHER INFORMATION: Primer

<400> SEQUENCE: 134
ctttctacgt gttccgcttc gggatcagca taataatacg      40

<210> SEQ ID NO 135
<211> LENGTH: 54
<212> TYPE: DNA
<213> ORGANISM: Artificial Sequence
<220> FEATURE:
<223> OTHER INFORMATION: Primer

<400> SEQUENCE: 135
acccgaccgt ccttaagtga ctacccctag gtaattgtta tccgctcaca attc      54

<210> SEQ ID NO 136
<211> LENGTH: 53
<212> TYPE: DNA
<213> ORGANISM: Artificial Sequence
<220> FEATURE:

<223> OTHER INFORMATION: Primer

<400> SEQUENCE: 136 acctagggt agtcacttaa ggacggtcgg gtatgaagaa aggttttatg ttg    53

<210> SEQ ID NO 137
<211> LENGTH: 49
<212> TYPE: DNA
<213> ORGANISM: Artificial Sequence
<220> FEATURE:
<223> OTHER INFORMATION: Primer

<400> SEQUENCE: 137
gtggtgatgg tgatgatggc cgctacctt accgctggtc attttttgg    49

<210> SEQ ID NO 138
<211> LENGTH: 48
<212> TYPE: DNA
<213> ORGANISM: Artificial Sequence
<220> FEATURE:
<223> OTHER INFORMATION: Primer

<400> SEQUENCE: 138
ggtagcggcc atcatcacca tcaccactaa ttgccctgca cctcgcag    48

<210> SEQ ID NO 139
<211> LENGTH: 44
<212> TYPE: DNA
<213> ORGANISM: Artificial Sequence
<220> FEATURE:
<223> OTHER INFORMATION: Primer

<400> SEQUENCE: 139
ctttctacgt gttccgcttc gtcgtccgtg tctgaatctt atac    44

<210> SEQ ID NO 140
<211> LENGTH: 45
<212> TYPE: DNA
<213> ORGANISM: Artificial Sequence
<220> FEATURE:
<223> OTHER INFORMATION: Primer

<400> SEQUENCE: 140 cctataccte cttattttct gtaaattgtt atccgctcac aattc    45

<210> SEQ ID NO 141
<211> LENGTH: 45
<212> TYPE: DNA
<213> ORGANISM: Artificial Sequence
<220> FEATURE:
<223> OTHER INFORMATION: Primer

<400> SEQUENCE: 141
tacagaaaat aaggaggtat agggtgatta gcgatatcag aaaag    45

<210> SEQ ID NO 142
<211> LENGTH: 48
<212> TYPE: DNA
<213> ORGANISM: Artificial Sequence
<220> FEATURE:
<223> OTHER INFORMATION: Primer

<400> SEQUENCE: 142
gtggtgatgg tgatgatggc cgctaccgaa ctgcatcagt tctgcttc    48

```
<210> SEQ ID NO 143
<211> LENGTH: 50
<212> TYPE: DNA
<213> ORGANISM: Artificial Sequence
<220> FEATURE:
<223> OTHER INFORMATION: Primer

<400> SEQUENCE: 143
ggtagcggcc atcatcacca tcaccactga tttcttgaac gacaaaaacg          50

<210> SEQ ID NO 144
<211> LENGTH: 38
<212> TYPE: DNA
<213> ORGANISM: Artificial Sequence
<220> FEATURE:
<223> OTHER INFORMATION: Primer

<400> SEQUENCE: 144
ctttctacgt gttccgcttc tgagacagaa taaaaagc                       38

<210> SEQ ID NO 145
<211> LENGTH: 45
<212> TYPE: DNA
<213> ORGANISM: Artificial Sequence
<220> FEATURE:
<223> OTHER INFORMATION: Primer

<400> SEQUENCE: 145
agtataccTC cttaattccg gataattgtt atccgctcac aattc               45

<210> SEQ ID NO 146
<211> LENGTH: 44
<212> TYPE: DNA
<213> ORGANISM: Artificial Sequence
<220> FEATURE:
<223> OTHER INFORMATION: Primer

<400> SEQUENCE: 146
atccggaatt aaggaggtat actatgcatc cacgttttca aacc                44

<210> SEQ ID NO 147
<211> LENGTH: 46
<212> TYPE: DNA
<213> ORGANISM: Artificial Sequence
<220> FEATURE:
<223> OTHER INFORMATION: Primer

<400> SEQUENCE: 147
gtggtgatgg tgatgatggc cgctaccagc gagaagcact cggtcg              46

<210> SEQ ID NO 148
<211> LENGTH: 46
<212> TYPE: DNA
<213> ORGANISM: Artificial Sequence
<220> FEATURE:
<223> OTHER INFORMATION: Primer

<400> SEQUENCE: 148
ggtagcggcc atcatcacca tcaccactaa gcctggtgcc ggatgc              46

<210> SEQ ID NO 149
<211> LENGTH: 40
<212> TYPE: DNA
<213> ORGANISM: Artificial Sequence
<220> FEATURE:
<223> OTHER INFORMATION: Primer
```

<400> SEQUENCE: 149
ctttctacgt gttccgcttc aatttcgaca ccaggagagg    40

<210> SEQ ID NO 150
<211> LENGTH: 51
<212> TYPE: DNA
<213> ORGANISM: Artificial Sequence
<220> FEATURE:
<223> OTHER INFORMATION: Primer

<400> SEQUENCE: 150
ttagaggacc tccttatatt taagtttgta attgttatcc gctcacaatt c    51

<210> SEQ ID NO 151
<211> LENGTH: 53
<212> TYPE: DNA
<213> ORGANISM: Artificial Sequence
<220> FEATURE:
<223> OTHER INFORMATION: Primer

<400> SEQUENCE: 151
acaaacttaa atataaggag gtcctctaaa tggctattga acgtactttt tcc    53

<210> SEQ ID NO 152
<211> LENGTH: 49
<212> TYPE: DNA
<213> ORGANISM: Artificial Sequence
<220> FEATURE:
<223> OTHER INFORMATION: Primer

<400> SEQUENCE: 152
gtggtgatgg tgatgatggc cgctaccacg ggtgcgcggg cacacttcg    49

<210> SEQ ID NO 153
<211> LENGTH: 45
<212> TYPE: DNA
<213> ORGANISM: Artificial Sequence
<220> FEATURE:
<223> OTHER INFORMATION: Primer

<400> SEQUENCE: 153
ggtagcggcc atcatcacca tcaccactaa taatttcgta aatgc    45

<210> SEQ ID NO 154
<211> LENGTH: 38
<212> TYPE: DNA
<213> ORGANISM: Artificial Sequence
<220> FEATURE:
<223> OTHER INFORMATION: Primer

<400> SEQUENCE: 154
ctttctacgt gttccgcttc gggttgaaaa aagaaacg    38

<210> SEQ ID NO 155
<211> LENGTH: 57
<212> TYPE: DNA
<213> ORGANISM: Artificial Sequence
<220> FEATURE:
<223> OTHER INFORMATION: Primer

<400> SEQUENCE: 155 tttataccte cttattctag tttgttgtgt gggtcaattg ttatccgctc acaattc    57

<210> SEQ ID NO 156
<211> LENGTH: 59

<212> TYPE: DNA
<213> ORGANISM: Artificial Sequence
<220> FEATURE:
<223> OTHER INFORMATION: Primer

<400> SEQUENCE: 156
gacccacaca acaaactaga ataaggaggt ataaaatgac agatgtaacg attaaaacg    59

<210> SEQ ID NO 157
<211> LENGTH: 49
<212> TYPE: DNA
<213> ORGANISM: Artificial Sequence
<220> FEATURE:
<223> OTHER INFORMATION: Primer

<400> SEQUENCE: 157
gtggtgatgg tgatgatggc cgctaccagc aatggtacgt tggatctcg    49

<210> SEQ ID NO 158
<211> LENGTH: 49
<212> TYPE: DNA
<213> ORGANISM: Artificial Sequence
<220> FEATURE:
<223> OTHER INFORMATION: Primer

<400> SEQUENCE: 158
ggtagcggcc atcatcacca tcaccactaa ggttttagg gttccatgc    49

<210> SEQ ID NO 159
<211> LENGTH: 41
<212> TYPE: DNA
<213> ORGANISM: Artificial Sequence
<220> FEATURE:
<223> OTHER INFORMATION: Primer

<400> SEQUENCE: 159
ctttctacgt gttccgcttc aaattaattt caggtggaag g    41

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
ctgctcccgg ttttagttcc    20

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
taccgatctc ttcagagatc    20

<210> SEQ ID NO 162
<211> LENGTH: 20
<212> TYPE: DNA
<213> ORGANISM: Artificial Sequence
<220> FEATURE:
<223> OTHER INFORMATION: Primer

<400> SEQUENCE: 162
cacttcagat tcgaacttgg                                               20

<210> SEQ ID NO 163
<211> LENGTH: 20
<212> TYPE: DNA
<213> ORGANISM: Artificial Sequence
<220> FEATURE:
<223> OTHER INFORMATION: Primer

<400> SEQUENCE: 163
gggtaccttc tttgttgatg                                               20

<210> SEQ ID NO 164
<211> LENGTH: 21
<212> TYPE: DNA
<213> ORGANISM: Artificial Sequence
<220> FEATURE:
<223> OTHER INFORMATION: Primer

<400> SEQUENCE: 164
ggaattcttt catctctttc g                                             21

<210> SEQ ID NO 165
<211> LENGTH: 20
<212> TYPE: DNA
<213> ORGANISM: Artificial Sequence
<220> FEATURE:
<223> OTHER INFORMATION: Primer

<400> SEQUENCE: 165
acgttgattt tcagtgtacg                                               20

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
ttcaacagaa ttaacgctcc                                               20

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
caaagaaata agcgatttcg                                               20

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
gacgcaggat aactttatgg                                               20

<210> SEQ ID NO 169
<211> LENGTH: 20
<212> TYPE: DNA
<213> ORGANISM: Artificial Sequence

```
<220> FEATURE:
<223> OTHER INFORMATION: Primer

<400> SEQUENCE: 169
cgagaaagta tccatcatgg                                                   20

<210> SEQ ID NO 170
<211> LENGTH: 20
<212> TYPE: DNA
<213> ORGANISM: Artificial Sequence
<220> FEATURE:
<223> OTHER INFORMATION: Primer

<400> SEQUENCE: 170
atctgaaaga aatagcctgc                                                   20
```